(12) United States Patent
Wheeler et al.

(10) Patent No.: US 7,371,922 B2
(45) Date of Patent: May 13, 2008

(54) NUCLEAR TRANSFER WITH PORCINE EMBRYONIC STEM CELLS

(75) Inventors: Matthew B. Wheeler, Tolono, IL (US); Brett R. White, Lincoln, NE (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 534 days.

(21) Appl. No.: 10/632,118

(22) Filed: Jul. 31, 2003

(65) Prior Publication Data
US 2004/0107454 A1 Jun. 3, 2004

Related U.S. Application Data

(60) Provisional application No. 60/400,287, filed on Jul. 31, 2002.

(51) Int. Cl.
A01K 67/027 (2006.01)
C12N 15/00 (2006.01)
(52) U.S. Cl. .......................... 800/24; 800/17
(58) Field of Classification Search ............ 800/14–18, 800/24
See application file for complete search history.

(56) References Cited

U.S. PATENT DOCUMENTS

| | | | |
|---|---|---|---|
| 4,994,384 | A | 2/1991 | Prather et al. |
| 5,057,420 | A | 10/1991 | Massey |
| 5,523,226 | A | 6/1996 | Wheeler |
| 5,994,619 | A | 11/1999 | Stice et al. |
| 6,011,197 | A | 1/2000 | Strelchenko et al. |
| 6,025,540 | A | 2/2000 | Hansson |
| 6,080,912 | A | 6/2000 | Bremel et al. |
| 6,156,569 | A | 12/2000 | Ponce de Leon et al. |
| 6,193,647 | B1 | 2/2001 | Beebe et al. |
| 6,258,998 | B1 | 7/2001 | Damiani et al. |
| 2003/0070186 | A1 | 4/2003 | Strelchenko |

OTHER PUBLICATIONS

Chen et al. Theriogenology 52:195-212, 1999.*
Denning et al. Reproduction 126:1-11, 2003.*
Shim et al. Biol. Reprod. 57:1089-1095, 1997.*
Kuhholzer et al. Mol Reprod Dev 56:145-148, 2000.*
Sato et al. Human Cell 13(4):197-202.*
Wilmut et al. Nature 385:810-813, Feb. 1997.*
Wheeler et al. Reprod. Fertil. Dev. 6:563-568, 1994—IDS reference for 103 rejection.*
Wakayama et al. Mice cloned from embryonic stem cells. Proc. Natl. Acad. Sci. (USA). Dec. 21, 1999. vol. 96, No. 26, pp. 14984-14989.*
Tatham et al. Enucleation by Centrifugation of In Vitro-Matured Bovine Oocytes for Use in Nuclear Transfer. Bio. Reprod., vol. 53, pp. 1088-1094.*
Allen et al. (1984). "In vitro Development of Porcine Embryos in Coculture with Endometrical Cell Monolayers or Culture Supernatants," *J. Anim. Sci.* 59:1657-1661.
Amano et al. (2001) "Full-Term Development of Enucleated Mouse Oocytes Fused with Embryotic Stem Cells from Different Cell Lines," *Reproduction* 121:729-733, 2001.
Amano, et al. (2001) "Mouse Cloned from Embryonic Stem (ES) Cells Synchronized in Metaphase with Nocodazole," *J. Exp. Zoo.* 289:139-145.
Archibong et al. (1989) "Development of Porcine Embryos From One- and Two-Cell Stages to Blastocysts in Culture Medium Supplemented with Porcine Oviductal Fluid," *Biol. Reprod.* 41:1076-1083.
Balakier et al. (1993) "Experimentally Induced Parthenogenetic Activation of Human Oocytes," *Hum. Reprod.* 8(5):740-743.
Barnes et al. (1993) "Influence of Recipient Oocyte Cell Cycle Stage on DNA Synthesis, Nuclear Envelope Breakdown, Chromosome Constitution, and Development in Nuclear Transplant Bovine Embryos," *Mol. Reprod. Dev.* 36:33-41.
Bleck et al. (1998) "Production of Bovine Alpha-Lactalbumin in the Milk of Transgenic Pigs," *J. Anim. Sci.* 76:3072-3078.
Boston et al. (2001) "Short Communication: Effects of Increased Expression of Alpha-Lactalbumin in Transgenic Mice on Milk Yield and Pup Growth," *J. Dairy Sci.* 84:620-622.
Bradshaw et al. (1995) "UV Irradiation of Chromosomal DNA and its Effect upon MPF and Meiosis in Mammalian Oocytes," *Mol. Reprod. Dev.* 41:503-512.
Brem et al. (1985) "Production of Transgenic Mice, Rabbits and Pigs by Microinjection into Pronuclei," *Zuchthygiene* 20:251-252.
Campbell et al. (1994) "Improved Development to Blastocyst of Ovine Nuclear Transfer Embryos Reconstructed During the Presumptive S-phase of Enucleated Activated Oocytes," *Biol. Reprod.* 50:1385-1393.
Campbell et al. (1994) "Recent Advances on in vitro Culture and Cloning of Ungulate Embryos," Proceedings of the 5th International Congr. on Genetics Applied to Livestock Production 20:180-187.
Campbell et al. (1997) "Totipotency or Multipotentiality of Cultured Cells: Applications and Progress," *Theriogenology* 47:63-72.
Campbell et al. (1996) "Sheep Cloned by Nuclear Transfer from a Cultured Cell Line," *Nature* 380:64-66.
Campbell et al. (1996) "Cell Cycle Co-Ordination in Embryo Cloning by Nuclear Transfer," *Rev. Reprod.* 1:40-46.
Chastant et al. (1996) "Quantitative Control of Gene Expression by Nucleocytoplasmic Interactions in Early Mouse Embryos: Consequence for Reprogammation by Nuclear Transfer," *Mol. Reprod. Dev.* 44:423-432.
Cheong et al. (1993) "Assessment of Cytoplasmic Effects on the Development of Mouse Embryonic Nuclei Transferred to Enucleated Zygotes," *Theriogenology* 39:451-461.
Cheong et al. (1992) "Development of Mouse Embryonic Nuclei Transferred to Enucleated Oocytes and Zygotes," *Jpn. J. Vet. Res.* 40:149-159.

(Continued)

Primary Examiner—Deborah Crouch
(74) Attorney, Agent, or Firm—Greenlee, Winner and Sullivan, P.C.

(57) ABSTRACT

Provided is a method for the production of transgenic animals, especially pigs, by the use of nuclear transfer from genetically modified or other embryonic stem cells to either enucleated oocytes which were matured in vivo or in vitro and activated or to enucleated zygotes.

19 Claims, 12 Drawing Sheets

OTHER PUBLICATIONS

Cheong et al. (1993) "Birth of Mice After Transplantation of Early Cell-Cycle-Stage Embryonic Nuclei into Enucleated Oocytes," *Biol. Reprod.* 48:958-963.

Cheong et al. (1994) "Relationship Between Nuclear Remodeling and Subsequent Development of Mouse Embryonic Nuclei Transferred to Enucleated Oocytes," *Mol. Reprod. Dev.* 37:138-145.

Cibelli et al. (1997) "Production of Germline Chimeric Bovine Fetuses From Transgenic Embryonic Stem Cells," *Theriogenology* 47:241 (Abstr.).

Collas et al. (1994) "Nuclear Transplantation by Microinjection of Inner Cell Mass and Granulosa Cell Nuclei," *Mol. Reprod. Dev.* 38:264-267.

Collas et al. (1989) "Electrical Activation of Mouse Oocytes," *Theriogenology* 32:835-844.

Collas et al. (1990) "Factors Affecting the Efficiency of Nuclear Transplantation in the Rabbit Embryo," *Biol. Reprod.* 43:877-884.

Collas et al. (1991) "Relationship Between Nuclear Remodeling and Development in Nuclear Transplant Rabbit Embryos," *Biol. Reprod.* 45:455-465.

Cuthbertson, K.S.R. (1983) "Parthenogenetic Activation of Mouse Oocytes in vitro with Ethanol and Benzyl Alcohol," *J. Exp. Zool.* 226:311-314.

Czolowska et al. (1984) "Behaviour of Thymocyte Nuclei in Nonactivated and Activated Mouse Oocytes," *J. Cell Sci.* 69:19-34, 1984.

Delhaise et al. (1995) "Nuclear Transplantation Using Bovine Primordial Germ Cells From Male Fetuses," *Reprod. Fertil. Dev.* 7:1217-1219.

Didion et al. (1990) "Parthenogenetic Activation of Mouse and Pig Oocytes Matured in vitro," *Theriogenology* 33:1165-1175.

Du et al. (1995) "Nuclear Transfer of Putative Rabbit Embryonic Stem Cells Leads to Normal Blastocyst Development," *J. Reprod. Fertil.* 104:219-223.

Du et al. (1995) "Beneficial Effect of Oocyte Activation Prior to and During Nuclear Transfer in Cattle Using in vitro Matured Oocytes 24 h of Age," *Reprod. Nutr. Dev.* 35:703-712.

Eberhardt et al. (1994) "Oviductal Fluid and Growth Factors Failed to Enhance Development of Porcine Embryos," *Theriogenology* 41:1163-1172.

First et al. (1992) "Use of in vitro Matured Oocytes 24 hr of Age in Bovine Nuclear Transfer," *Theriogenology* 37:211 (Abstr.).

Fulka et al. (1996) "Nuclear Transplantation in Mammals: Remodeling of Transplanted Nuclei Under the Influence of Maturation Promoting Factor," *BioEssays* 18:835-840.

Fulka et al. (1994) "Nuclear Transplantation in Mammals: The Role of Maturation Promoting Factor," *Reprod. in Domest. Anim.* 29:352-353.

Fulka et al. (1993) "Noninvasive Chemical Enucleation of Mouse Oocytes," *Mol. Reprod. Dev.* 34:427-430.

Gerfen et al. (1995) "Isolation of Embryonic Cell-lines from Porcine Blastocysts," *Anim. Biotechnology* 6:1-14.

Grocholova et al. (1997) "The Protein Phosphatase Inhibitor Okadaic Acid Inhibits Exit from Metaphase II in Parthenogenetically Activated Pig Oocytes," *J. Exp. Zool.* 277:49-56.

Hagen et al. (1991) "Response of Porcine Oocytes to Electrical and Chemical Activation During Maturation in vitro," *Mol. Reprod. Dev.* 28:70-73.

Hammer et al. (1985) "Production of Transgenic Rabbits, Sheep and Pigs by Microinjection," *Nature (Lond.)* 315:680-683.

Howlett et al. (1987) "Nuclear Cytoplasmic Interactions Following Nuclear Transplantation in Mouse Embryos," *Development* 101:915-923.

Illmensee et al. (1981) "Nuclear Transplantation in Mus musculus: Developmental Potential of Nuclei from Preimplantation Embryos," *Cell* 23:9-18.

Kashiwazaki et al. (1992) "Production of Chimeric Pgis by the Blastocyst Injection Method," *Vet. Rec.* 130:186-187.

Keefer et al. (1992) "In vitro Culture of Bovine Nucleus Transfer Embryos," *Biol. Reprod.* 46 (Suppl. 1):166 (Abstr.).

Keefer et al. (1994) "Bovine Inner Cell Mass Cells as Donor Nuclei in the Production of Nuclear Transfer Embryos and Calves," *Biol. Reprod.* 50:935-939.

Kono et al. (1991) "Production of Identical Twin and Triplet Mice by Nuclear Transplantation," *J. Exp. Zool.* 257:214-219.

Kono et al. (1991) "Development of Enucleated Mouse Oocytes Reconstituted with Embryonic Nuclei," *J. Reprod. Fertil.* 93:165-172.

Kono et al. (1992) "Development of Mouse Enucleated Oocytes Receiving a Nucleus from Different Stages of the Second Cell cycle," *J. Reprod. Fertil.* 94:481-487.

Kono et al. (1994) "Effect of Ooplast Activation on the Development of Oocytes Following Nucleus Transfer in Cattle," *Theriogenology* 41:1463-1471.

Kure-bayashi et al. (1996) "Development of Porcine Blastocysts From in vitro-Matured and Activated Haploid and Diploid Oocytes," *Theriogenology* 46:1027-1036.

Kwon et al. (1996) "Production of Identical Sextuplet Mice by Transferring Metaphase Nuclei From Four-Cell Embryos," *Proc. Natl. Acad. Sci. USA* 93:13010-13013.

Laurincik et al. (1994) "Differences in Pronucleus Formation and First Cleavage Following in vitro Fertilization Between Pig Oocytes Matured in vivo and in vitro," *J. Reprod. Fertil.* 102:277-284.

Laurincik et al. (1994) "Ovulation, Fertilization and Pronucleus Development in Superovulated Gilts," *Theriogenology* 41:447-452.

Lavoir et al. (1997) "Development of Bovine Nuclear Transfer Embryos Made with Oogonia," *Biol. Reprod.* 56:194-199.

Lee et al. (2002) "Cloned Zebrafish by Nuclear Transfer from Long-Term-Cultured Cells," *Nat. Biotechnol.* 20:795-799.

Lee et al. (1993) "Effects of Fusion Medium, Voltage and Micromanipulation on Activation of Pig Oocytes and Blastomere Development," *Theriogenology* 39:257 (Abstr.).

Machaty et al. (1995) "Parthenogenetic Activation of Porcine Oocytes with Guanosine-5'-O-(3'-thiotriphosphate)," *Biol. Reprod.* 52:753-758.

McGrath et al. (1984) "Inability of Mouse Blastomere Nuclei Transferred to Enucleated Zygote to Support Development in vitro," *Science* 226:1317-1319.

Meyen et al. (1989) "Development of Pig Blastocysts in vitro is Altered by Serum, Bovine Serum Albumin and Amino Acids and Vitamins," *Theriogenology* 31:463-471.

Minamihashi et al. (1993) "Bovine Parthenogenetic Blastocysts Following in vitro Maturation and Oocyte Activation with Ethanol," *Theriogenology* 40:63-76.

Mitalipov et al. (2002) "Rhesus Monkey Embryos Produced by Nuclear Transfer from Embryonic Blastomeres or Somatic Cells," *Biol. Reprod.* 66:1367-1373.

Modlinski et al. (1996) "Embryonic Stem Cells: Developmental Capabilities and Their Potential Use in Mammalian Embryo Cloning," *Anim. Reprod. Sci.* 42:437-446.

Moens et al. (1996) "Assessment of Nuclear Totipotency of Fetal Bovine Diploid Germ Cells by Nuclear Transfer," *Theriogenology* 46:871-880.

Nagai, T. (1987) "Parthenogenetic Activation of Cattle Follicular Oocytes in vitro with Ethanol," *Gamete Res.* 16:243-249.

Nagashima et al. (1992) "Development of Porcine Nuclear Transplant Embryos from 8-16 Cell Stage Donor Nuclei," *Theriogenology* 37:263 (Abstr.).

Nagy et al. (1993) "Derivation of Completely Cell Cultured-Derived Mice from Early-Passage Embryonic Stem Cells," *Proc. Natl. Acad. Sci. USA* 90:8424-8428.

Niwa, K. (1993) "Effectiveness of in vitro Maturation and in vitro Fertilization Techniques in Pigs," *J. Reprod. Fertil. Suppl.* 48:49-59.

Noble et al. (2002) "Lactational Performance of First-Parity Transgenic Gilts Expressing Bovine Alpha-Lactalbumin in their Milk," *J. Anim. Sci.* 80:1090-1096.

Notarianni et al. (1991) "Derivation of Pluripotent, Embryonic Cell Lines from the Pig and Sheep," *J. Reprod. Fertil.* Suppl. 43:255-260.

Nussbaum et al. (1995) "Differential Effects of Protein Synthesis Inhibitors on Porcine Oocyte Activation," *Mol. Reprod. Dev.* 41:70-75.

Ogura et al. (2000) "Birth of Mice After Nuclear Transfer by Electrofusion Using Tail Tip Cells," *Mol. Repro Dev.* 57:55-59.

Otaegui et al. (1994) "Nuclear Transfer of 4-cell Mouse Embryos: Synchronization with Cytoplast Partially Overcomes Nuclear Donor Cell-Cycle Effect," *J. Reprod. Fertil.* Abstr. Series No. 13:24 (Abstr.).

Otaegui et al. (1994) "Transfer of Nuclei from 8-cell Stage Mouse Embryos Following Use of Nocodazole to Control the Cell Cycle," *Mol. Reprod. Dev.* 39:147-152.

Ouhibi et al. (1996) "Nuclear Transplantation of Ectodermal Cells in Pig Oocytes: Ultrastructure and Radiography," *Mol. Reprod. Dev.* 44:533-539.

Petr et al. (1996) "Activation of in vitro Matured Pig Oocytes by Combined Treatment of Ethanol and Cycloheximide," *Theriogenology* 45:1473-1478.

Petters et al. (1993) "Culture of Pig Embryos," *J. Reprod. Fertil.* Suppl. 48:61-73.

Prather, R. S. (1993) "Nuclear Control of Early Embryonic Development in Domestic Pigs," *J. Reprod. Fertil.* Suppl. 48:17-29.

Prather et al. (1987) "Nuclear Transplantation in the Bovine Embryo: Assessment of Donor Nuclei and Recipient Oocyte," *Biol. Reprod.* 37:859-866.

Prather et al. (1989) "Nuclear Transplantation in Early Pig Embryos," *Biol. Reprod.* 41:414-418.

Prather et al. (1990) "Nuclear Transplantation in the Pig Embryo: Nuclear Swelling," *J. Exp. Zool.* 255:355-358.

Prather et al. (1990) "Nuclear Transfer in Mammalian Embryos," *Int. Rev. Cytol.* 120:169-190.

Prather et al. (1991) "Artificial Activation of Porcine Oocytes Matured in vitro," *Mol. Reprod. Dev.* 28:405-409.

Prochazka et al. (1995) "Behaviour of Blastomere Nuclei Fused to Mouse Oocytes is Affected by Oocyte Enucleation and Age," *Reprod. Nutr. Dev.* 35:695-701.

Reed et al. (1992) "In vitro Culture of Pig Embryos," *Theriogenology* 37:95-109.

Rickords et al. (1993) "Okadaic Acid Increases Rate of Activation of Electrically Activated in vitro Matured Porcine Oocytes," *Theriogenology* 39:296 (Abstr.).

Rideout et al. (2001) "Nuclear Cloning and Epigenetic Reprogramming of the Genome," *Science* 293:1093-1098.

Robertson et al. (1986) "Germ-line Transmission of Genes Introduced into Cultured Pluripotent Cells by Retroviral Vector," *Nature (Lond.)* 323:445-448.

Robl et al. (1986) "Nuclear Transplantation in Mouse Embryos: Assessment of Recipient Cell Stage," *Biol. Reprod.* 34:733-739.

Robl et al. (1985) "Manipulation of Gametes and Embryos in the Pig," *J. Reprod. Fertil.* Suppl. 33:101-114.

Robl et al. (1992) "Electrically Induced Fusion and Activation in Nuclear Transplant Embryos," In: D. C. Chang, B. M. Chassy, J. A. Saunders and A. E. Sowers (Ed.) *Guide to Electroporation and Electrofusion* pp. 535-551. Harcourt Brace Jovanovich, San Diego, CA.

Robl et al. (1992) "Cell Fusion and Oocyte Activation," Proceedings of the Symp. on Cloning Mammals by Nuclear Transplantation. pp. 21-23. Jan. 15, 1992. Fort Collins, CO.

Samake et al. (1996) "Synchronization of Cell Division in Eight-Cell Bovine Embryos Produced in vitro: Effects of Nocodazole," *Mol. Reprod. Dev.* 44:486-492.

Schoenbeck et al. (1993) "Diacylglycerol-Enhanced Electrical Activation of Porcine Oocytes Matured in vitro," *Theriogenology* 40:257-266.

Schoonjans et al. (1996) "Pluripotential Rabbit Embryonic Stem (ES) Cells are Capable of Forming Overt Coat Color Chimeras Following Injection into Blastocysts," *Mol. Reprod. Dev.* 45:439-443.

Shi et al. (1993) "Synergistic Effect of A23187 and Cycloheximide Allows Effective Activation of Freshly Matured Bovine Oocytes," *Theriogenology* 39:309 (Abstr.).

Shin et al. (2002) "A Cat Cloned by Nuclear Transplantation," *Nature* 415:859.

Sims et al. (1993) "Production of Calves by Transfer of Nuclei from Cultured Inner Cell Mass Cells," *Proc. Natl. Acad. Sci. USA* 90:6143-6147.

Slapak et al. (1989) "Effect of Procedures Utilized for Nuclear Transfer on Bovine Oocyte Activation," *Theriogenology* 31:258 (Abstr.).

Smith et al. (1988) "Influence of Cell Cycle Stage at Nuclear Transplantation on the Development in vitro of Mouse Embryos," *J. Reprod. Fertil.* 84:619-624.

Solter et al. (1985) "Nuclear Transfer in Mouse Embryos: Activation of the Embryonic Genome," Cold Spring Harbor Symp. on Quantitative Biology L:45-50. Cold Spring Harbor Laboratory, Cold Spring Harbor, NY.

Stewart, C. L. (1993) "Production of Chimeras Between Embryonic Stem Cells and Embryos," *Methods Enzymol.* 225:823-855.

Stice et al. (1996) "Pluripotent Bovine Embryonic Cell Lines Direct Embryonic Development Following Nuclear Transfer," *Biol. Reprod.* 54:100-110.

Stumpf et al. (1993) "Processing of Nuclei Transplanted into in vitro Matured Porcine Oocytes," *Theriogenology* 39:322 (Abstr.).

Szollosi et al. (1988) "Remodeling of Mouse Thymocyte Nuclei Depends on the Time of Their Transfer into Activated, Homologous Oocytes," *J. Cell Sci.* 91:603-613.

Tadir et al. (1993) "Lasers for Gamete Micromanipulation: Basic Concepts," *J. Assisted Reprod. Genet.* 10:121-125.

Terlouw et al. (1992) "In vitro Development of Nuclear Transplant Pig Embryos," *Theriogenology* 37:309 (Abstr.).

Terlouw et al. (1993) "Pig Oocyte Activation and Processing of Transplanted Nuclei," *Theriogenology* 39:329 (Abstr.).

Wagoner et al. (1996) "Functional Enucleation of Bovine Oocytes: Effects of Centerfugation and Ultraviolet Light," *Theriogenology* 46:279-284.

Ware et al. (1989) "Age Dependence of Bovine Oocyte Activation," *Gamete Res.* 22:265-275.

Wheeler, M. B. (1994) "Development and Validation of Swine Embryonic Stem Cells: A Review," *Reprod. Fertil. Dev.* 6:563-568.

Wheeler et al. (1993) "Strategies for Improving Swine Growth," In: G. R. Hollis (Ed.) *Growth of the Pig*, pp. 167-183. CAB International, Wallingford, UK.

Wheeler et al. (1995) "The Use of Embryonic Stem Cells in the Production of Transgenic Livestock," *Embryo Transfer Newsletter* 13:20-25.

Wheeler, M.B. (1997) "Nuclear Transfer with Porcine Embryonic Stem Cells," P.H.D. Thesis, University of Illinoi,Dec. 2001.

White, B.R. (2001) "Transgenic Technology and Applications in Swine" *Theriogenology* 56(8):1354-1369.

Wolf et al. (1999) "Nuclear Transfer in the Rhesus Monkey: Practical and Basic Implications," *Biol. Repro.* 60:199-204.

Wood et al. (1993) "Non-injection Methods for the Production of Embryonic Stem Cell-Embryo Chimeras," *Nature (Lond.)* 365:87-89.

Wright, R.W., Jr. (1977) "Successful Culture in vitro of Swine Embryos to the Blastocyst Stage," *J. Anim. Sci.* 44:854-858.

Yamauchi et al. (1996) "Effect of Culture Conditions on Artificial Activation of Porcine Oocytes Matured in vitro," *Reprod. Fertil. Dev.* 8:1153-1156.

Yang et al. (1994) "Synergistic Effect of Ethanol and Cycloheximide on Activation of Freshly Matured Bovine Oocytes," *Theriogenology* 41:395-403.

Youngs et al. (1993) Investigations into the Control of Litter Size in Swine. I. Comparative Studies on in vitro Development of Meishan and Yorkshire Preimplantation Embryos. *J. Anim. Sci.* 71:1561-1565.

\* cited by examiner

FIG. 11A  FIG. 11B

NUCLEAR TRANSFER WITH PORCINE EMBRYONIC STEM CELLS

CROSS REFERENCE TO RELATED APPLICATIONS

This application claims benefit of U.S. Provisional Application No. 60/400,287, filed Jul. 31, 2002.

ACKNOWLEDGMENT OF FEDERAL RESEARCH SUPPORT

This invention was made, at least in part, with funding from the United States Department of Agriculture (Project # AG 95-37205-2311). Accordingly, the United States Government has certain rights in this invention.

BACKGROUND OF THE INVENTION

The field of this invention is the area of methods for the genetically engineering of non-human animals, in particular those comprising the step of nuclear transfer, and animals produced by such methods.

Techniques for transgenic animal production have been well established for mice (Gordon and Ruddle, 1981) and pigs (Brem et al., 1985; Hammer et al., 1985). However, efficiencies for production of transgenic animals, especially large domestic animals, are generally low. The efficiency of producing a transgenic pig from pronuclear injection can range from 1 to 10% at a cost of approximately $25,000 (Wheeler and White, 1993). The possible use of embryonic stem (ES) cells to produce transgenic animals provides a unique opportunity to increase the efficiency and decrease the cost of transgenic pig production as well as provide more stable gene integration (Wheeler, 1994).

Embryonic stem cells offer an effective tool for producing genetically identical individuals. Embryonic stem cells can be electroporated with deoxyribonucleic acid (DNA) to introduce, replace or inactivate genes of interest. These ES cells can be screened, in vitro, for incorporation of genes in the appropriate location within the genome. Theoretically, screened ES cells could be used as karyoplasts (donor nuclei) for nuclear transfer (NT) to produce an entire individual. This technology has many exciting uses including acceleration of genetic progress, propagation of superior genetic lines and production of transgenic animals. Transgenic animals can be developed for the production of human pharmaceutical proteins, tissues and organs for human transplantation, and animals with improved quantitative traits (i.e., reproduction, growth, carcass or milk composition; Wheeler, 1994). Further, development of NT embryos provides a method for testing the totipotency of ES cell lines.

Nuclear transfer has been reported in amphibians, mice, rats, rabbits, sheep, pigs, cattle (see Prather and First [1990] for review), goats (Yong et al., 1991), domestic cats (Shin et al., 2002), monkeys (Mitalipov et al., 2002), fish (Lee et al., 2002) and mules (Holden, 2003). Numerous studies concerning NT with blastomeres from early embryonic stages have been reported (Prather and First, 1990). However, the number of genetically identical blastomeres is limited with these transfers.

There is a need in the art for efficient means for producing transgenic animals and for reproducing animals, endangered species as well as domesticated livestock.

SUMMARY OF THE INVENTION

The present invention provides methods and materials for the production of non-human animals having a genome of interest, including a genetically modified genome containing at least one heterologous DNA sequence (a transgene) using nuclear transfer to convey genetic material of interest from transgenic or other embryonic stem cells from an embryo or animal of the particular species into enucleated activated oocytes or enucleated zygotes of the appropriate developmental stage. The zygotes are the product of fertilization of an egg (oocyte) with sperm, and fertilization can occur either in vivo or in vitro. The genetic material of interest can be a genome which has been genetically engineered to contain and express a protein or noncoding nucleic acid of interest or to contain characteristic nucleic acid sequences of interest, for example, sequences with which progeny animals are to be identified, and/or to express a phenotype of interest by virtue of expression of the protein or nucleic acid of interest. As specifically exemplified herein, the nuclear transfer with embryonic stem cells, which are totipotent, has been demonstrated with porcine cells and transgenic swine, but it is applicable to other nonhuman animals, including bovines, equines, ovines, caprines, felines, canines, avians, rodents, primates, amphibians, reptiles and other animals in which implantation of embryos is known to the art. The use of cultured ES cells of a genotype of interest or genetically modified ES cells allows the generation of transgenic animals or other animals of defined genetic makeup characterized prior to nuclear transfer and production of an animal through nuclear transfer.

The oocytes or zygotes can be enucleated chemically, mechanically or with electromagentic irradiation. Chemical enucleation can be accomplisehd, for example, by treatment of metaphase I oocytes in etoposide-supplemented medium followed by treatment in a medium containing a combination of etoposide and cycloheximide. Mechanical enucleation can be achieved by micromanipulation to remove the germinal vesicle from an immature oocyte, a polar body and metaphase chromosomes from an in vivo or in vitro matured oocyte or a nucleus or pronucleus from a zygote or embryo produced in vivo or in vitro, or by oocyte bisection. Alternatively, mechanical enucleation can be accomplished using density gradient centrifugation of the cells, especially oocytes, through a Percoll gradient at 15,000×g for 2 minutes. Enucleation through the use of electromagnetic irradiation can be with ultraviolet (UV) light, e.g., irradiation of metaphase II chromosomes of pig oocytes with UV light at 254 nm.

Oocytes from the animal of a known or unknown genetic background are matured in vitro or in vivo and then activated prior to enucleation in preparation for nuclear transfer. Ooocytes can be matured in vivo or in vitro and activated by cold shock, sham enucleation, electroactivation or electroactivation in combination with culture in the presence of cycloheximide. Alternatively, enucleated zygotes can be enucleated and in some cases, provide results better than enucleated activated oocytes, especially in the case of porcines. Cold shock, sham enucleation, electroactivation and electroactivation in combination with culture in the presence of cycloheximide improved activation of oocytes, as exemplified herein using porcine oocytes. Oocytes or zygotes are enucleated. Nuclear transfer is carried out using micromanipulation techniques. A single ES cell is placed under the zona pellucida, adjacent to the vitelline membrane of the enucleated oocyte or zygote. Then the ES cell-oocyte complex is equilibrated in fusion medium (as specifically exemplified herein) between two flat electrodes, oriented so that the fusion plane is parallel to the electrodes, and the complexes are pulsed with electricity to effect fusion and produce NT embryos. After fusion, the NT embryos are washed with medium and cultured. As specifically exemplified herein, the NT embryo is cultured to the blastocyst or compact morula stage. Then the cultured embryo is implanted into the uterus of a suitable surrogate mother, and carried to term.

The step of enucleation of the oocyte or zygote can be accomplished by micromanipulation, by chemical treatment or by treatment with appropriate electromagnetic radiation, e.g., laser or ultraviolet light.

The nuclear transfer can be accomplished by microinjection, by electrofusion or by fusion, for example, contacting the donor cell and the enucleated recipient cell in the presence of a fusogenic agent, for example, an inactivated alphavirus, such as Sendai virus or a chemical agent such as polyethylene glycol.

One advantage of the present methods is that the development of nuclear transfer embryos from ES cells allows in vitro development of the nuclear transfer embryos to the compact morula stage, and implantation of these into surrogate mothers results in live birth. Another advantage is that the methods of the present invention allow the analysis or characterization of the genetically modified nuclear donor ES cell or of a nuclear donor ES cell of a genetic makeup of interest prior to the creation of the nuclear transfer embryo, thus allowing greater economy of effort and improved success in the production of the designed animal of interest. The present methods also allow the production of relatively large numbers of genetically identical animals due to the ability to propagate the genetically modified or other ES cells prior to nuclear transfer and embryo formation.

The present invention further provides cultured non-human embryos and animals of interest and progeny thereof (where those progeny animals exhibit the genotype and/or phenotype or nucleic acid sequences of interest) produced by the methods described herein. Where the non-human transgenic animal is a pig, the donor nucleus or the recipient (enucleated cell) can be from an animal which is a Meishan, Yorkshire, Duroc, Yorkshire×Duroc, Duroc×Yorkshire, Pietrain×Meishan or a Duroc×Meishan animal.

Where introduction of heterologous nucleic acid sequences is desired, any of a number of art known techniques and vectors can be employed. See, e.g., U.S. Pat. Nos. 6,258,998 and 6,011,197 and references cited in those patents, as well as a number of readily accessible scientific references for vectors, transformation and transfection methods, and sequences advantageously introduced into transgenic animals. ES cells, especially porcine ES cells, can be prepared as described in U.S. Pat. No. 5,523,226. See also U.S. 2003/0070186 A1.

To produce transgenic swine, embryonic stem (ES) cells are isolated from a porcine blastocyst approximately 7 to 8 days post-fertilization. Once isolated, the ES cells are transformed with 'foreign' (heterologous) DNA, if desired. Individual colonies are screened for integration by the polymerase chain reaction (PCR), screened for expression using a marker gene such as β-galactosidase or by assay of the specific gene product.

After the desired ES cell colonies are identified, they can be grown to produce many cells containing the transgene. The transformed or other ES cells may then be used to produce chimeras or in nuclear transfer programs to produce genetically identical swine.

BRIEF DESCRIPTION OF THE DRAWINGS

FIGS. 11A-11C are photomicrographs depicting a control blastocyst (FIG. 11A) and nuclear transfer blastocyst (FIG.

Figure 11C:
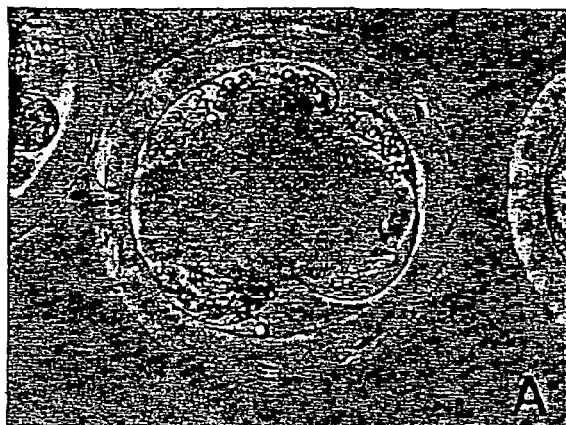

11B) at higher and lower magnifications (FIG. 11C). The nuclear transfer blastocyst was produced with an enucleated zygote.

Figure 12:
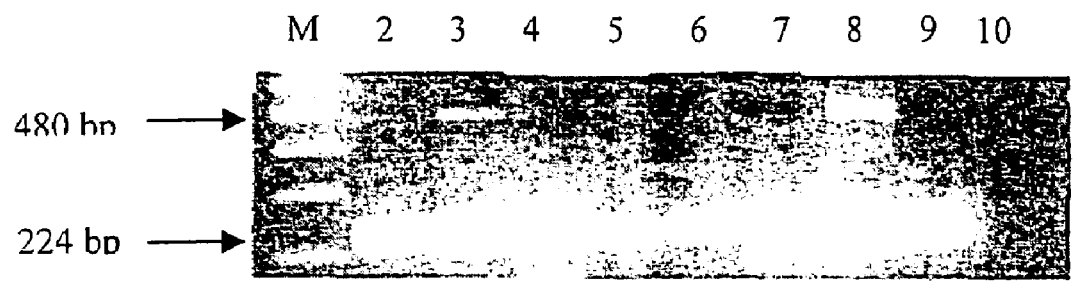

FIG. 12 is a photograph of an ethidium bromide-stained 2% agarose gel six NT embryos' nucleic acids that were amplified by PCR using the S014F, S0141RE, 1160 and 1630 primers. Lane 1 is a PCR size marker. Lanes 3 and 5 have the 480 bp band indicating an embryo that is positive for α-lactalbumin. Lanes 2, 4, 5, 6 and 7 have only a 224 bp band indicating they are negative for the α-lactalbumin gene. Lanes 8 and 9 are controls for the α-lactalbumin gene (positive or negative, respectively). Lane 10 contained no DNA template.

Figure 13:
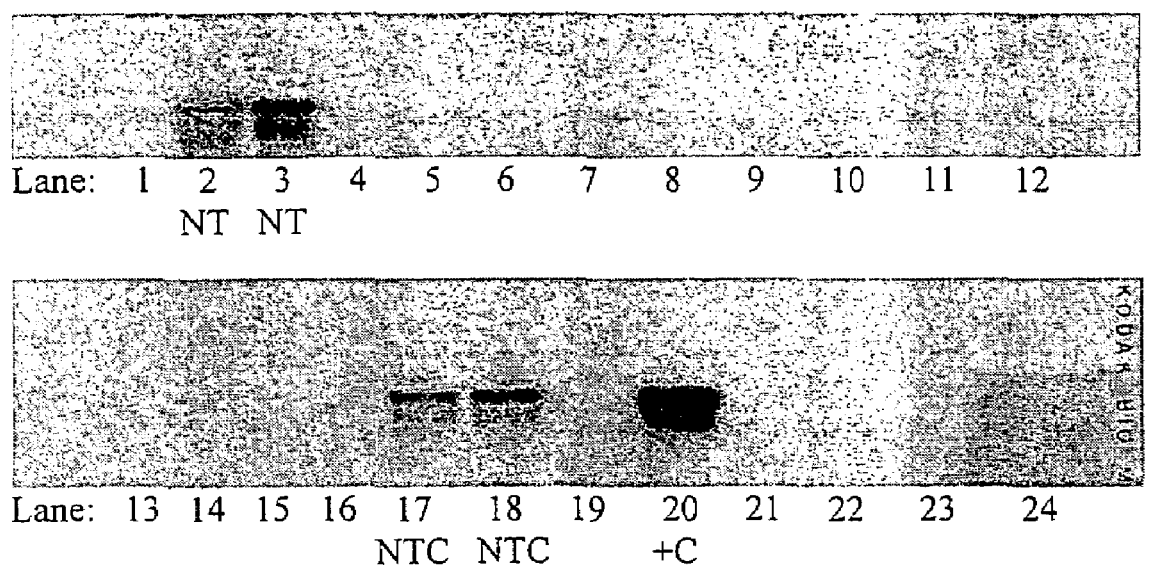

FIG. 13 is a photograph of a Southern blot with DIG labeled α-lactalbumin probe (480 bp) that was exposed to x-ray film for 50 seconds and developed. Lanes 2 and 3 show NT embryos that are positive for α-lactalbumin. Lanes 17 and 18 show nuclear transfer control (NTC) embryos that are positive for α-lactalbumin. Lane 20 is a positive control, α-lactalbumin cDNA transferred and probed. This blot was then stripped and reprobed using a probe for a microsatellite marker of porcine genomic DNA (data not shown).

DETAILED DESCRIPTION OF THE INVENTION

Oogenesis begins with the formation of primordial germ cells (PGC's) which are the only source of adult germ cells. Primordial germ cells arise in the extra-embryonic tissues of the yolk sac and allantois, migrate into the hindgut epithelium and along the dorsal mesentary of the genital ridges and finally arrive in the primitive gonad (Wassarman and Albertini, 1994). The PGC's undergo approximately 7 to 8 mitotic divisions during migration until 2 to 3 d after arrival in the ovary and are converted to oogonia which are connected by intercellular bridges (cell syncytium) and actively dividing (Wassarman and Albertini, 1994). Oogonia become oocytes once they cease mitosis and enter meiosis. Meiosis continues until oocytes reach the dictyate stage of the first meiotic prophase which is at or shortly after parturition in most species. During this stage, oocytes will undergo a period of extensive growth and discontinue meiosis until the gonadotropin surge at ovulation. It is here that meiosis resumes and continues until oocytes are arrested at metaphase II (unfertilized oocytes). Meiotic reduction also begins as evidenced by first polar body extrusion. Oocytes will then remain at this stage until fertilization or parthenogenetic activation at which time meiosis is completed and the second polar body is extruded (Wassarman and Albertini, 1994).

The most dramatic aspect of oocyte growth is the 300-fold increase in size to become one of the largest cells in the body. During oocyte growth, some distinct structural changes occur. These include an increase in the diameter of the nucleus (or germinal vesicle; GV) as well as a marked decrease in the nuclear to cytoplasm ratio, enlargement and a change from a diffuse, granular to a dense, fibrillar network of nucleoli, increase in the number of mitochondria as well as a change from elongated mitochondria with transverse cristae to round mitochondria with columnar cristae, a change in Golgi membranes from flat stacks of arched lamellae with no vacuoles to swollen stacks of lamellae with many vacuoles, appearance of cortical granules, appearance and growth of the zona pellucida, increase in the number of ribosomes, and appearance of cytoplasmic lattices.

Biochemical changes also occur during oocyte growth. An extremely large amount of total ribonucleic acid (RNA; 200-fold levels in somatic cells; and protein (50-fold levels in somatic cells) synthesis and storage is present in growing murine oocytes. These accumulate primarily because cytokinesis does not occur, although the concentration of total RNA and protein are not different from somatic cells. Some specific proteins that are synthesized during murine oocyte growth are mitochondrial and ribosomal proteins, zona pellucida glycoproteins, histones, tubulin, actin, calmodulin, lactate dehydrogenase, creatine kinase and glucose-6-phosphate dehydrogenase. Changes in specific gene expression during oocyte growth have been reported for murine oocytes. These include presence of oct-3 messenger RNA (mRNA) in growing oocytes, an increase in number of c-kit transcripts, increase in transcription of m-ZP3 and unusually high levels of lactate dehydrogenase activity in oocytes prior to meiotic maturation as well as numerous others.

Meiotic maturation is defined as the progression from the dictyate stage of the first meiotic 0prophase to metaphase II. Oocytes acquire meiotic competence by obtaining the ability to progress from GV breakdown to metaphase I and then obtaining the ability to progress from metaphase I to metaphase II. Porcine oocytes from follicles with an average diameter of 3 mm have attained meiotic competence (Szollosi, 1993). Meiotic maturation is composed of a number of structural changes. Probably the most obvious structural change is GV (or nuclear) breakdown. This is very evident in murine oocytes; however, this can only be seen via a nuclear stain in porcine oocytes. The next sequence of landmarks include chromosome condensation (transition from diffuse dictyate-stage to V-shaped, telocentric bivalent chromosomes), spindle formation and first polar body extrusion. Throughout these events, a number of alterations in microtubule and microfilament structure occur. Other biochemical changes occur during meiotic maturation including a dramatic decrease in RNA levels, a decrease in intracellular methionine levels and a decrease in protein synthesis.

Certain regulatory molecules are also involved in meiotic maturation. Factors suggested to inhibit GV breakdown are cyclic adenosine monophosphate and regulators of its intracellular levels, calcium, calmodulin, steroids, gonadotropins, purines, protein inhibitors and intercellular communication between cumulus cells and the oocyte. Two hypotheses for the resumption of meiosis by luteinizing hormone (LH) at ovulation are loss of inhibitory input and positive stimuli (Downs, 1993). The loss of inhibitory input hypothesis suggests that inhibitory substances (e.g., cyclic adenosine monophosphate) produced by granulosa or cumulus cells maintain meiotic arrest and the LH surge may terminate communication between the follicle granulosa cells and cumulus cells or between cumulus cells and the oocyte resulting in the absence of this inhibitory stimulus to the oocyte. The positive stimuli theory suggests that LH may induce production of a substance (calcium, adenosine triphosphate, pyruvate) from granulosa or cumulus cells that directly causes the oocyte to resume meiosis.

Dramatic decreases in tubulin, actin, histone, ribosomal protein, lactate dehydrogenase and zona pellucida glycoprotein synthesis rates occur as well as phosphorylation changes in cell cycle control proteins. Changes in specific gene expression during meiotic maturation have been reported for murine oocytes. These include a decrease in c-mos transcription between metaphase I and II, presence of oct-3 mRNA in ovulated oocytes, a dramatic drop in m-ZP3 RNA levels at ovulation, appearance of tissue-type plasminogen activator transcripts following GV breakdown and a sharp decrease in lactate dehydrogenase levels during meiotic maturation.

An important cytoplasmic factor involved in meiotic maturation is a protein called MPF. Maturation (M-phase, mitosis, meiosis) promoting factor is ubiquitous to all dividing yeast, invertebrate, amphibian and mammalian cells and it controls the transition from the G2 to mitosis phases of the cell cycle. Two subunits form the MPF complex including a 34 kilodalton (kD) catalytic subunit (p34cdc2; a protein kinase) and a 45 kD regulatory subunit (cyclin B). Levels of p34cdc2 are constant while cyclin levels fluctuate throughout the cell cycle. Immature oocytes contain a precursor to MPF which is the inactive form and dephosphorylation of p34cdc2 at tyrosine and threonine residues results in the active state of MPF, which is required for GV breakdown. At the end of metaphase I (prior to first polar body extrusion), the cyclins are degraded rendering the MPF complex inactive. New cyclins are synthesized and MPF becomes highly active during metaphase II. Levels of MPF remain high during metaphase II due to a protein called cytostatic factor (CSF). This protein contains products of the c-mos (pp39mos; a 39 kD phosphoprotein) and cdk-2 (cyclin-dependent kinase 2) genes and appears to act by preventing cyclin degradation. Upon oocyte activation, CSF is destroyed by a protease that is activated by the release of Ca2+ ions and MPF levels drop allowing meiosis completion and pronuclear formation. Examination of histone H1 kinase is used as a reflection of MPF activity because p34cdc2 has been shown to phosphorylate histone H1 in vitro. These phosphorylation events have been used as a biochemical assay for the estimation of p34cdc2 activity.

Successful oocyte development in vitro has become much more important in recent years with the advances in molecular biology and an increased push for the production of transgenic animals. The pig has lagged somewhat behind other species because IVM and in vitro fertilization (IVF) can only be accomplished with very limited success. Much of the problem lies in the high incidence of polyspermy that occurs with IVF in the pig. Therefore, the lack of success in this area has influenced investigators to avoid the previous steps (i.e., IVM). However, a significant amount of research is currently underway to improve IVM systems. To date, porcine IVM systems are successful in inducing nuclear maturation (approximately 90%); however, cytoplasmic maturation rates remain relatively low. Researchers have reported that porcine follicular fluid, follicular cells and hormonal supplements (primarily LH or equine chorionic gonadotropin, eCG) are beneficial to cytoplasmic maturation while fetal calf serum is not (Niwa, 1993). Further, glutathione content of oocytes has been associated with increased rates of cytoplasmic maturation and addition of cysteine to the culture medium increases glutathione content of oocytes (Niwa, 1993).

Because NT involves the activation of oocytes without binding of sperm, it is important to have a general knowledge of the events involved in fertilization. In mammalian systems, a complex series of events occurs beginning at fertilization and culminating in formation of the new zygote. In brief summary, membrane fusion occurs between the acrosome-reacted sperm and the mature, metaphase II oocyte. During the following 15 h in the pig, swelling of the sperm head, de-condensation of DNA, formation and migration of the male pronucleus, apposition of the male and female pronuclei, union of pronuclei (syngamy), and cleavage to the two-cell stage occur. Timing of these events in vivo has been studied (Laurincik et al., 1994b, 1995). Sperm head decondensation occurs by 40 h post-hCG; pronuclei are present 44 to 48 h post-hCG; opposed pronuclei are present 52 h post-hCG; DNA synthesis begins in the porcine zygote approximately 56 h post-hCG and lasts 4.5 to 7.5 h; and cleavage occurs 64 h post-hCG. These events all occur within the ampullar region of the oviduct in pigs. Investigation of events following IVF of in vivo matured and IVM porcine oocytes (Laurincik et al., 1994a) has revealed that sperm penetration begins after 4 and 6 h in in vivo and in vitro derived oocytes, respectively; sperm head decondensation occurred in 2 h for both groups; synchronized opposing pronuclei were present after 8 h in in vivo derived oocytes and after 14 h in IVM oocytes; syngamy begins 16 h after IVF for in vivo matured oocytes and 18 h after IVF for IVM oocytes; and cleavage occurred after 28 and 32 h for in vivo and in vitro derived oocytes, respectively.

The initial binding of the sperm to the egg results in recurrent waves of calcium into the oocyte which alter egg membrane potential. Early calcium transients are probably important for the exocytosis of cortical granules, block to polyspermy (Yanagimachi, 1994), activation and development of the oocyte, resumption of meiosis and second polar body formation, formation of pronuclei and regulation of the cytoskeletal systems involved in pronuclear migration and fusion.

Although little is known about the mechanisms of the block to polyspermy in mammals, it is known that the electrical (fast) block has not been evidenced in mice; the cortical granule envelope is formed from dispersion of cortical granule components into the perivitelline space following release of cortical granules by the oocyte; mucopolysaccharides, protease, tissue-type plasminogen activator with serine protease activity, acid phosphatase and peroxidase are released during cortical granule exocytosis; chemical interactions between these materials and molecules of the zona pellucida result in the zona reaction; and the plasma membrane block is independent of cortical granule exocytosis.

Decondensation of the sperm nucleus upon entry into the oocyte cytoplasm involves a number of events including: nuclear envelope disintegration, reduction of disulfide bonds of DNA-associated protamines by reduced glutathione, chromatin decondensation and replacement of sperm specific protamines by histones. Nucleoplasmin in the oocyte cytoplasm may bind to protamines following disulfide bond reduction leaving the DNA to bind to histones present in the cytoplasm.

DNA synthesis begins at approximately the same time in the male and female pronuclei. A number of mRNAs are translated at the pronuclear stage. Post-translational modifications of proteins within the oocyte following fertilization have been reported in the mouse, rabbit, sheep and pig.

Alterations in the cytoskeleton influence the remaining events up to and including cleavage. Microfilaments are responsible for anchoring the meiotic spindle to the egg cortex, determining the axis of cell division and drawing the sperm nucleus deep within the oocyte, whereas microtubules are responsible for cell division, pronuclear formation and pronuclear migration. In the mouse, microtubules are formed from centrosomes already present in the oocyte whereas the sperm centrosome form microtubules in sheep and rabbits. Kim et al. (1996a) reported that the latter is the case in porcine oocytes and that the functional centrosome is composed of both maternal and paternal centrosomal components. In mammals, fusion of pronuclei does not occur at syngamy. Instead, the pronuclei become apposed, the pronuclear membranes breakdown, and chromosomes intermix and align at the metaphase plate prior to cleavage.

Parthenotes are oocytes that are activated by methods (induced or spontaneous) other than fertilization. These methods mimic fertilization probably by triggering calcium waves throughout the oocyte. Further, these stimuli may cause translation of maternal mRNA's into proteins that are essential in the cleavage process. Parthenogenesis can occur in many ways and by many different activation methods that will be discussed in detail later. In most animals, including mammals, parthenotes will not develop to term. Defects in cytoskeletal structure are not responsible for developmental incompetence of parthenotes despite an absence of the sperm components. In the pig, the maternal centrosomal material is present in the oocyte as undetectable material but can form a dense network of microtubules within the cytoplasm after parthenogenetic activation (Kim et al., 1996a). Bovine (Navara et al., 1994) and rabbit (Pinto-Correia et al., 1993) parthenotes form bipolar spindles and divide normally. However, aged oocytes have disrupted microfilaments which hinders development following parthenogenetic activation (Kim et al., 1996c). This is important since aged oocytes are commonly used as cytoplasts in bovine NT.

In occidental breeds or pigs, the one-, two- and four-cell embryo stages occur between 0 and 15, 15 and 22, and 22 and 42 h after fertilization, respectively. During the four-cell stage, embryos move through the utero-tubular junction and enter the uterine horns. By 5 d after the onset of estrus (d 0), embryo development has reached the morula stage. Morula stage embryos undergo compaction and cells begin to secrete fluid and rearrange to form the blastocoele. The blastocoele is a central fluid-filled cavity and it first appearance marks the blastocyst stage (d 6). At this stage, blastomeres start to form the ICM and trophectoderm. The expanded blastocysts hatch from the zona pellucida 7 d after the onset of estrus. Hatched blastocysts undergo an extensive transition from spherical to filamentous over the next 6 d resulting in the beginning of implantation of the uterus on d 13. Implantation is completed between 18 and 24 d after the onset of estrus. Meishan embryo developmental events occur approximately 12 h later relative to the onset of estrus than those in occidental breeds, primarily because ovulation occurs approximately 12 h later in Meishan gilts.

In vitro, the two-cell stage lasts approximately 14 h (Prather, 1993; Prather et al., 1996) and the four-cell stage lasts 50 h (Schoenbeck et al., 1993), in vitro. The four-cell stage is extremely long because this is when the transition from the maternal to zygotic genome occurs. If the correct components are not present in the culture medium, embryos stop development at this stage, causing some difficulty in the culture of early stage porcine embryos. In order to complete the NT experiments, it was important to have an efficient culture system to facilitate development of NT embryos.

Porcine embryos have been cultured in vivo by a number of methods (Petters and Wells, 1993). Immature mouse oviducts will support development of morula and blastocyst stage embryos but one-cell embryos could not develop past the four-cell stage (Ebert and Papaioannou, 1989). Hermann and Holtz (1985) reported successful culture of one-cell embryos past the four-cell stage in rabbit oviducts but development was hindered if culture was longer than 24 h. Early porcine embryos can be cultured to blastocysts in anestrous sheep oviducts with similar rates to many defined media (Prather et al., 1991b). Finally, the porcine oviduct was reported to support development of early embryos only to the morula stage. In addition to in vivo methods, zygotes develop to the blastocyst stage in mouse oviducts in organ culture (Krisher et al., 1989) and when co-cultured with oviductal cells (Allen and Wright, 1984; White et al., 1989).

Porcine embryo culture has been successful in a variety of simple, defined media (Petters and Wells, 1993). Generally, investigators have attempted to obtain a medium that will support development throughout all stages of in vitro culture. However, dynamic culture systems are believed to mimic in vivo conditions. Most culture media are very similar and originate from those first defined for murine embryo culture (Whitten and Biggers, 1968). Some components of these media have been shown to profoundly affect pig embryo development. Glucose has been reported to be both stimulatory (Beckmann and Day, 1993) and inhibitory (Youngs et al., 1993) to early embryo development whereas lactate is inhibitory (Davis and Day, 1978; Davis, 1985). Further, the combination of glucose and lactate are inhibitory to development of murine and porcine embryos (Petters and Wells, 1993). It has been shown that glutamine can be used instead of glucose, pyruvate and lactate successfully (Petters and Wells, 1993).

Robl and Davis (1981) originally reported the beneficial effect of serum on morula and blastocyst development, especially on hatching from the zona pellucida. However, early stage embryos are cultured with bovine serum albumin (BSA) instead of serum (Petters and Wells, 1993). It has been reported that different BSA lots had an effect on blastocyst development of bovine (Rorie et al., 1994), ovine (Batt and Miller, 1988), caprine (Batt et al., 1991) and rabbit (Kane, 1983) embryos. It was suggested that the differences in citrate levels of BSA lots might be important to embryo development. Also, improved development of one-cell embryos to blastocysts has been reported with the addition of oviductal fluid to the culture medium (Archibong et al., 1989). Glutamine, sorbitol, taurine and hypotaurine can be added to culture media to improve embryo development (Petters and Wells, 1993).

The maternal to zygotic genome transition is the period when the embryonic genome begins transcribing mRNA rather than utilizing stored maternal mRNA in the cytoplasm. Mature oocytes contain all the machinery necessary to continue development to the four-cell stage, although activation may or may not occur. This transition is important, not only to in vivo produced embryos but also in NT embryos. With NT, some species (mouse, rat, pig) only produce live young if karyoplasts are isolated from embryos that are still controlled by the maternal genome or within a few cell cycles of these stages. In mice, the maternal to zygotic transition occurs at the two-cell stage and low rates of development have been reported when karyoplasts of late two-cell or more advanced stages are used for NT. The cause is probably not inhibitory factors in the advanced nuclei but failure of these nuclei to support development upon NT (Solter et al., 1985). Nuclei from these advanced stages still produce two-cell stage-specific genes following transfer into enucleated zygotes and overnight culture (Latham et al., 1991). Therefore, irreversible gene inactivation is probably not responsible for lower rates of development in NT embryos derived from advanced stages. An improper interaction between the nucleus and cytoplasm may be the primary reason for failure of advanced nuclei to support development (Kwon and Kono, 1996). Further, the only live pig produced by NT was completed with a blastomere at initiation of the embryonic genome (four-cell stage; Prather et al., 1989). Porcine embryos have a distinct maternal to zygotic transition at the four-cell stage (Jarrell et al., 1991). In some other species, such as cattle and sheep, the transition from maternal to embryonic control occurs gradually (eight- to 16-cell stage). Nuclear transfer experiments have been much more successful in these species especially when karyoplasts from later developmental stages are examined. It is possible that the gradual transition may allow more time (i.e., two cell cycles instead of one cell cycle) for karyoplast-cytoplast cell cycle coordination before activation embryonic genome.

An alteration of the cell cycle during the maternal to embryonic transition has been reported. The cell cycle of two-cell embryos is primarily S-phase whereas four-cell embryos is composed of a 2 h G1 phase, 16-18 h S-phase and 34 h G2 phase (Prather, 1993). The G2 stage is probably extended due to culture conditions since murine embryo culture conditions have been shown to lengthen the G2 stage and not effect the S-phase (Smith and Johnson, 1986; Prather, 1993). These results are believed important when comparing NT with ES cells to that of blastomeres. Especially, since the only pig produced by NT was produced with a four-cell karyoplast. It is possible that NT with porcine ES cells are entirely different from that with porcine blastomeres.

There is mRNA carry-over from the donor blastomere up to 12 h after NT (Parry and Prather, 1995). A number of proteins have been analyzed in murine preimplantation embryo development. Changes in metabolism, precursor transport, enzymes, protein synthesis and RNA synthesis as well as chemical changes, intermediary metabolite changes and nucleotide changes have been well established in murine preimplantation development. The main proteins synthesized prior to implantation include phosphoproteins, heat shock proteins, nuclear lamins, laminin, uvomorulin gap junctions and Na/K adenosine triphosphatase (Menezo and Renard, 1993). A number of growth factor genes are differentially expressed in the mammalian embryos (see Schultz and Heyner, 1993 and Watson et al., 1994 for reviews). However, little evidence exists as to the differential expression of these genes in early preimplantation porcine embryos. Epidermal growth factor transcripts are present in unfertilized oocytes whereas transcripts for transforming growth factor-a and the epidermal growth factor receptor are not (Vaughan et al., 1992). Genes for epidermal growth factor receptor are expressed by d 7 following onset of estrus, transcripts for transforming growth factor-a are present on d 8 but not at d 7, and epidermal growth factor transcripts are not present on d 7 to 12 (Vaughan et al., 1992). Insulin-like growth factor-I receptors are not present on d 4, 6, 8 or 10 porcine embryos whereas insulin-like growth factor-II receptors are present on all four d (Chastant et al., 1994).

The first differentiation event of early embryo development occurs when embryonic cells form the ICM and trophectoderm following compaction. Cells of the ICM form the fetus proper whereas cells of the trophectoderm form the placenta. Tarkowski and Wrobleska (1967) originally proposed that the inner cells of murine morula formed the ICM and outer cells formed the trophectoderm (inside-outside hypothesis). Polarization of the surface and cytoplasm of blastomeres begins at the eight-cell stage (Ziomek, 1987) and results in non-polar inner cells and polar outer cells at the 16-cell stage (Johnson and Ziomek, 1981). The inner cells form the ICM and the outer cells form the trophectoderm. Further, polarity of early stage blastomeres has been studied in other species (Koyama et al., 1994).

Prior to the isolation of ES cells, some studies were performed with embryonic carcinoma (EC) cell lines. Embryonic carcinoma cells are isolated from terminally-differentiated, spontaneous tumors (teratocarcinomas) that were induced by injection of embryos into the testis or under the kidney capsule (Anderson, 1992). Embryonic carcinoma cells resemble ES cells in that they are small (approximately 14 μm in diameter), round, grow rapidly in culture, have a high nuclear to cytoplasmic ratio, form tight, rounded colonies that become progressively larger and form embryoid bodies in culture. Embryonic carcinoma cells differentiate in vivo or in vitro (Anderson, 1992) and have the ability to form all three germ layers (ectoderm, endoderm and mesoderm). Chimeric mice have been produced by injection of EC cells into blastocysts and these cells can colonize the germ cells (Bradley et al., 1984). However, the participation of EC cells in germ cell formation is much lower than with ES cells (Pedersen, 1994).

Embryonic stem cells are very similar to EC cells. Embryonic stem cells are derived from the ICM of blastocysts (Evans and Kauffman, 1981; Martin, 1981; Bradley et al., 1984; Doetschmann et al., 1985). These cells can be grown in vitro for many generations providing an unlimited number of genetically identical cells that can differentiate into any tissue type or produce chimeras upon blastocyst injection (Wobus et al., 1984; Wheeler, 1994). ES cells can be electroporated with DNA to introduce (Gossler et al., 1986; Robertson et al., 1986) or even replace (Thomas and Capecchi, 1987; Capecchi, 1989; Robertson, 1991) or inactivate genes of interest. These ES cells can be screened, in vitro, for incorporation of the gene in the appropriate location within the genome before use in NT or chimera production. Pluripotent ES cells were isolated from mouse (Evans and Kauffman, 1981; Martin, 1981), embryos of rats (Iannaccone et al., 1994), pigs (Wheeler, 1994; Wheeler et al., 1997) and rabbits (Moreadith and Graves, 1992; Graves and Moreadith, 1993; Schoonjans et al., 1996), as evidenced by the production of coat-color chimeric animals. ES-like cell lines have been reported in cows (Saito et al., 1992; Strelchenko and Stice, 1994; Strelchenko, 1996), hamsters (Doetschman et al., 1988), mink (Sukoyan et al., 1992, 1993), pigs (Notarianni et al., 1990, 1991; Piedrahita et al., 1990a,b) and sheep (Handyside et al., 1987; Piedrahita et al., 1990b; Notarianni et al., 1991). Germline chimeric fetuses have also been reported from a transgenic bovine ES-like cell line (Cibelli et al., 1997), but coat-color chimerism was not reported, and the fetuses did not develop to term.

The ability of ES cells to be maintained in an undifferentiated state during culture has allowed research into cell differentiation as well as a host of other areas of scientific study. Mouse ES cells have been used as in vitro models for numerous developmental studies. Further research opportunities exist for study of embryos, fetuses and live animals that are produced from production of chimeric animals, including cell fate and interaction between genotypically different cells in close proximity to one another as only found in tumors and cancers.

Pluripotency is the ability of cells to form more than one tissue type. This can be accomplished for ES cells in a number of ways which include: treatment of ES cells in vitro with substances (e.g., retinoic acid) causing differentiation; injection of ES cells into the testis or under the kidney capsule of animals to produce tumors that, in turn, contain a number of tissue types produced by the ES cells; and use of ES cells to produce chimeric animals. Germ-line transmission of the ES cell genome has been accomplished in mice (Bradley et al., 1984; Evans, 1987; Zilstra et al., 1989). First, one can determine if colonization of the germ-line by the ES cells occurs using coat-color as a marker. Next, chimeric animals can be mated to determine if animals can be produced from germ cells of both phenotypes (Gilbert, 1994). Transgenic animals can be produced through alteration of the ES cell genome (Wheeler, 1994). All of the above mentioned steps to characterize ES cells, with the exception of production of a germ-line chimera, have been accomplished with porcine ES cells (Wheeler, 1994; Gerfen and Wheeler, 1995; Wheeler et al., 1997). Porcine ICM cells have been used to produce chimeric pigs (Kashiwazaki et al., 1992; Anderson et al., 1994), and the cells were incorporated into the germ-line cells (Anderson et al., 1994). In addition, there is DNA evidence of the participation of ES cells in formation of the germ-line (i.e., ovary, testis and sperm) of chimeric pigs.

Some investigators have produced live mice from pluripotent ES cell origin through methods other than production of chimeric mice. One method was aggregation of ES cells with "carrier" tetraploid four-cell embryos (chimeric cloning; Nagy et al., 1990, 1993). The carrier embryos can differentiate into extra-embryonic tissues but seldom into embryonic tissues whereas the ES cells differentiate into the fetus proper but are deficient in extra-embryonic tissue differentiation. The combination of these events allowed development to term. Blastocyst development from aggregation of tetraploid embryos and ICM cells suggest that this method may be possible in pigs (Prather et al., 1996). Another method was replacement of the ICM from blastocysts with ES cells (Modlinski et al., 1996). Two live mice derived from the ES cell line were born by this method, but both died within 10 d after birth. Although these methods showed production of the fetus proper from cell lines, totipotency was not confirmed because these cells could not differentiate to produce all the extra-embryonic tissues essential for birth of live young.

A chimera is an individual consisting of tissues of two or more genetic constitutions. Chimeric animals can be produced by combining ES cells (or other pluripotent cells) with embryos via aggregation (Bradley, 1987; Wood et al., 1993a), co-culture (Wood et al., 1993b), and morula (Lallemand and Brulet, 1990) or blastocyst (Gardner, 1968; Bradley et al., 1984) injection and subsequent transfer to recipient animals. Embryonic stem cells may incorporate into the ICM and aid in the formation of numerous tissues, producing a chimeric animal.

Figure 1:
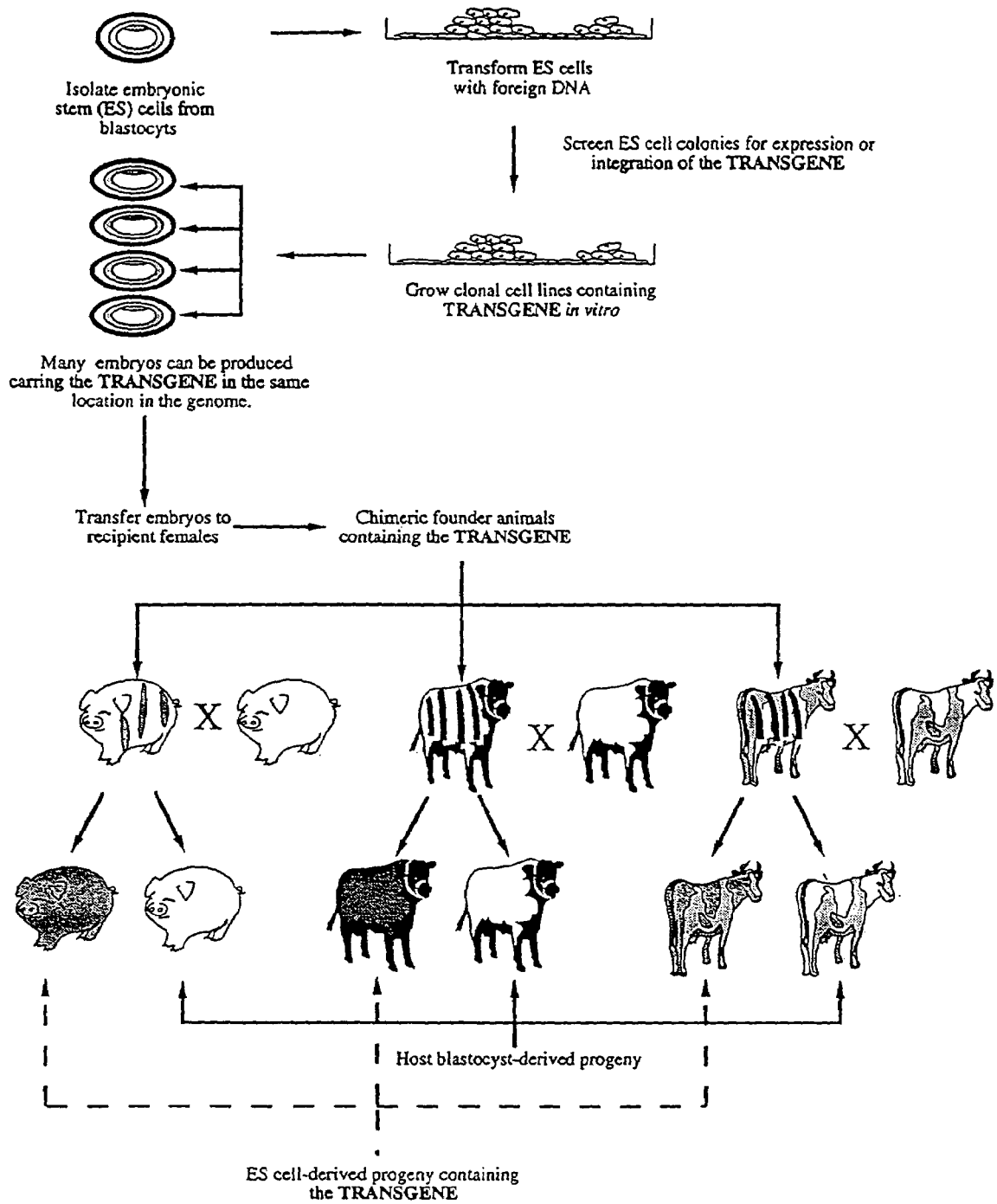
FIG. 1 summarizes the development of embryonic stem (ES) cells from embryos. ES cells are derived, cultured in vitro, transformed with exogenous DNA, screened for the presence of the TRANSGENE and re-introduced into blastocysts via microinjection. 'Chimeric' embryos are transferred into recipient females and offspring are carried to term. After birth, potentially chimeric offspring are screened for the presence of the transgene or other nucleic acid sequence of interest. Chimeras are bred, and if some of the gametes were derived from ES cells, then a portion of the offspring will be transgenic. From Wheeler et al. (1995).

Coat-color chimerism has been generally associated with a relatively high percentage of chimerism in the germ-line. In mice, ES cell selection criteria include coat-color chimeras in 50% or more of animals born with the majority able to express the ES cell genotype through the germ-line (Stewart, 1993). Coat-color chimeras have been produced in mice (Robertson, 1987), rats (Iannaccone et al., 1994), pigs (Wheeler et al., 1995, 1997) and rabbits (Schoonjans et al., 1996) by injection of ES cells into blastocysts and subsequent transfer to recipients. A germ-line chimera (colonization of the germ-line by ES cells) can be mated to produce transgenic animals (FIG. 1). This has been routinely accomplished in the mouse (Bradley et al., 1984), however, this has not been reported in rats, pigs or rabbits. Recently, investigators have reported the production of germ-line chimeric bovine fetuses from transgenic ES-like cells (Cibelli et al., 1997). However, coat-color chimerism was not determined, the ES-like cells were not characterized and a live animal was not produced. Furthermore, the production of transgenic animals from germ-line chimeras does not prove the totipotency of ES cells because there is no evidence that the ES cells formed every tissue in the body.

Totipotency of ES cells is established when ES cells can form every tissue of a live animal, including the germ-line. The only true method is to perform NT with one ES cell and produce a live animal. Therefore, the ES cell would contain all the necessary components to produce every tissue of a live animal. This has been attempted in the mouse (Tsunoda and Kato, 1993) and rabbit (Du et al., 1995a), but no live young were produced. Further, NT experiments with EC cells have failed to produce live young (Modlinski et al., 1990). This remains as the final step, following pluripotency evidence (Wheeler et al., 1997), in the determination of totipotency for porcine ES cells. Studies by Campbell et al. (1996a) and Wilmut et al. (1997) have proven that NT with totipotent cell lines can be successful.

Nuclear transfer was not reported in mammals for quite some time after studies in amphibians (McGrath and Solter, 1983a,b). Successful NT experiments (birth of live young) have been completed in mice (McGrath and Solter, 1983a,b; Robl et al., 1986), rats (Kono et al., 1988), rabbits (Stice and Robl, 1988), pigs (Prather et al., 1989), cattle (Robl et al., 1987; Prather et al., 1987), sheep (Willadsen, 1986; Smith and Wilmut, 1989) and goats (Yong et al., 1991). These studies all utilized blastomeres from early embryonic stages as karyoplasts. Porcine NT using blastomeres as karyoplasts has only produced one live pig (Prather et al., 1989) but this is not believed to have been repeated. Nevertheless, pronuclear exchange methods have been successful in the production of live pigs (Prather et al., 1989) indicating that the difficulties with NT are not due to the technique itself. Limited blastocyst development was also reported with two-, four- and eight-cell donor nuclei transferred into enucleated, metaphase II oocytes produced from an IVM system (Terlouw et al., 1992; Hyttel et al., 1993).

Without wishing to be bound by theory, difficulties with NT experiments in mice and pigs are believed to be due to the distinct maternal to zygotic transition. In the mouse, enucleated zygotes were originally used as cytoplasts (McGrath and Solter, 1983a,b). With this method, live young could only be produced when early two-cell blastomeres were used as karyoplasts (McGrath and Solter, 1984; Robl et al., 1986). However, when enucleated, two-cell embryos were used as cytoplasts, four- and eight-cell blastomeres were reported to direct development of blastocysts (Robl et al., 1986; Howlett et al., 1987; Kono and Tsunoda, 1989) and live mice (Tsunoda et al., 1987; Kono et al., 1991a). It was suggested that the difference in developmental stage between the karyoplast and cytoplast was limited to only two cell cycles (Barnes et al., 1987; Smith and Wilmut, 1990). Therefore, when eight-cell karyoplasts were used, enucleated two-cell cytoplasm could direct normal development whereas enucleated zygotes could not. Further, a key cytoplasmic component may be present following the maternal to zygotic transition that is more appropriate for eight-cell karyoplasts. Also, the use of zygotes enucleated at later stages following fertilization improved in vitro developmental rates (Smith et al., 1988, 1990; Cheong and Kanagawa, 1993). No reports using enucleated zygotes or two-cell embryos are believed to exist for porcine NT.

Following successful development of live young using enucleated, metaphase II oocytes as cytoplasts in other species (Willadsen, 1986; Robl et al., 1987; Stice and Robl, 1988; Prather et al., 1989), enucleated oocytes were used in the production of live mice from two- (Kono et al., 1991b; Cheong et al., 1992; Kono et al., 1992), four- and eight-cell (Cheong et al., 1993) karyoplasts. Kwon and Kono (1996) reported improved developmental rates of NT embryos with four-cell blastomeres as karyoplasts following serial NT. Blastomeres (synchronized in metaphase) were fused with enucleated, metaphase II oocytes and these complexes are cultured for 6 h in cytochalasin B to prevent cytokinesis. Next, the nuclei from the first NT were removed and each was fused with an enucleated zygote.

Inner cell mass cells are isolated from the ICM of blastocysts and are very similar in size to ES cells (15 to 25 mm diameter). Therefore, NT studies with ICM cells may provide a benchmark for NT studies with ES cells. Successful NT results with ICM cells were reported in mice (Illmensee and Hoppe, 1981), however, numerous conflicting results have been reported suggesting that the first study was flawed (McGrath and Solter, 1984; Tsunoda et al., 1987; Kono et al., 1991b). Live young have been born from NT with ICM cells in sheep (Smith and Wilmut, 1989) and cattle (Simms and First, 1993; Collas and Barnes, 1994; Keefer et al., 1994), including cultured ICM cells (Simms and First, 1993; Campbell et al., 1996a) and an ovine, embryo-derived cell line cultured up to 13 passages (Campbell et al., 1996a). Further, blastocyst development has been reported from NT embryos reconstructed with ICM cells in mice (Tsunoda et al., 1987; Kono et al., 1991b) and rabbits (Collas and Robl, 1991a). Presently, NT experiments are believed not to have been carried out with porcine ICM cells.

Primordial germ cells are the sole source of adult germ cells and are very similar in size to ES cells. Nuclear transfer with PGC's has produced live frogs (Smith, 1965) and salamanders (LeSimple et al., 1987). However, no live mammals have been produced from NT with PGC's. Male PGC's have been used as karyoplasts in murine (Tsunoda et al., 1989, 1992) and bovine NT (Delhaise et al., 1995). Results from these studies indicate very low rates of blastocyst formation (<20%). Recently, others have reported limited blastocyst development (9 to 13%) from NT with bovine oogonia as karyoplasts (Lavoir et al., 1997). Also, fresh or cultured PGC's from rabbit fetuses produced a low percentage of blastocysts following NT (Moens et al., 1995, 1996b) and low levels of chimerism following blastocyst injections (Moens et al., 1996a).

Nuclear transfer with ES cells as karyoplasts has been reported in mice (Tsunoda and Kato, 1993; Modlinski et al., 1996) and rabbits (Du et al., 1995a). Although blastocyst development was obtained, no live young were born. Modlinski et al. (1996) reported development to implantation when oocytes were used as cytoplasts and development to 16 d of gestation when two-cell embryos were used as cytoplasts. This fetus was derived from the ES cell line, as confirmed by eye pigmentation. Similarly, NT experiments with cells very similar to ES cells, EC cells, have produced some morula and blastocyst development but no live mice (Modlinski et al., 1990). There is little literature available regarding NT with ES cells. Stice et al. (1996) reported fetal development to 55 d of gestation for NT embryos produced from pluripotent embryonic cell lines. Interestingly, analysis of these fetuses revealed the absence of cotyledons and a hemorrhagic response in the caruncles. Therefore, the totipotency of these cell lines remains to be confirmed.

Campbell et al. (1996a) reported live lambs from NT with an established, cultured cell line derived from embryos. However, this line was differentiated, as indicated by cytokeratin and nuclear lamin A/C expression and the pluripotent nature of this cell line was not characterized in vitro. A study by Wilmut et al. (1997) showed that live sheep can be produced from NT with somatic cells as karyoplasts, using three different cell lines: 9 d embryo, 26 d fetus and the mammary gland of an adult ewe. All of the cell lines were differentiated and produced live lambs. However, DNA transfection of these cell lines has not been reported.

It has been reported that nuclear transplantation of karyoplasts into enucleated, metaphase II oocytes induces nuclear remodeling and reprogramming (Prather and First, 1990). The nucleus of a karyoplast from a later developmental stage is induced by a cytoplast into which it is transferred to control development as if it were a nucleus from that stage. Evidence of remodeling and reprogramming includes nuclear swelling (Stice and Robl, 1988; Prather et al., 1990), growth of nucleoli (Collas and Robl, 1990), modification of nucleolar structure (Kanka et al.; 1991; Fulka et al, 1996; Ouhibi et al., 1996), blebbing of the nuclear envelope (Szollosi and Szollosi, 1988; Kanka et al., 1991), delay in time of blastocyst formation of NT embryos (Prather and First, 1986; Stice and Robl, 1988), decrease or cessation of RNA (Kanka et al., 1996; Ouhibi et al., 1996) and protein synthesis for first 24 h following fusion (Prather and Rickords, 1992; Hyttel et al., 1993; Parry and Prather, 1995), stage-specific protein synthesis (Latham et al., 1994; Chastant et al., 1996) and uptake of nuclear lamins (Prather et al., 1991a) in donor nuclei following fusion. In bovine NT embryos, reprogramming occurs gradually over two or three cell cycles (Kanka et al., 1991; King et al., 1996). Characteristic structural events include nuclear envelope breakdown (NEBD) and premature chromosome condensation (PCC; Prather et al., 1990).

Not until later were these structural changes (NEBD and PCC) correlated with events which occur in the cell cycles of somatic cells and it was determined that they were the result of karyoplast transfer into an environment with high levels of MPF (see Campbell et al., 1996b for review). Metaphase II oocytes have very high levels of MPF (Fulka et al., 1992; Campbell and Wilmut, 1994). Transfer of S-phase nuclei into this environment (Collas and Robl, 1991b) results in chromatin with a typical pulverized appearance (Schwartz et al., 1971); chromosomal abnormalities including fragmented chromatin, joined chromatin, and chromosomal breakage (Rao et al., 1977; Collas et al., 1992a); and defects in DNA synthesis, nucleolar activity and specific phosphorylation events (Pinto-Correia et al., 1995). Transfer of G1 and G2 nuclei results in elongated chromosomes with single- and double-stranded chromatids, respectively (Collas et al., 1992a; Campbell et al., 1996b). Campbell et al. (1993, 1994) reported that all nuclei transferred into metaphase II cytoplasts underwent NEBD and, in turn, DNA synthesis. This results in DNA replication of G1 nuclei, DNA re-replication of G2 nuclei and partial DNA re-replication of S-phase nuclei (FIG. 2; Campbell et al., 1993). Thus, ploidy problems can be expected in resultant cells from NT with G2 and S-phase nuclei but not with G1 nuclei (see Campbell et al. 1996b for review). In addition, Barnes et al. (1993) reported that transfer of donor nuclei into metaphase II cytoplasm resulted in interrupted DNA synthesis, mostly partial or complete NEBD and a larger number of NT embryos that were not diploid.

Upon oocyte activation, MPF levels drop to a basal level prior to pronuclear formation. Therefore, NEBD and PCC do not occur when oocytes are activated prior to fusion or when zygotes are used as cytoplasts (Campbell and Wilmut, 1994). In this case, DNA re-replication (G2 nuclei) and partial DNA re-replication (S-phase nuclei) do not occur (FIG. 2; Campbell et al., 1993). Therefore, the cell cycle stage of the karyoplasts should not hinder the ploidy of NT embryos. Early reports with thymocyte nuclei (Czolowska et al., 1984; Szollosi et al., 1988) and embryonic nuclei (Balakier and Masui, 1986; Czolowska et al., 1986) as karyoplasts indicated that NEBD and PCC only occurred when karyoplasts were fused at or within 30 min after activation of oocytes and that the nuclear envelope remained intact, although nuclear swelling occurred, when karyoplasts were fused later than 30 min following activation (Smith and Wilmut, 1990). Similarly, Barnes et al. (1993) reported that transfer of karyoplasts to S-phase cytoplasm resulted in uninterrupted DNA synthesis, only partial or no NEBD and a higher percentage of diploid NT embryos. Smith et al. (1996) determined that cessation of RNA synthesis after fusion was slower and resumption of RNA synthesis occurred sooner in NT embryos constructed with activated cytoplasts than those constructed with unactivated cytoplasts. In porcine NT, nuclear swelling (Stumpf et al., 1993b; Terlouw et al., 1993) occurred when fusion followed activation in IVM cytoplasts whereas PCC was dramatically less when fusion followed activation (73 vs 16%; Stumpf et al., 1993a). Further, aging of cytoplasts resulted in almost no PCC following NT when fusion occurred simultaneously or following activation (4 vs 0%). Similar aging results were reported for murine oocyte-blastomere hybrids that were fused at 20 or 24 h post-hCG (Prochazka and Fiser, 1995). These results suggest that the aging process in vitro induced activation. It should also be noted that NT embryos produced from activated oocytes organize metaphase spindles in a similar manner to parthenotes (Pinto-Correia et al., 1993). These small defects in the spindles indicate that problems in the formation of the mitotic apparatus in the first cell cycle may have cumulative effects on embryo development.

Much of the difficulty in NT lies in asynchrony between the karyoplast and cytoplast cell cycles and ploidy problems in the resultant cells (Campbell and Wilmut, 1997). Two approaches have been taken to alleviate this problem. First, the cell cycle of the karyoplasts can be synchronized to a specific stage that is most appropriate for the cytoplast that is utilized. Collas et al. (1992b) reported increased development of rabbit NT embryos produced with G1 karyoplasts than those produced with G1/S-phase nuclei. Also, Cheong et al. (1993) reported improved development of murine NT embryos with G1 karyoplasts over G2 and S-phase karyoplasts. Another method is to synchronize cytoplasts to a stage of the cell cycle that would be appropriate for karyoplasts at any stage of the cell cycle. In cattle (Campbell et al., 1996b) and sheep (Campbell et al., 1994) NT, upon transfer of S-phase karyoplasts improved embryo development was obtained with S-phase cytoplasts over metaphase II cytoplasts. In addition, Otaegui et al. (1994a) reported higher developmental rates of NT embryos constructed with G1 and early S-phase karyoplasts when S-phase cytoplasts instead of metaphase II cytoplasts. Using enucleated zygotes as cytoplasts in murine NT, the effect of karyoplast cell cycle stage on developmental rates has been studied (Smith et al., 1988, 1990; Cheong and Kanagawa, 1993). Further, effects of cell cycle stage have been reported for NT with enucleated oocytes as cytoplasts in mice (Kono et al., 1992; Cheong et al., 1993).

Researchers have used cells from later embryonic stages including inner cell mass (ICM) cells (Smith and Wilmut, 1989; Collas and Robl, 1991a; Sims and First, 1993) and ES cells (Tsunoda and Kato, 1993; Du et al., 1995a) as karyoplasts. Blastocyst development has been reported from NT with rabbit and mouse ES cells as karyoplasts, although no fetal development has been shown (Tsunoda and Kato, 1993; Du et al., 1995a). The prospect for success with these studies was greatly enhanced by the birth of live lambs from NT with an established, cultured embryonic cell line (Campbell et al., 1996a) as well as from a somatic cell of an adult animal (Wilmut et al., 1997). However, production of live animals following DNA transfection of these cells remains to be accomplished. Another difficulty exists with these studies in the pig because only one live piglet has been born via NT (Prather et al., 1989) with an early stage blastomere as the karyoplast. These results have yet to be repeated.

Part of the difficulty with NT procedures has been the synchronization of karyoplast and cytoplast (recipient cytoplasm) cell cycles. Two approaches may be undertaken to accomplish this goal. The first strategy involves the synchronization of karyoplasts at a certain stage of the cell cycle followed by fusion with cytoplasts at the same stage of the cell cycle. By this method, only karyoplasts from a specific cell cycle stage can be used. The second strategy involves activation of the cytoplasts to decrease maturation promoting factor (MPF) levels before fusion of karyoplasts with cytoplasts. Elevated levels of MPF in the cytoplasm result in DNA replication, DNA re-replication and partial DNA re-replication of G1, G2 and S-phase donor nuclei, respectively. However, basal levels of MPF would result in DNA replication, no DNA replication and continued DNA replication of G1, G2 and S-phase donor nuclei, respectively. In this case, karyoplasts from any stage of the cell cycle can be used and the ploidy of resultant cells is normal in every case (see Campbell et al. [1996b] for review). The second method was our choice for these studies because the cell cycle of the porcine ES cells used in this experiment has not been characterized and compounds to block the cell cycle may have been detrimental to the ES cells.

The primary goal of the research reported herein was to obtain in vitro embryo development of NT embryos produced with porcine ES cells as karyoplasts. Three methodologies were established to achieve this goal. The first was to develop an appropriate culture system to obtain development of one-cell porcine embryos to the blastocyst stage. Unlike bovine and ovine embryos, porcine embryos have a very distinct maternal to zygotic genome transition at the four-cell stage (Jarrell et al., 1991). Therefore, all the necessary components must be present in the medium to assure continuation of embryonic development. Considerable investigation into the culture of porcine embryos has been reported (Petters and Wells, 1993).

Second, an efficient method for activation of in vivo matured porcine oocytes was developed. Pronuclear stage cytoplasts needed to be obtained by this method without detriment to the viability of cytoplasts for NT embryo development. Mammalian oocytes have been activated by physical stimuli (e.g., micromanipulation; Markert, 1982), heating, cooling, electric pulses (Whittingham, 1980), aging (Ware et al., 1989) and a variety of chemical stimuli (Whittingham, 1980). Most of these methods have been attempted with porcine in vitro matured (IVM) oocytes, but these results may not be comparable those obtained using to in vivo matured oocytes. Artificial activation of IVM oocytes is influenced by the culture medium (Yamauchi et al., 1996). In addition, the quality of oocytes used as cytoplasts for NT experiments is extremely important (Fulka, Jr. et al., 1996). Differences between IVM and in vivo matured porcine oocytes could be due to different patterns of MPF levels during maturation (Naito et al., 1992).

Finally, we examined development of NT embryos produced with different stages of cytoplast (unactivated oocytes, activated oocytes and zygotes). Unlike zygotes from mice, zygotes from cattle, sheep and pigs must be manipulated to visualize pronuclei. Therefore, metaphase II oocytes have primarily been used as cytoplasts in these species. In addition, studies in cattle (Prather et al., 1987; Robl et al., 1987), mice (Cheong et al., 1993; McGrath and Solter, 1984) and rabbits (Modlinski and Smorag, 1991) suggest that oocytes are better cytoplasts than zygotes. Activation of cytoplasts prior to fusion has improved NT embryo development in cattle (Campbell et al., 1993), sheep (Campbell et al., 1994) and mice (Otaegui et al., 1994a).

Further, comparison of enucleated zygotes and activated, enucleated oocytes as cytoplasts did not reveal differences in bovine NT embryo development (Stice et al., 1994). Only unactivated, metaphase II oocytes have been used as cytoplasts in porcine NT whereas enucleated zygotes have been used as cytoplasts only in porcine pronuclear exchange (Prather et al., 1989). We also determined the appropriate stage of cytoplast for in vitro development of NT embryos beyond the four-cell stage.

Results across species indicate that karyoplasts in G1 or early S-phase of the cell cycle are most appropriate for transfer into enucleated, metaphase II oocytes. Therefore, use of enucleated, metaphase II oocytes would require the selection of G1 karyoplasts. Since the G1 stage of the cell cycle in blastomeres is extremely short and most blastomeres are in the S-phase (Barnes et al., 1993; Campbell et al., 1994), this is not easily accomplished and the entire procedure is limited. Synchronization of blastomeres with nocodazole has been reported in mice (Tsunoda and Kato, 1992; Otagaeui et al., 1994b) and cattle (Samake and Smith, 1996), however success with cell cycle inhibitors has been variable (Fulka et al., 1996). Also, others have suggested that 40 to 60% of ES-like cells are in the G1 phase of the cell cycle at any given time (Stice et al., 1996). Although the cell cycle has not been characterized for porcine ES cells, it is possible that random selection of an ES cell to use as a karyoplast results in a G1 karyoplast most of the time.

In addition, another method in mice has been reported that would require the use of G2 karyoplasts. With this method, oocytes are enucleated at telophase I by a chemical enucleation procedure (Fulka and Moor, 1993) resulting in decreased MPF levels, MPF levels are restored by culture of enucleated oocytes, G2 karyoplasts are fused to cytoplasts and these complexes incubated for 90 min (MPF exposure) before activation (decreased MPF levels; Fulka et al., 1994). They reported that this protocol induced complete nucleolar reprogramming (Fulka et. al., 1996). However, this method is also limited to karyoplasts from one stage of the cell cycle. Campbell et al. (1996a) and Wilmut et al. (1997) reported that cultured, embryonic cell lines as well as somatic cell lines from an adult animal could be reprogrammed and develop into live animals. The cells were serum starved for 5 d to induce a state of quiescence (G0). In addition to a synchronous population of karyoplasts that are acceptable for transfer into any stage of cytoplast, cells in the G0 stage of the cell cycle may be more suitable for reprogramming and remodeling. The G0 stage of the cell cycle has a possible role in differentiation and alteration of chromatin does occur in these nuclei (Wilmut et al., 1997).

Figure 2:
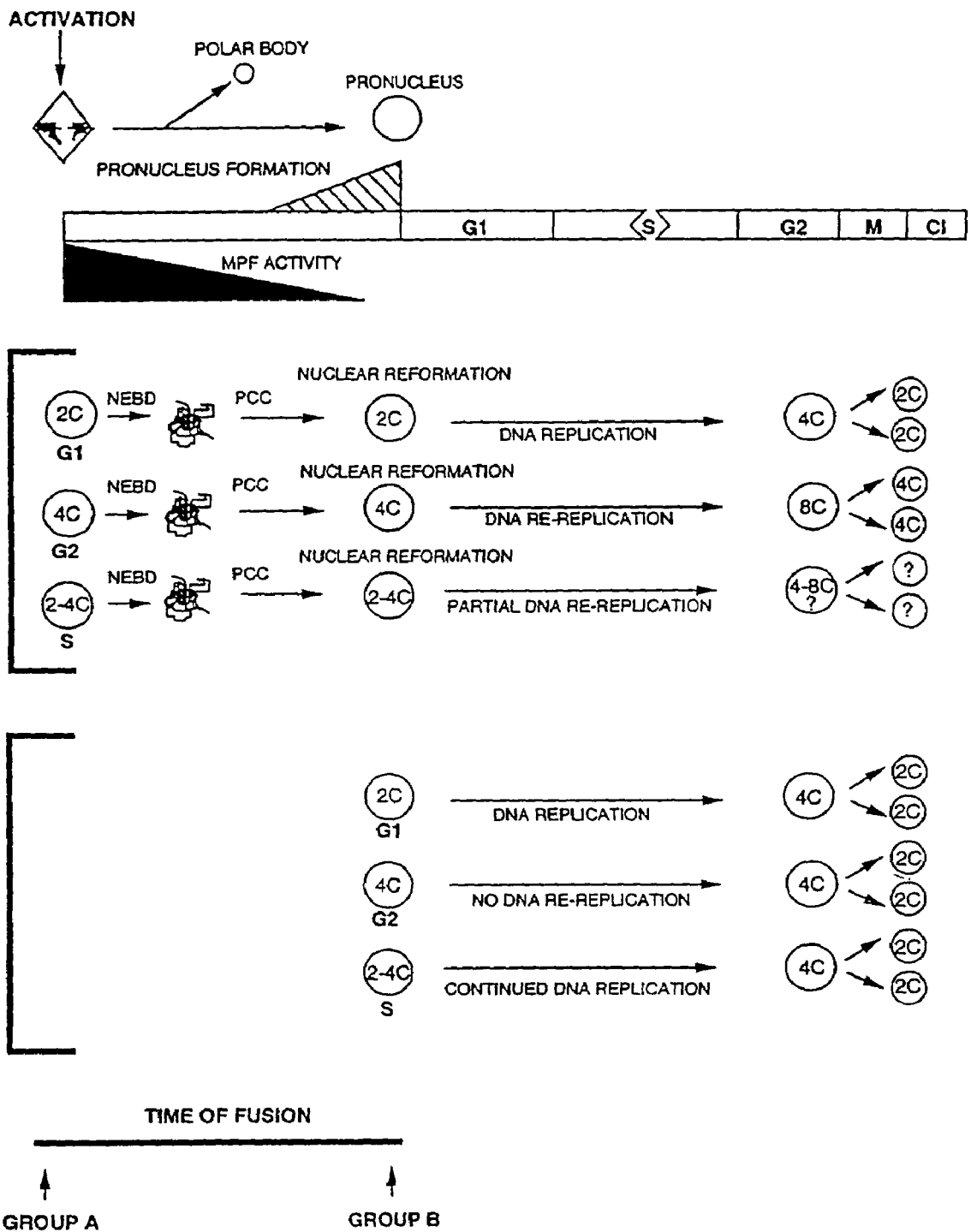
FIG. 2 represents "The Universal Recipient" theory. Group A represents simultaneous activation and fusion of karyoplasts and cytoplasts. Group B represents activation of cytoplasts followed by fusion of karyoplasts. Adapted from Campbell et al. (1993).

Another method is to synchronize cytoplasts to a stage of the cell cycle that would be appropriate for karyoplasts at any stage of the cell cycle. Campbell et al. (1993) reported a method to activate cytoplasts before the fusion process allowing MPF levels to decrease (The Universal Recipient; FIG. 2) which, in turn, improved developmental rates appreciably. In this case, DNA re-replication (G2 nuclei) and partial DNA re-replication (S-phase nuclei) do not occur. Therefore, the cell cycle stage of the karyoplasts should not hinder the ploidy of NT embryos. As long as one knows when pronuclear formation occurs in activated oocytes, enucleated oocytes can be activated and not fused until the timepoint when normal pronuclear formation would have occurred. This strategy has been successful in bovine (Campbell et al., 1993; Barnes et al., 1993; Kono et al., 1994; Stice et al., 1994; Duet al., 1995b), ovine (Campbell et al., 1994) and murine (Otaegui et al., 1994a) NT experiments. Further, Stice et al. (1994) reported similar developmental rates for NT embryos constructed from enucleated, activated oocytes or enucleated zygotes.

Another strategy to obtain pronuclear cytoplasm (low in MPF activity) is the use of enucleated zygotes as cytoplasts. However, enucleation of bovine, ovine and porcine zygotes requires manipulation to visualize pronuclei, as discussed below. Numerous reports have indicated the benefit of oocytes over zygotes for bovine (Prather et al., 1987; Robl et al., 1987), murine (Cheong et al., 1993; McGrath and Solter, 1984) and rabbit (Modlinski and Smorag, 1991) NT embryo development.

Nuclear transfer can be divided into five components: enucleation of cytoplasts, isolation and injection of karyoplasts, fusion of karyoplasts with cytoplasts, activation of karyoplast-cytoplast complexes and development of karyoplast-cytoplast complexes.

Figure 3A:
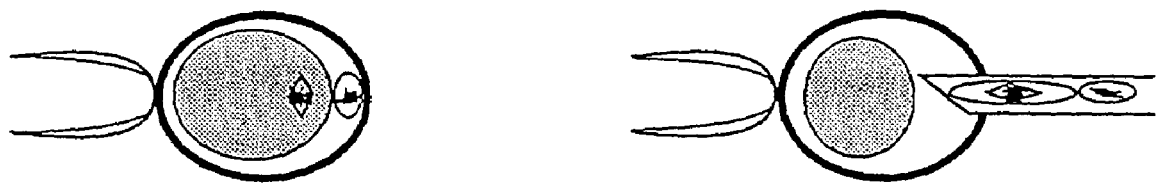
FIGS. 3A-3C are schematic diagrams of cloning by nuclear transfer. Chromosomal DNA is removed from the recipient oocyte (FIG. 3A), and then a blastomere from the donor embryo is transferred to the enucleated recipient oocyte (FIG. 3B). Finally, an electrical pulse is generated which promotes fusion of the blastomere and oocyte membranes, which transfers the nucleus into the oocyte cytoplasm to initiate embryonic development (FIG. 3C). The newly constructed embryo is usually cultured in vitro before transfer to a suitably prepared recipient. From Wheeler and White (1993).
Figure 3B:
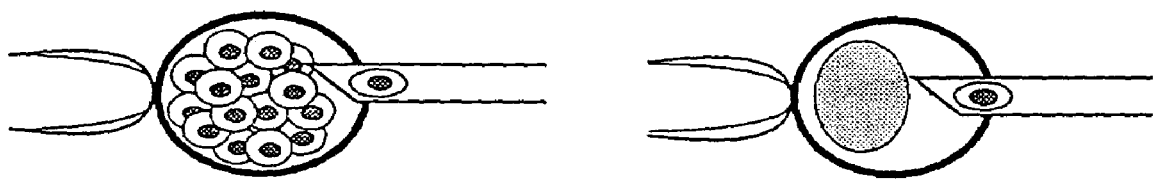
Figure 3C:

Although enucleation of zygotes and later stage embryos has been performed in mice, the most common cytoplasts used in NT experiments are metaphase II oocytes. The metaphase plate is next to the polar body at this stage so that all chromosomes can be removed with a minimal amount of cytoplasm. Further, the pronuclei of zygotes from large domestic animals can only be seen by differential interference-contrast and phase-contrast microscopy, staining, or centrifugation, making removal of the chromosomes much more difficult. Enucleation of cytoplasts can be accomplished in a number of ways. These methods include irradiation of chromosomes, oocyte bisection, chemical disruption and mechanical removal, for example, with a glass micropipet. Ultraviolet irradiation of chromosomes is commonly performed in amphibians, but this technique has not been successful with mammalian oocytes (Tsunoda et al., 1988). The use of ultraviolet irradiation at DNA-specific wavelengths has been suggested (Bradshaw et al., 1995). Targeted laser ablation methods allowed specifically irradiating the metaphase chromosomes with little damage to the cytoplasm. This method has been successful in assisted fertilization and assisted hatching procedures (Tadir et al., 1992, 1993). However, cytoplast enucleation is believed not to have been reported. Oocytes can be bisected and both halves used for NT. Half of the NT embryos from these demi-oocytes are triploid and do not develop to term (Smith, 1992). Mouse oocytes can be chemically enucleated with an inhibitor of the enzyme topoisomerase II (Fulka and Moor, 1993). The most common method of enucleation in mammals is the mechanical removal of the polar body and metaphase plate with a glass micropipet (FIG. 3). Prior to enucleation, oocytes are stained with a fluorescent dye (Hoescht 33342) and enucleation can be confirmed by examination of the enucleated cytoplasm or the oocyte using fluorescence microscopy (Tsunoda et al., 1988; Westhusin et al., 1992). However, development of cytoplasts stained with Hoescht 33342 depends on the duration of ultraviolet exposure and the concentration of dye (Tsunoda et al., 1988).

Traditional methods to produce "cloned" animals utilize early cleavage stage blastomeres transferred to enucleated oocytes. The oocytes are then fused with the transferred nucleus, induced to resume cytoplasmic and nuclear development, cultured and transferred to surrogate mothers. The recent development of ES cell lines in the pig provides a source of small cells of potentially unlimited number for NT (Wheeler, 1994). Karyoplasts are placed into the perivitelline space of the cytoplast, for example, with the use of a glass micropipet (FIG. 3). In addition, ICM cells can be lysed and directly microinjected inside the plasma membrane of cytoplasts to produce calves from NT (Collas and Barnes, 1994). This is similar to methods described for amphibian NT.

Fusion is the process by which the plasma membranes of two cells are temporarily destabilized, allowing the two plasma membranes to merge. Fusion of the karyoplast and cytoplast has been accomplished by electrofusion (FIG. 3). An electrical pulse is applied to the cells, which is thought to cause pore formation or a destabilization of cell membranes, allowing fusion to occur (Robl et al., 1992a). The rate (efficiency) of fusion is dependent upon the size and type of cells to be fused (Chang, 1992). Further, cell contact, alignment, field strength and pulse duration can influence electrofusion efficiency (Robl et al., 1992b). A variety of electrofusion parameters can be found in the literature for a number of species. However, in the pig, only parameters to fuse two-, four- and eight-cell blastomeres have been reported (Prather et al., 1989). Due to the discrepancy is size between the ES cell and the cytoplast, these parameters may not be reliable to fuse the ES cells and cytoplasts. Polyethylene glycol has been reported to cause fusion of bovine ICM cells with enucleated oocytes, although the repeatability between chemical lots was variable (Sims and First, 1993). Sendai virus also has been used successfully as a fusing agent in mouse embryos (McGrath and Solter, 1983a) but was less effective in other species (Robl and First, 1985; Willadsen, 1986; Robl et al., 1987). Alternatives to electrofusion have been examined only using blastomeres, therefore the effectiveness of chemical fusing agents may differ for conditions using porcine ES cells.

In NT, because the recipient oocyte is not exposed to sperm, fertilization and activation do not occur. Therefore, other methods are used to mimic the activation process which normally occurs at fertilization. In NT studies, researchers have reported success when activation of cytoplasts has occurred prior to fusion, simultaneously with fusion and following fusion. Generally, simultaneous fusion and activation are completed with electroactivation because the fusion pulse also activates the oocyte. However, oocyte activation prior to or following fusion can be performed in a number of ways. Activation of oocytes has been performed in mammals with physical stimuli such as mechanical pricking or manipulation of oocytes (Markert, 1982), thermal heating or cooling, electric pulses (Whittingham, 1980) and aging (Ware et al., 1989). Chemical stimuli that can induce oocyte activation include enzymatic, osmotic, ionic (divalent cations or calcium ionophores), anaesthetics (general or local), phenothiazine tranquillizers and protein synthesis inhibitors (Whittingham, 1980).

Electrical activation has been the most popular method of porcine oocyte activation. However, most activation studies in pigs have been performed using IVM oocytes which may not be comparable to those matured in vivo. Factors that have been examined in porcine IVM oocyte electrical activation include: voltage dependence, temperature dependence prior to maturation, glucosamine dependence during maturation, time in activation medium, pH dependence, in vitro development following activation (Prather et al., 1991c), duration of IVM prior to activation, eCG vs. LH and follicle stimulating hormone in IVM medium prior to activation, number of pulses (Hagen et al., 1991b), second messengers in activation medium (Schoenbeck et al., 1993), cycloheximide treatment following activation (Nussbaum and Prather, 1995), cytochalasin B treatment following activation, IVM in Waymouth's medium or tissue culture medium-199 prior to activation (Jolliff and Prather, 1997), okadaic acid in activation medium (Rickords et al., 1993) and micromanipulation prior to activation (Lee et al., 1993). Treatment with ethanol (Saito et al., 1993), Ca2+-, Mg2+-, H+-ionophore (A23187; Prather et al., 1991c), cycloheximide, puromycin (Nussbaum and Prather, 1995), a combination of ethanol and cycloheximide (Petr et al., 1996), staurosporine (protein kinase inhibitor; Joliff and Prather, 1997), okadaic acid (protein phosphatase inhibitor; Grocholova et al., 1997), and injection of second messengers (Machaty et al., 1995) have also been tried for porcine oocyte activation.

Culture systems that are successful for culture of one-cell embryos to blastocysts are used to culture NT embryos. Other methods have also been reported. Nuclear transfer embryos can be cultured with fertilized zygotes, or "helper embryos", to improve developmental rates (Keefer and Stice, 1992). It is possible that NT embryos may not secrete or produce the appropriate components and the "helper embryos" may provide these components. Further, ovine NT embryos are placed in agar chips and cultured in vivo with an intermediate recipient female (Willadsen, 1982; Smith and Wilmut, 1989). Next, the embryos that develop to the blastocyst stage can be injected into another appropriate recipient to produce live young. The blastocyst development determined for porcine NT embryos was accomplished by in vivo culture in synchronized recipients for 6 d (Prather et al., 1989). The only live pig that was produced from NT had been transferred into a bred recipient to assure maintenance of pregnancy (Prather et al., 1989).

Other strategies to improve developmental rates of NT embryos have been reported. The culture of NT embryos in cytochalasin B for 1 h following fusion increases developmental rates (Smith and Wilmut, 1989; Collas and Robl, 1990; Yang et al., 1992a). This treatment may prevent polar body expulsion and subsequent haploid embryos following NT (Smith and Wilmut, 1990). It is unknown if a mitotic karyoplast will undergo meiotic reduction following transfer into an enucleated, metaphase II oocyte. In murine NT, a number of studies have reported that extrusion of a polar body and formation of a single pronucleus were beneficial to embryo development and birth of live young (Kono et al., 1992; Cheong et al., 1993, 1994). Powell and Barnes (1992) did not detect polar body formation in bovine embryo clones, and no other reports are believed to exist (Campbell et al., 1996b). This may be an important difference between species and may be very beneficial to porcine NT.

Three experiments were designed to evaluate modifications in a porcine embryo culture system. The objective of the first was to examine the in vitro development of Meishan embryos obtained at four different stages of development (four-cell, eight-cell, compact morulae and blastocysts) in a Whitten's based medium containing three different protein supplements. The protein supplements examined were 5% fetal bovine serum (W-FBS), 0.4% bovine serum albumin (W-BSA) and 5% fetal bovine serum and 0.1% glucose (W-FBS+G). Embryos were flushed with Dulbecco's phosphate buffered saline (D-PBS) and cultured in 50 μl drops of a Whitten's based medium under paraffin oil at 39° C. in a humidified 5% $CO_2$ in air environment. In addition, four-cell embryos were cultured with one or four embryos per drop. No difference was determined between one and four embryos per drop except for 4-cell development to blastocysts ($P<0.10$). Results from culture of four- and eight-cell embryos indicated that W-BSA supported greater development to compact morulae and blastocysts ($P<0.05$) than W-FBS or W-FBS+G, but no treatment was successful in permitting hatching of the embryos from the zona pellucida. W-FBS and W-FBS+G supported more compact morulae and blastocysts to hatched blastocysts than W-BSA (P<0.05). The objective of the second experiment was to investigate the effect of different BSA lots on development of porcine embryos at stages prior to the maternal to zygotic transition in modified Whitten's medium+1.5% BSA. Embryos (n=83) were flushed from oviducts of five Meishan, two Duroc×Meishan and two Yorkshire females with D-PBS and randomized to a Whitten's based medium with 1.5% BSA from four different lots. The control lot was essentially fatty acid-free. Embryos were washed three times and placed in 50 μl drops under paraffin oil at 39° C. in a humidified 5% $CO_2$ in air environment. No difference was detected among BSA lots for embryo development following 96 h of culture (P>0.66). The objective of the third experiment was to investigate the development of Meishan and Yorkshire embryos at stages prior to the maternal to zygotic transition (one-, two- and early four-cell) in modified Whitten's medium+1.5% BSA. Embryos were collected, handled and cultured as described above. A higher percentage of one-cell Meishan embryos developed to the eight-cell and compact morula stages than Yorkshire embryos following 96 h of culture (P<0.10). More Yorkshire two-cell embryos developed to the eight-cell stage than Meishan embryos (P<0.10). However, no breed differences were detected for one-cell development to the blastocyst stage, two-cell development to the compact morula and blastocyst stages, and four-cell development to any stage (P>0.15).

We determined appropriate conditions for porcine embryo development from one-cell through hatched blastocyst stages. It was also essential to implement a culture system that would accommodate occidental breed embryos (Yorkshire) as well as Chinese Meishan embryos since little is known about in vitro culture of Meishan embryos. A culture system was described for culture of embryos for the production of ES cells (Gerfen, 1993), but it was not known previously if this system would support development of all stages of porcine embryos.

The maternal to zygotic genome transition or in vitro 'block' occurs at the four-cell stage in porcine embryos (Jarrell et al., 1991) and difficulties in the ability to culture porcine embryos through this stage have been reported (Davis, 1985). In addition, results between laboratories and even within laboratories have shown contradictory results (Davis, 1985). However, systems have improved significantly and a variety of simple, defined media have been proven successful (Davis and Day, 1978; Petters et al., 1990; Hagen et al., 1991a; Misener et al., 1991). Generally, investigators have attempted to obtain a medium that will support development throughout all stages of in vitro culture. Nevertheless, dynamic culture systems may be more similar to in vivo conditions. In addition to in vivo (Prather et al., 1991b) and organ (mouse oviduct; Krisher et al., 1989) culture, improved development of one-cell porcine embryos to blastocysts has been reported with the addition of oviductal fluid (Archibong et al., 1989), oviduct epithelial cells (White et al., 1989), hyaluronic acid (Miyano et al., 1994), glutamine, sorbitol, taurine or hypotaurine (Reed et al., 1991; Petters and Wells, 1993) to the culture medium. Beckmann and Day (1993) reported a medium that supported development from the one-cell to blastocyst stages at high rates and produced live pigs following transfer to recipient animals. This medium was selected to culture embryos from the one-cell to blastocyst stages.

Robl and Davis (1981) originally reported the beneficial effect of serum on morula and blastocyst development, especially on hatching from the zona pellucida. However, early stage porcine embryos are cultured with BSA instead of serum due to detrimental effects of serum at these stages (Davis, 1985; Petters and Wells, 1993). In addition, it has been reported that different BSA lots had an effect on blastocyst development of early bovine (Rorie et al., 1994), ovine (Batt and Miller, 1988), caprine (Batt et al., 1991) and rabbit (Kane, 1983) embryos. It was suggested that the differences in citrate levels might be the key factor (Rorie et al., 1994).

Relatively little research has been reported on the in vitro development of Meishan embryos. Youngs et al. (1993) reported that Meishan embryos developed slower than embryos from control Yorkshire females. They attributed the increased embryo survival of the Meishan females to the ability of the earlier maturing embryos to produce less estradiol-17b and therefore allowing the later maturing embryos to fit in a window of uterine development. The objectives of the studies in Example 1 were to compare in vitro development of pre-implantation Meishan embryos in a Whitten's based medium with three different protein supplements, to examine development of porcine embryos prior to the maternal to zygotic genome transition (one-, two- and early four-cell) in modified Whitten's medium with four different lots of BSA and to compare development of early embryos (prior to maternal to zygotic genome transition) from Yorkshire and Meishan females.

A culture system was described to culture embryos for the production of ES cell lines (Gerfen, 1993). We examined whether this culture system supported development of all stages, particularly stages prior to the maternal to zygotic genome transition, of porcine embryos. As indicated in Experiment 1 in Example 1 of this study, this medium did not successfully support development of early stage porcine embryos to the blastocyst stage. Therefore, it could not be used to culture embryos collected prior to the maternal to zygotic transition. Since a successful culture system was essential to NT experiments, a new medium had to be selected in order to culture one-cell embryos to the blastocyst stage. Beckmann and Day (1993) reported a medium that supported high rates of one-cell development to the blastocyst stage. Moreover, this medium produced live pigs upon blastocyst transfer to recipient animals indicating similarities to in vivo conditions for embryo culture. This medium was used in the experiments described in Examples 2 and 3 related to culture of embryos prior to the maternal to zygotic transition.

As used herein, heterologous DNA is DNA which does not occur in nature in a particular cell. A heterologous DNA molecule can be entirely composed of sequences which in nature do not occur in that cell, or it can comprise sequences derived from the organism or cell, but covalently linked to DNA sequences foreign to that cell. Sequences which are part of the heterologous which is introduced into the cell of interest can include sequences encoding proteins, transcriptional regulatory sequences and sequences directing transcriptional expression of a structural RNA or a functional RNA (messenger, ribozyme or interfering RNA).

In the present context, a transgenic cell or transgenic animal contains heterologous DNA. That heterologous DNA can be introduced into the cell by any means known to the art: transfection, electroporation, transformation, nuclear transfer and any other means known. Desirably, the heterologous DNA can include either a phenotypic marker or a sequence which is detected by hybridization or amplification, for example. The heterologous DNA incorporated within a cell and nonhuman animal of interest can result in the expression of protein products including, but not limited to, hormones, growth factors, enzymes, clotting factors, apoliproteins, receptors, drugs, pharmaceuticals, bioceuticals, nutraceuticals, oncogenes, tumor antigens, tumor suppressors, cytokines and viral, parasitic or bacterial antigens. Specific examples can include proinsulin, insulin, growth hormone, androgen receptors, insulin-like growth factors, insulin growth factor binding proteins, angiogenesis factors (e.g., acidic fibroblast growth factor, basic fibroblast growth factor, angiogenin), factor VIII, genetically modified factor VIII, dermal growth factor, matrix proteins (collagens, laminin), oncogenes (ras, jun, fos, myc, erb, src, sis), E6 or E7 transforming sequence, p53 protein, cytokine receptor, interleukins, interferons, enzymes such as phenylalanine hydroxylase, truncated apoliprotein B, lipoprotein lipase, cholesterol hydroxylase, or enzyme inhibitors such as α-1-antitrypsin inhibitor or trypsin inhibitor, can be expressed. Alternatively, the introduced heterologous DNA can result in functional inactivation of a resident gene by insertion or by causing a deletion. Genes encoding enzymes involved in glycosylation, where the glycosylation leads to an immune response or rapid removal from circulation, can be inactivated with an advantageous result—tissues such as heart valves may be less immunogenic when used in an allograft or a protein product such as factor VIII may be less immunogenic and cleared less quickly from circulation when used in a medical setting, especially in humans, such as for treatment of hemophilia.

As used herein, nuclear transfer means introducing a full complement of nuclear DNA from one cell into an enucleated cell. Nuclear transfer methods are well known in the art. See, for example, U.S. Pat. Nos. 4,994,384 and 5,057,420.

An enucleated cell is one in which the nucleus has been physically removed (e.g., by aspiration (see, e.g., U.S. Pat. No. 4,994,384 or U.S. Pat. No. 5,057,420) or functionally inactivated (see, e.g., Wagoner et al. (1996) Theriogenology 46:279-284 and herein below).

A fusogenic agent is one which causes portions of the membranes of different cells to fuse, preferably allowing intermingling of contents, such as where nuclear transfer is allowed to occur. Fusogenic agents include, without limitation, polyethylene glycol, trypsin, dimethylsulfoxide, lectins, agglutinins, viruses including but not limited to Sendai virus. Nuclear transfer can be achieved by fusion of the nuclear donor cell and the enucleated recipient cell (cytoplast); the product termed a nuclear fusion cell herein.

Activation refers to any composition or physical stimulus which causes cell division, especially in the product of nuclear transfer. Activating agents can include electrical stimuli, ionophores, protein kinase inhibitors, phorbol esters, temperature change, protein synthesis inhibitors such as cycloheximide, mechanical stimuli and thapsigargin. See for example, U.S. Pat. No. 6,011,197 for a discussion of activation and oocyte maturation as well as herein.

A surrogate mother is a nonhuman animal of the same species as the nuclear transfer cell. The nuclear transfer cell can be cultured in the laboratory after the nuclear transfer and then placed in the uterus of the surrogate mother, where it becomes implanted in the uterus and grows and develops to produce a liveborn animal.

Liveborn refers to an animal which is alive for at least one second after it exits the maternal host, either by natural birth, induced birth or surgical removal.

Monoclonal or polyclonal antibodies, preferably monoclonal, specifically reacting with a protein of interest encoded by a particular coding sequence may be made by methods known in the art. See, e.g., Harlow and Lane (1988) *Antibodies. A Laboratory Manual*, Cold Spring Harbor Laboratories; Goding (1986) *Monoclonal Antibodies. Principles and Practice,* 2d ed., Academic Press, New York.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning,* Second Edition, Cold Spring Harbor Laboratory, Plainview, N.Y.; Maniatis et al. (1982) *Molecular Cloning,* Cold Spring Harbor Laboratory, Plainview, N.Y.; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics,* Cold Spring Harbor Laboratory, Cold Spring Harbor, N.Y.; Old and Primrose (1981) *Principles of Gene Manipulation,* University of California Press, Berkeley; Schleif and Wensink (1982) *Practical Methods in Molecular Biology;* Glover (ed.) (1985) *DNA Cloning* Vol. I and II, IRL Press, Oxford, UK; Hames and Higgins (eds.) (1985) *Nucleic Acid Hybridization,* IRL Press, Oxford, UK; and Setlow and Hollaender (1979) *Genetic Engineering: Principles and Methods,* Vols. 1-4, Plenum Press, New York. Abbreviations and nomenclature, where employed, are deemed standard in the field and commonly used in professional journals such as those cited herein.

All references cited in the present application are incorporated by reference herein to the extent that they are not inconsistent with the present disclosure.

The following examples are provided for illustrative purposes, and are not intended to limit the scope of the invention as claimed herein. Any variations in the exemplified articles which occur to the skilled artisan are intended to fall within the scope of the present invention.

EXAMPLES

Example 1

Meishan females were bred to Meishan boars and embryos (four-cell, eight-cell, compact morula and blastocyst) were collected from Meishan females only (Experiment 1). Animals were euthanized. Within 30 min after reproductive tract removal, embryos were flushed from the tracts with D-PBS, randomized to treatment in a Whitten's based medium, washed three times and cultured in 50 µl drops underparaffin oil at 39° C. in ahumidified 5% $CO_2$ in air environment. Embryos from four different stages (four-cell, eight-cell, compact morula and blastocyst) were cultured. In addition, four-cell embryos were cultured with either one or four embryos per drop to test the effects 10 of number of embryos per drop on development. A total of 260 four-cell, 35 eight-cell, 69 compact morulae and 64 blastocysts were cultured. The three protein supplements examined were 5% FBS (W-FBS), 0.4% BSA (W-BSA) and 5% FBS and 0.1% glucose (W-FBS+G). Embryos were examined every 12 h and a developmental stage endpoint was used for this experiment. The effects of treatment, embryo donor and number of embryos per drop were examined using Chi-square (c2) analysis.

Following 96 h of culture, more Meishan one-cell embryos had developed to the eight-cell and compact morula stages than Yorkshire embryos (P<0.10; Table 3.3). One-cell embryo development was 83% to the eight-cell stage and 70% to the compact morula stage for Meishan embryos and 63% to the eight-cell stage and 47% to the compact morula stage for Yorkshire embryos. Differences were not detected between breeds for blastocyst development (P>0.90). An effect of embryo donor was detected for development to the eight-cell, compact morula and blastocyst stages (P<0.05). Culture of two-cell embryos for 96 h yielded different results (Table 3.3). More Yorkshire two-cell embryos (100%) developed to the eight-cell stage than Meishan embryos (88%; P<0.10). Breed differences were not detected for development of two-cell embryos to the compact morula and blastocyst stages (P>0.45). Embryo donor effects were detected for development to all stages (P<0.01). Results from four-cell embryos indicated no differences between breeds for development to the eight-cell, compact morula and blastocyst stages following 96 h in vitro (Table 3). No effects of embryo donor were detected for development to the eight-cell, compact morula and blastocyst stages (P>0.55).

Results from culture of Meishan four-cell embryos indicated that W-BSA supported greater development to compact morulae and blastocysts than either W-FBS or W-FBS+G (P<0.05; Table 1). However, no treatment was successful in hatching embryos from the four-cell stage (<4% hatched in W-BSA). The number of embryos per drop affected the percentage of four-cell embryos developing to the blastocyst stage (P<0.10) but not the percentage to the eight-cell, compact morula and hatched blastocyst stages (P>0.40). Similarly to four-cell embryos, culture ofMeishan eight-cell embryos with W-BSA produced more compact morulae and blastocysts compared to the other two treatments (P<0.01). Although W-BSA permitted 20% of the eight-cell embryos to hatch while the other two treatments permitted no embryos to hatch, the treatment effect was not significant (P=0.15).

Culture of Meishan embryos from later stages (compact morulae and blastocysts) revealed very different results from earlier stages (Table 1). These results indicated that W-FBS and W-FBS+G matured a larger number of compact morulae and blastocysts to hatched blastocysts than W-BSA (P<0.001). Only 5 and 0%, respectively, of compact morulae and blastocysts hatched in W-BSA. Alsoe, W-FBS (70% of compact morula and 100% of blastocysts) allowed higher rates of hatching (P<0.05) than W-FBS+G (40% of compact morulae and 48% of blastocysts). Embryo donor effects were detected for the percentage of compact morulae reaching the blastocyst and expanded blastocyst stages (P<0.05) but not the hatched blastocyst stage (P>0.10). In addition, donor effects were detected for the number of blastocysts that hatched from the zona pellucida (P<0.05).

W-BSA promoted higher rates of development than W-FBS and W-FBS+G from four- and eight-cell to the blastocyst stage. Similarly, other investigators have reported inhibitory effects for culture of embryos prior to the morula stage in FBS compared to BSA (Dobrinsky et al., 1996). Stone et al. (1984) reported no differences between serum and BSA addition to minimal essential medium supplemented with 1% glucose in development of four- and eight-cell embryos to the blastocyst stage. However, this medium contained a number of supplemental amino acids not present in our medium. Number of embryos per drop influenced the percentage of four-cell embryos developing to the blastocyst stage but not to eight-cell, compact morula and hatched blastocyst stages. The reasons for this result are unknown because it is expected that number of embryos per drop would influence development to all of these stages. However, it is possible that exposure of four-cell embryos to some embryotrophic substance in vitro is beneficial for their development from the compact morula to hatched blastocyst stages.

Our results indicate that there is no benefit of glucose as long as FBS is present in the medium for culture of Meishan compact morulae and blastocysts to hatched blastocysts. The beneficial effect of serum addition on hatching supports the original research completed on domestic breeds of embryos (Robl and Davis, 1981) as well as that of others (Meyen et al., 1989; Rosenkrans et al., 1989; Dobrinsky et al., 1996). Since more four- and eight-cell embryos develop to blastocysts in W-BSA than the other two treatments, it may be beneficial to switch embryos at the compact morula or blastocyst stage into W-FBS to allow higher rates of hatching. Others have reported that culture of one- and two-cell stages to the morula stage with BSA followed by the addition of FBS at the morula stage improved rates of hatching from the zona pellucida (Dobrinsky et al., 1996). Pollard et al. (1995) reported higher rates of zygote development to the blastocyst stage in a medium without glucose and fetal calf serum (Chatot, Ziomek, Bavister [CZB] medium; Chatot et al., 1989) than in a medium that contained both components (modified Eagle's essential medium). These investigators also reported higher rates of hatching for blastocysts cultured in modified Eagle's medium than in CZB. Further, they reported that zygotes cultured to the morula stage in CZB and moved to modified Eagles essential medium for further culture hatched at higher rates than those moved to CZB with or without fetal calf serum. Results from these studies indicate the need for investigation into dynamic instead of static culture systems.

Experiment 2

Five Meishan, two Durocx Meishan and two Yorkshire females were bred to Meishan, Yorkshire and Yorkshire boars, respectively and one-, two- and early four-cell embryos were collected. One-, two- and early four-cell embryos (n=83) were collected from two Yorkshire, two Durocx Meishan and five Meishan gilts. Embryos were surgically flushed from Yorkshire and Durocx Meishan gilts whereas Meishan gilts were euthanized and within 30 min after reproductive tract removal, embryos were flushed from the tracts with D-PBS. Embryos from each gilt were then randomized to modified Whitten's medium with 1.5% BSA (Beckmann and Day, 1993) from four different lots (Sigma Chemical Co., St. Louis, Mo.). The four lots were: BSA-1 (Lot # 12H0184), BSA-2 (Lot # 61H0278), BSA-3 (Lot # 11H1040), and BSA-4 (Lot # 120H9314). BSA-4 was essentially fatty acid-free and was used as the control for this experiment. Embryos were washed three times and placed in 50 µl drops under paraffin oil at 39° C. in a humidified 5% $CO_2$ in air environment. Embryos were examined every 24 h and scored for development. After 96 h, a final developmental score was given to each embryo and a time endpoint was used for this experiment. The effects of BSA lot and embryo donor were examined using Chi-square (c2) analysis.

Culture of porcine one-, two-, and early four-cell embryos in modified Whitten's medium supplemented with 1.5% BSA was an efficient method to obtain development of porcine embryos. Overall, 87% of embryos reached the eight-cell stage, 80% reached the compact morula stage and 46% reached the blastocyst stage. An effect of embryo donor was detected for all stages (P<0.05). No difference was detected among the four lots of BSA for development to the eight-cell, compact morula, blastocyst and expanded blastocyst stages (P>0.66; Table 2).

The BSA lots tested in our study all allowed embryo development. Therefore, fatty acid-free BSA need not be used in the culture of early stage porcine embryos. Dobrinsky et al. (1996) reported no differences between lots of fraction V BSA or fatty acid-free BSA on developmental rates and mean cell numbers of one- and two-cell embryos cultured for 4 d. These studies contradict the report of beneficial effects of fatty acid-free BSA for culture of early porcine embryos (Eberhardt et al., 1994) because the control lot for our experiment was essentially fatty acid-free. However, the fatty acid-free lots were different among these studies. Also, our results differ from those reported for bovine (Rorie et al., 1994), ovine (Batt and Miller, 1988), caprine (Batt et al., 1991) and rabbit (Kane, 1983) embryos. Those studies suggested that citrate levels were the key difference between BSA lots that influences embryo development (Rorie et al., 1994). Nevertheless, since the levels of citrate were not determined for the BSA lots in this study, it is possible that the levels were similar thus resulting in no difference between BSA lots for embryo development.

In contrast to the results shown in Experiment 1, the medium containing higher levels of BSA (1.5 vs 0.4%) and glucose (1 vs 0.1%) did allow hatching from the zona pellucida, although most embryos had not begun hatching after 96 h of culture. This observation is believed to indicate that the combination of 1.5% BSA and 1% glucose is functionally equivalent to 5% FBS. Others have reported that embryos cultured in Whitten's medium with 1.5% BSA had higher cleavage scores than Whitten's medium with 0.1% BSA (Wright, 1977). Petters and Wells (1993) determined that a higher percentage of one- and two-cell embryos reached the blastocyst stage in modified Whitten's without glucose and with 0.4% BSA than in modified Whitten's with glucose and 1.5% BSA. Some investigators have reported beneficial effects of glucose addition to (Petters et al., 1990) or removal from (Misener et al., 1991; Youngs and McGinnis, 1990) the base medium. Glucose is utilized to the greatest extent between the compact morula and blastocyst stages but is metabolized at low levels before the eight-cell stage (Flood and Wiebold, 1988). Although embryos do not require glucose at early stages, the level of glucose present in this medium does not inhibit development of these embryos. Therefore, the glucose can be added without early detrimental effects and utilized when embryos progress to the compact morula and blastocyst stages. Some investigators have reported that the combination of glucose and phosphate (Petters and Wells, 1993) or pyruvate and lactate (Davis, 1985; Stone et al., 1984) cause lower rates of embryo development. However, the medium used in this experiment contains glucose, phosphate, pyruvate and lactate and was successful in promoting early embryo development.

Experiment 3

12 Meishan and nine Yorkshire gilts were bred to Meishan and Yorkshire boars, respectively and one-, two- and early four-cell embryos were collected. A total of 62 one-cell (30 Meishan and 32 Yorkshire), 64 two-cell (40 Meishan and 24 Yorkshire) and 91 early four-cell (53 Meishan and 38 Yorkshire) embryos collected prior to the maternal to zygotic genome transition were cultured including data from Experiment 2 because no effect of BSA lot was detected. Embryos were surgically flushed from Yorkshire gilts whereas Meishan gilts were euthanized and within 30 min after reproductive tract removal, embryos were flushed from the tracts with D-PBS. Embryos were washed three times and placed in 50 µl drops of modified Whitten's medium+ 1.5% BSA (Beckmann and Day, 1993) under paraffin oil at 39° C. in a humidified 5% $CO_2$ in air environment. Embryos were examined every 24 h and scored for development. After 96 h, a final developmental score was given to each embryo and a time endpoint was used for this experiment. The effects of breed and embryo donor were examined for each cell stage using Chi-square (c2) analysis.

Youngs et al. (1993) reported that Meishan embryos developed more slowly (approximately 8 to 9 h) from the four-cell to compact morula and blastocyst stages than Yorkshire embryos. This may be important in the unique ability of Meishan embryos to withstand micromanipulation procedures to a greater extent than occidental breed embryos, as observed in our laboratory, because Meishan embryos may have longer to recover. Although we detected breed differences for one- and two-cell embryo development, no breed differences were detected for 4-cell development to the compact morula or blastocyst stages following 96 h of culture. Without wishing to be bound by theory, it is believed that differences in embryo culture medium, control animal populations and timing of observations were responsible for conflicting results between studies. In contrast, results from the present study indicate that breed differences for developmental rate of embryos prior to the maternal to zygotic genome transition are probably not responsible for Meishan embryo recoverability following manipulation.

Conclusions

Results from Experiment 1 indicated that W-BSA was the most efficient medium for culture of four- and eight-cell Meishan embryos to the blastocyst stage and some component of W-FBS was necessary for hatching of later stage Meishan embryos. Experiment 2 demonstrated that fatty acid-free BSA is not necessary for in vitro culture of early stage porcine embryos. Following 96 h of culture in Experiment 3, more Meishan one-cell embryos developed to the eight-cell and compact morula stages than Yorkshire one-cell embryos. More Yorkshire two-cell embryos developed to the eight-cell stage than Meishan two-cell embryos following 96 h of culture whereas no breed differences were detected for four-cell embryo development to any stage following a 96 h culture period. Finally, these studies indicate the need for further investigation into dynamic culture systems instead of static systems.

TABLE 1

Development of Meishan four- and eight-cell, compact morula and blastocyst stage embryos in Whitten's medium with three different protein supplements

| Treatment[b] | Stage[c] | n | 8-cell | CM | Blastocyst | Hatched | Treatment effect[d] |
|---|---|---|---|---|---|---|---|
| | | | Developmental stage of embryos[a] | | | | |
| W-BSA | 4-cell | 114 | 74% | 60% | 50% | 4% | |
| W-FBS | 4-cell | 96 | 54% | 43% | 34% | 1% | 8, CM, B |
| W-FBS + G | 4-cell | 50 | 64% | 44% | 34% | 0% | |
| W-BSA | 8-cell | 12 | — | 95% | 79% | 21% | |
| W-FBS | 8-cell | 19 | — | 33% | 17% | 0% | 8, CM, B |

TABLE 1-continued

Development of Meishan four- and eight-cell, compact morula and blastocyst stage embryos in Whitten's medium with three different protein supplements

| Treatment[b] | Stage[c] | n | 8-cell | CM | Blastocyst | Hatched | Treatment effect[d] |
|---|---|---|---|---|---|---|---|
| W-FBS + G | 8-cell | 4 | — | 25% | 25% | 0% | |
| W-BSA | C.M. | 20 | — | — | 100% | 5% | |
| W-FBS | C.M. | 20 | — | — | 90% | 70% | H |
| W-FBS + G | C.M. | 10 | — | — | 100% | 40% | |
| W-BSA | Blastocyst | 10 | — | — | — | 0% | |
| W-FBS | Blastocyst | 12 | — | — | — | 100% | H |
| W-FBS + G | Blastocyst | 42 | — | — | — | 48% | |

[a]CM = Compact morula.
[b]W-BSA = Whitten's + 0.4% BSA; W-FBS = Whitten's + 5.0% FBS; W-FBS + G = Whitten's + 5.0% FBS + 0.1% glucose.
[c]Stage of embryo at start of culture.
[d]Developmental stages from which a treatment effect was detected (P < 0.05). 8 = 8-cell; CM = Compact morula; B = Blastocyst; H = Hatched.

TABLE 2

Development of one-, two- and early four-cell porcine embryos following 96 hours of culture in modified Whitten's medium + 1.5% BSA from four different lots

| | BSA lot[a] | | | |
|---|---|---|---|---|
| Trait | BSA-1 | BSA-2 | BSA-3 | BSA-4[b] |
| Total no. embryos | 20 | 16 | 17 | 30 |
| No. eight-cell embryos | 17 (85%) | 14 (88%) | 14 (82%) | 27 (90%) |
| No. compact morulae | 16 (80%) | 14 (88%) | 12 (71%) | 24 (80%) |
| No. blastocysts | 9 (45%) | 7 (44%) | 6 (35%) | 16 (53%) |
| No. expanded blastocysts | 3 (15%) | 1 (6%) | 3 (18%) | 6 (20%) |

[a]The BSA lots were: BSA-1 = Lot# 12H0184, BSA-2 = Lot# 61H0278, BSA-3 = Lot# 11H1040 and BSA-4 = Lot# 120H9314.
[b]This BSA lot was essentially fatty acid-free and was used as the control for this experiment.

TABLE 3

Development of one-, two- and early four-cell embryos from Meishan and Yorkshire females following 96 hours of culture in modified Whitten's medium + 1.5% BSA

| | Breed | |
|---|---|---|
| Trait | Meishan | Yorkshire |
| One-cell embryos: | | |
| Total no. of embryos | 30 | 32 |
| No. eight-cell embryos | 25[†] (83%) | 20 (63%) |
| No. compact morulae | 21[†] (70%) | 15 (47%) |
| No. blastocysts | 1 (3%) | 1 (3%) |
| Two-cell embryos: | | |
| Total no. of embryos | 40 | 24 |
| No. eight-cell embryos | 35 (88%) | 24[†] (100%) |
| No. compact morulae | 34 (85%) | 20 (83%) |
| No. blastocysts | 10 (25%) | 8 (33%) |
| Early four-cell embryos: | | |
| Total no. of embryos | 53 | 38 |
| No. eight-cell embryos | 52 (98%) | 38 (100%) |
| No. compact morulae | 52 (98%) | 35 (92%) |
| No. blastocysts | 18 (34%) | 8 (21%) |

[†]P < 0.10.

Example 2

Four experiments were designed to develop an efficient method for activation of in vivo matured porcine oocytes for use in porcine nuclear transfer technology. All oocytes were flushed from oviducts with Beltsville embryo culture medium (BECM) and cultured in 50 μl drops of modified Whitten's medium+1.5% BSA under paraffin oil at 39° C. in a humidified 5% $CO_2$ in air environment. Oocytes from the first three experiments were stained with Hoescht 33342 and viewed under fluorescent microscopy following 20 h of in vitro culture whereas oocytes from Experiment 4 were fixed, cleared, stained with aceto-orcein and viewed under light microscopy following 24 h of culture. The objective of the first experiment was to study the effect of ethanol on oocyte activation. Ethanol (7% for 5 min) had little effect on oocyte activation as only 8% activation was achieved for both treated and control oocytes. The objective of the second experiment was to determine the effects of cold shock treatment on activation. Oocytes were cultured at 39° C. or 25° C. Cold shock treated oocytes activated at higher rates than control oocytes (74 vs 50%; P<0.05). However, both treatments produced a high percentage of two-cell parthenotes (47% for cold shock and 37% for control oocytes; P<0.05). The objective of the third experiment was to examine the effects of sham enucleation on activation rates. Results indicated that a higher percentage of oocytes activated following sham enucleation than control oocytes (P<0.05). Activation rates for sham enucleated and control oocytes were 62 and 27%, respectively. The objective of the fourth experiment was to investigate the effects of electroactivation and electroactivation followed by culture in the presence of cycloheximide on activation. The treatments were in vitro culture (CNTRL); electroactivation and culture (ELECTRO); and electroactivation and culture in presence of cycloheximide (5 μg/ml; CYCLO). Activation rates were highest for CYCLO oocytes (76%), intermediate for ELECTRO oocytes (49%) and lowest for CNTRL oocytes (13%; P<0.05). Rates of parthenogenetic two-cell formation were highest (P<0.05) for the ELECTRO treatment (33%), intermediate for the CNTRL treatment (7%) and lowest for the CYCLO treatment (0%). Two field strengths (1.3 and 2.8 kV/cm) were tested within the ELECTRO and CYCLO groups. Field strength had no significant effect on activation rates for either treatment but did influence two-cell parthenote formation. Within the ELECTRO treatment, a field strength of 2.8 kV/cm promoted higher rates of two-cell parthenote formation (P<0.05) than a field strength of 1.3 kV/cm. Finally, results indicated that the CYCLO treatment was the most efficient activation method to produce pronuclear stage cytoplasm for use in porcine nuclear transfer procedures.

It was essential to determine a method to produce the appropriate cytoplasm for transfer of porcine ES cells to produce NT embryos. Campbell et al. (1993, 1994) determined a method to obtain cytoplasm acceptable for NT with karyoplasts from any stage of the cell cycle (The Universal Recipient). With this method, oocytes are enucleated and activated. The karyoplasts are fused with the cytoplasts at the timepoint following activation where pronuclei would have been present. This allows MPF levels to decrease which in turn prevents re-replication of DNA from karyoplasts that were in G2 or S-phase of the cell cycle. Therefore, an activation method for in vivo matured oocytes needed to be determined that would produce high rates of pronuclear formation. Further, this activation method needed to be compatible with NT procedures and not inhibit the developmental competence of the NT embryos produced from these cytoplasts.

Although numerous treatments have been attempted to activate porcine oocytes, electrical activation has been the most popular method. However, the majority of reports have utilized IVM porcine oocytes which may not be comparable to in vivo matured oocytes. Artificial activation of IVM oocytes is influenced by the culture medium used for IVM (Yamauchi et al., 1996). Further, the quality of oocytes used as cytoplasts for NT experiments is extremely important (Fulka, Jr. et al., 1996) and differences between IVM and in vivo matured porcine oocytes could be due to different patterns of MPF levels during maturation (Naito et al., 1992).

Treatment of oocytes with ethanol is a successful activation method for murine (Cuthbertson, 1983) and bovine (Nagai, 1987) oocytes, although ethanol activation of IVM porcine oocytes has been unsuccessful (Didion et al., 1990; Saito et al., 1993; Petr et al., 1996). Ethanol treatment of in vivo matured porcine oocytes has not been reported. Cold shock activation has been successful in the rat, hamster (Austin, 1956), rabbit (Pincus and Shapiro, 1940), ferret (Chang, 1950), sheep (Thibault and Ortovant, 1949) and cow (Stice et al., 1994) but not in the mouse (Braden and Austin, 1954). This activation method has not been reported for porcine oocytes. Activation of oocytes has been performed in mammals with physical stimuli such as mechanical pricking or manipulation of oocytes (Markert, 1982). Micromanipulation prior to electroactivation has been examined in porcine in vivo matured oocytes. However, although controls were electroactivated, the effects of micromanipulation alone were not examined (Lee et al., 1993). In general, these stimuli probably trigger activation by perturbation of the plasma membrane (Whittingham, 1980). Next, a cascade of events (mimicking fertilization) occur including depolarization of the plasma membrane, intracellular Ca2+ release, cortical granule exocytosis, breakdown of CSF, loss of MPF activity and resumption of meiosis.

Other investigators have activated oocytes with protein synthesis inhibitors (cycloheximide and puromycin). These inhibitors may prevent synthesis of cyclin B or CSF which are essential to formation of the MPF complex. Protein synthesis inhibitors have been used singly (Siracusa et al., 1978; Clarke and Masui, 1983; Nussbaum and Prather, 1995) or in combination with electroactivation (Yang et al., 1992b; Nussbaum and Prather, 1995), Ca2+-ionophore (Shi et al., 1993) and ethanol (Pressice and Yang, 1994a,b; Yang et al., 1994; Petr et al., 1996) for oocyte activation. Nussbaum and Prather (1995) reported improved activation rates for porcine IVM oocytes with this combination treatment.

The objectives of these studies were to determine the effects of different treatments on activation of in vivo matured porcine oocytes. These treatments were: ethanol; cold shock; sham enucleation; electroactivation; electroactivation and culture with cycloheximide; and electrical field strength.

In all four experiments, gilts were observed for estrus every 12 h. In the first experiment, oocytes from one crossbred Pietran×Meishan and three crossbred Durocx Meishan gilts were collected. In the second experiment, oocytes from three Duroc and three crossbred Duroc× Meishan gilts were collected. Upon onset of estrus, gilts in the first two experiments were given 500 IU of human chorionic gonadotropin (hCG) to promote ovulation 40 to 44 h following hCG injection. In the third experiment, oocytes from one Meishan and two crossbred Duroc×Yorkshire gilts were collected. In the fourth experiment, oocytes from four Meishan, two Yorkshire and five crossbred Duroc×Yorkshire gilts were collected.

In the first experiment, oocytes (n=49) were surgically flushed with BECM (Dobrinsky et al., 1996) approximately 40 to 44 h after hCG injection. Ethanol treatment (four reps) was performed by placing oocytes in BECM with 7% ethanol (vol/vol) for 5 min (n=25) whereas control oocytes were placed in BECM without ethanol for 5 min (n=24). Oocytes were washed three times with BECM and modified Whitten's medium+1.5% BSA (Beckmann and Day, 1993) and placed into 50 µl drops of modified Whitten's medium+ 1.5% BSA under paraffin oil. Oocytes were cultured for 20 h at 39° C. in a humidified 5% $CO_2$ in air environment. Following the culture period, oocytes were stained with Hoechst 33342 (2.5 µg/ml; Sigma, St. Louis, Mo.) for 15 min, washed, viewed under light microcopy (magnification=400:1) and examined under fluorescence for the presence of a second polar body and/or a pronucleus.

In the second experiment, oocytes (n=66) were surgically collected approximately 40 to 44 h after hCG injection from oviducts with BECM. Oocytes were washed three times with BECM and modified Whitten's medium+1.5% BSA and placed into 50 µl drops of modified Whitten's medium +1.5% BSA under paraffin oil. Cold shock treatment (six reps) was performed by culturing oocytes for 20 h at 25° C. in 5% $CO_2$ in air (n=34) whereas control oocytes were cultured at 39° C. in 5% $CO_2$ in air (n=32). At cessation of the culture period, oocytes were stained with Hoechst 33342 (2.5 µg/ml) for 15 min, washed, viewed under light microcopy (magnification=400:1) and examined under fluorescence for the presence of a second polar body and/or a pronucleus as well as two-cell parthenote formation.

In the third experiment, oocytes (n=36) were surgically flushed from crossbred Duroc×Yorkshire gilts whereas the Meishan gilt was euthanized and oocytes were flushed from oviducts with BECM approximately 40 to 44 h after the onset of estrus. Sham enucleated oocytes were placed in micromanipulation medium (BECM+7.5 µg/ml cytochalasin B) and a small volume of cytoplasm was removed opposite the first polar body with a Nikon diaphot microscope (Nikon Inc., Melville, N.Y.) equipped with Narishige micromanipulators (Narishige Co., Ltd., Tokyo, Japan). Control oocytes were placed in micromanipulation medium but not micromanipulated. Oocytes from both treatments were washed three times in BECM and modified Whitten's medium+ 1.5% BSA and placed in 50 µl drops of modified Whitten's medium+1.5% BSA under paraffin oil. Oocytes were cultured for 20 h at 39° C. in a humidified 5% $CO_2$ in air environment. After the culture period, oocytes were stained with Hoechst 33342 (2.5 µg/ml) for 15 min, washed, viewed under light microcopy (magnification=400:1) and examined under fluorescence for the presence of a second polar body and/or a pronucleus.

In the fourth experiment, approximately 40 to 44 h after the onset of estrus, in vivo matured oocytes (n=156) were surgically collected from Yorkshire and crossbred Durocx Yorkshire gilts whereas Meishan gilts were euthanized and oocytes were flushed from oviducts with BECM. Oocytes were randomized to three treatments. The treatments were culture (CNTRL); electroactivation and culture (ELECTRO); and electroactivation and culture in presence of cycloheximide (CYCLO). Oocytes from the ELECTRO and CYCLO treatments were placed in 0.3 M mannitol (pH=7.2) to equilibrate. Next, they were placed between two wire electrodes 1-mm apart (microslide 450; BTX Inc., San Diego, Calif.) in 0.3 M mannitol. A 30 µsec DC pulse was given with a BTX Electro Cell Manipulator 200 (BTX Inc., San Diego, Calif.). Initially, a field strength of 2.8 kV/cm was used and a second study was performed with a field strength of 1.3 kV/cm. Oocytes from CNTRL and ELECTRO treatments were washed three times with BECM and modified Whitten's medium+1.5% BSA and placed into culture with modified Whitten's medium+1.5% BSA under paraffin oil. Oocytes from the CYCLO treatment were washed three times with BECM and modified Whitten's medium+1.5% BSA+cycloheximide (5 µg/ml; Sigma Chemical Co., St. Louis, Mo.) and placed into culture with modified Whitten's medium+1.5% BSA+cycloheximide (5 µg/ml) under paraffin oil. Within all treatments, oocytes were cultured for 24 h at 39° C. in a humidified 5% $CO_2$ in air environment. Following culture, oocytes were washed three times with BECM, placed in 0.075 M KCl for 10 min and placed in 10% formalin (vol/vol) overnight. Next, oocytes were mounted on glass slides, placed in acetic acid:ethanol (1:2) for 48-72 h and stained for 2 min with 2% aceto-orcein (vol/vol). Oocytes were immediately examined under light microcopy (magnification=400:1) for the presence of pronuclei and the formation of two-cell parthenotes.

In the first three experiments, the effect of treatment on oocyte activation and two-cell parthenote formation was examined by Chi-square (c2) analysis. In the fourth experiment, the effects of treatment and pulse strength on oocyte activation and two-cell parthenote formation were examined by Chi-square (c2) analysis.

Figure 4:
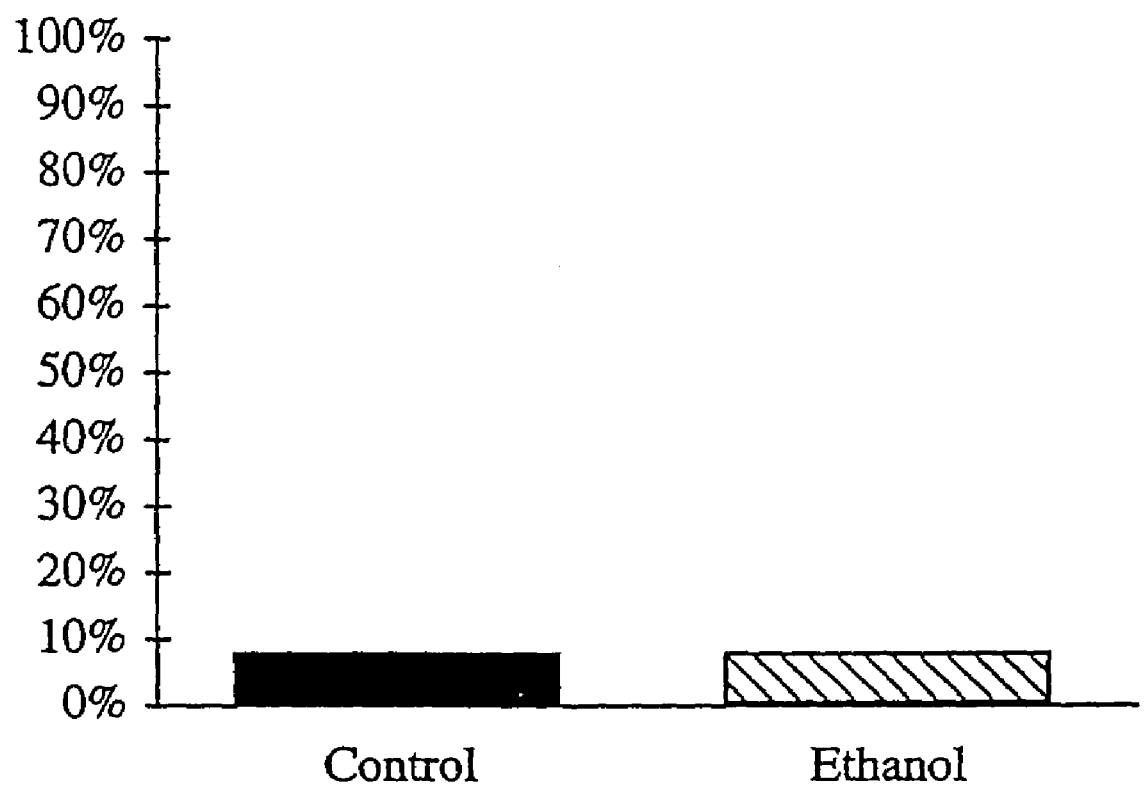
FIG. 4 shows oocyte activation rates for control and ethanol treated porcine oocytes following 20 hours of in vitro culture. Treatments did not differ ($P>0.05$).
Figure 5:
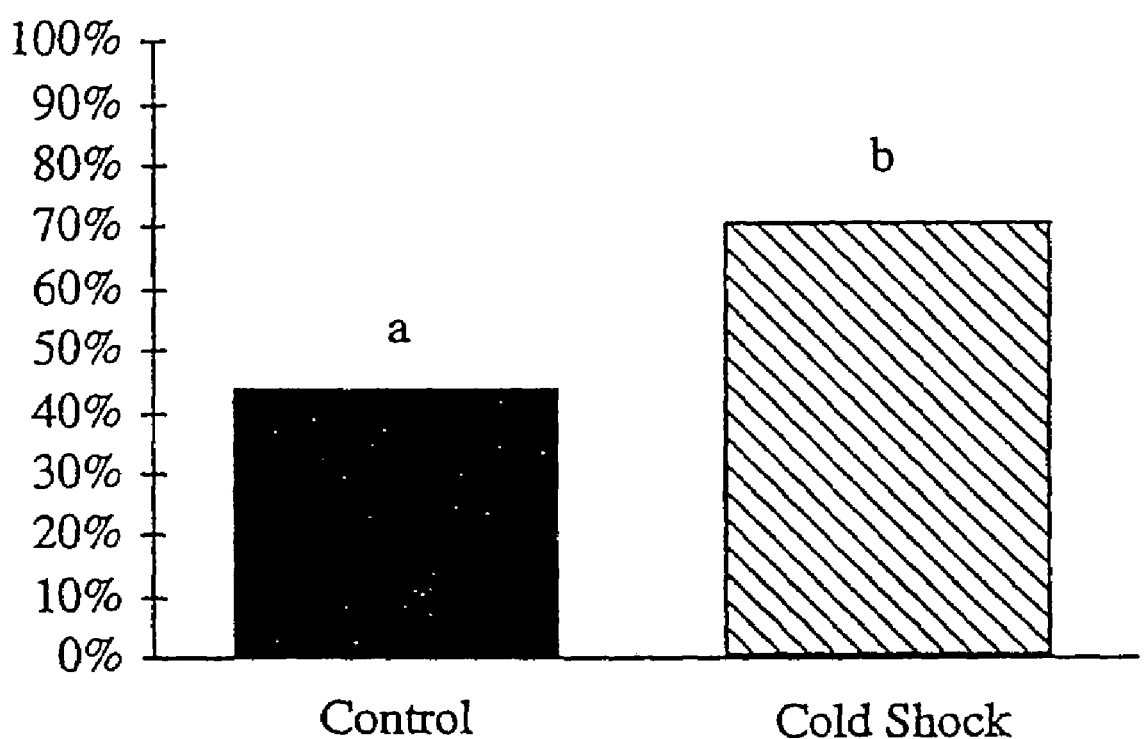
FIG. 5 shows oocyte activation rates for control and cold shock treated porcine oocytes following 20 hours of in vitro culture. a,b Bars with different superscripts differ ($P<0.05$).
Figure 6:
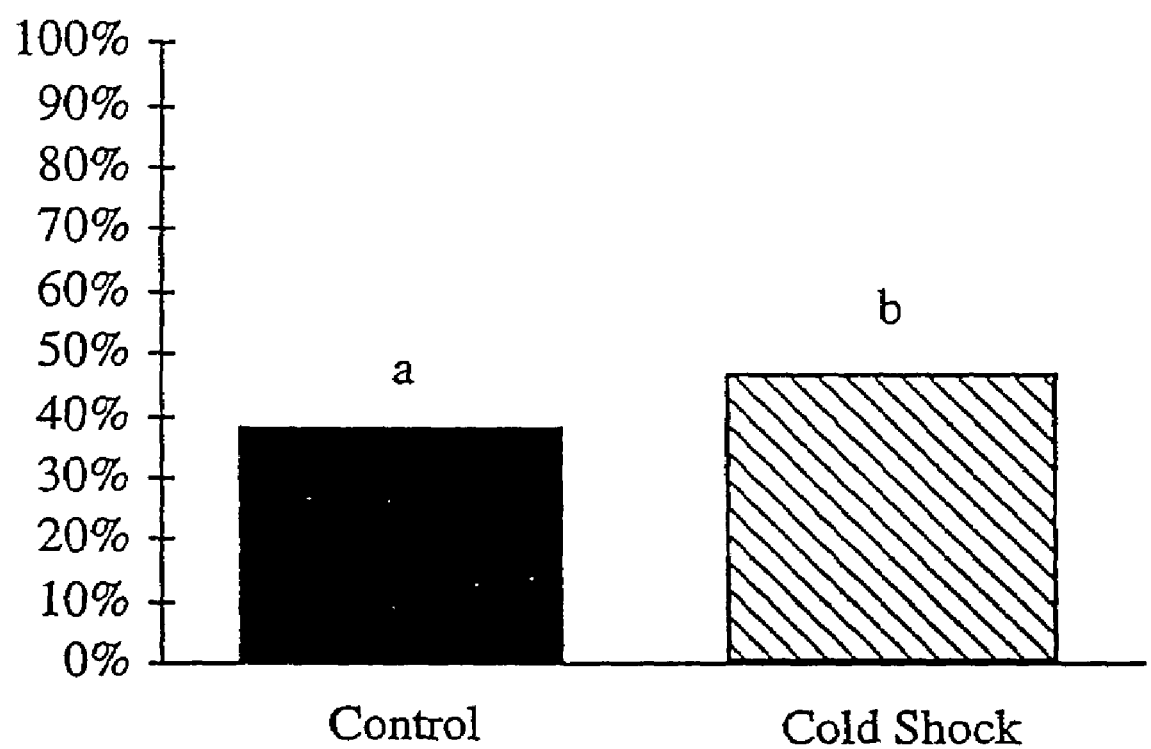
FIG. 6 shows parthenogenetic two-cell formation for control and cold shock treated porcine oocytes following 20 hours of in vitro culture. a,b Bars with different superscripts differ ($P<0.05$).
Figure 7:
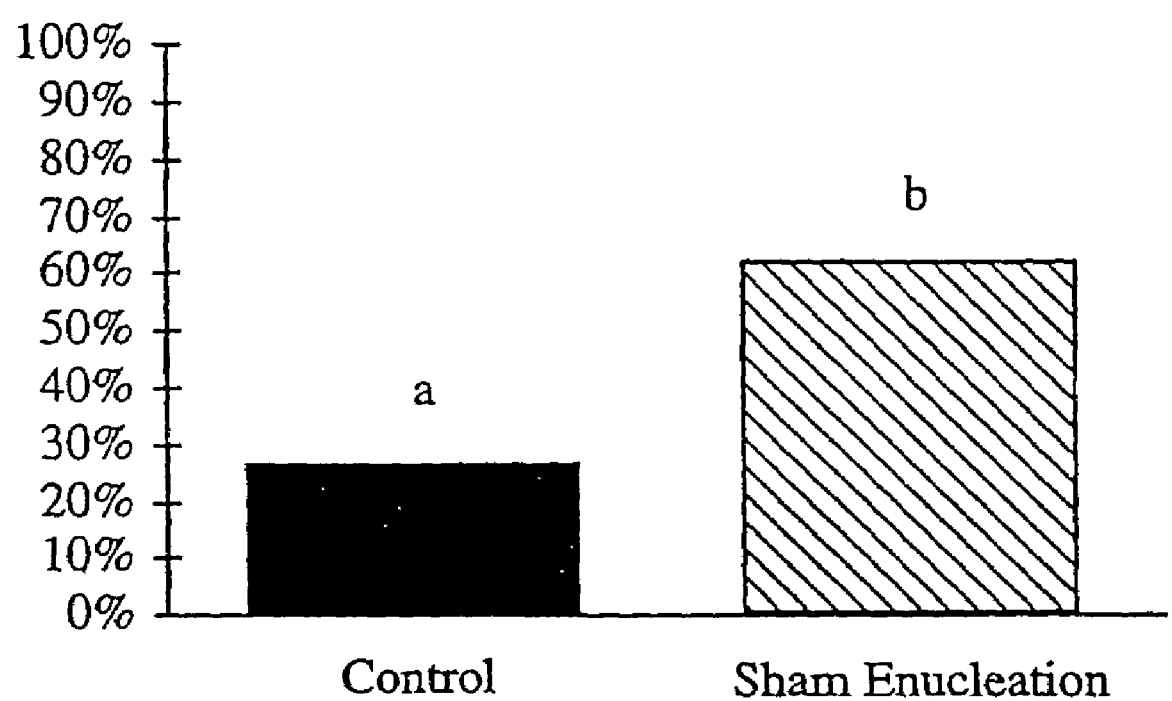
FIG. 7 shows oocyte activation rates for control and sham enucleated porcine oocytes following 20 hours of in vitro culture. a,b Bars with different superscripts differ ($P<0.05$).

Results from the first experiment indicated no difference between control and ethanol activated oocytes (P>0.05; FIG. 4). Activation rates for oocytes from both treatments were 8%. In the second experiment, however, in vivo matured oocytes that were cultured in modified Whitten's medium+ 1.5% BSA at 25° C. (cold shock treatment) activated at higher rates than control oocytes cultured at 39° C. for 20 h (P<0.05; FIG. 5). Rates of activation were 74% for cold shock oocytes and 50% for control oocytes. Both treatments produced a high percentage of two-cell parthenotes (47% for cold shock and 37% for control oocytes; FIG. 6). The sham enucleation treatment in the third experiment activated oocytes at higher rates than control oocytes (P<0.05; FIG. 7). Activation rates for sham enucleated and control oocytes were 62 and 27%, respectively.

Figure 8:
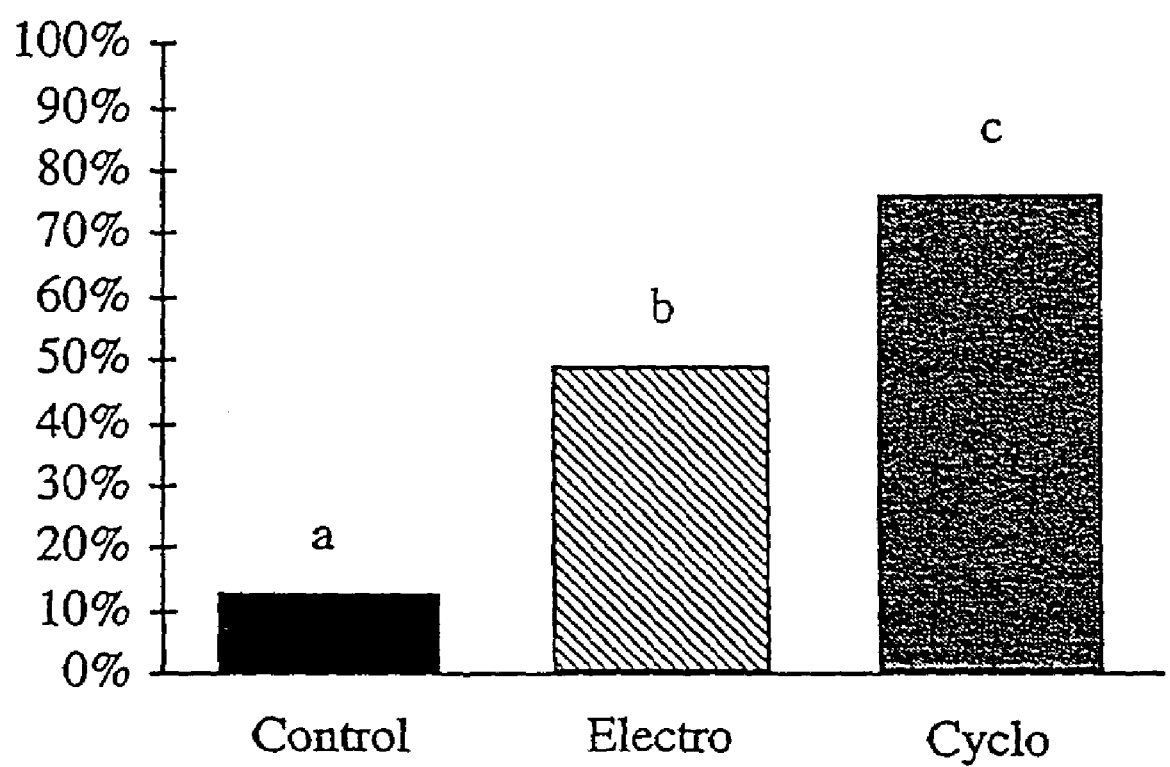
FIG. 8 shows oocyte activation rates for control, electro-activated (Electro) and electroactivated+cycloheximide treated (Cyclo) porcine oocytes following 24 hours of in vitro culture. a,b,c Bars with different superscripts differ ($P<0.01$).
Figure 9:
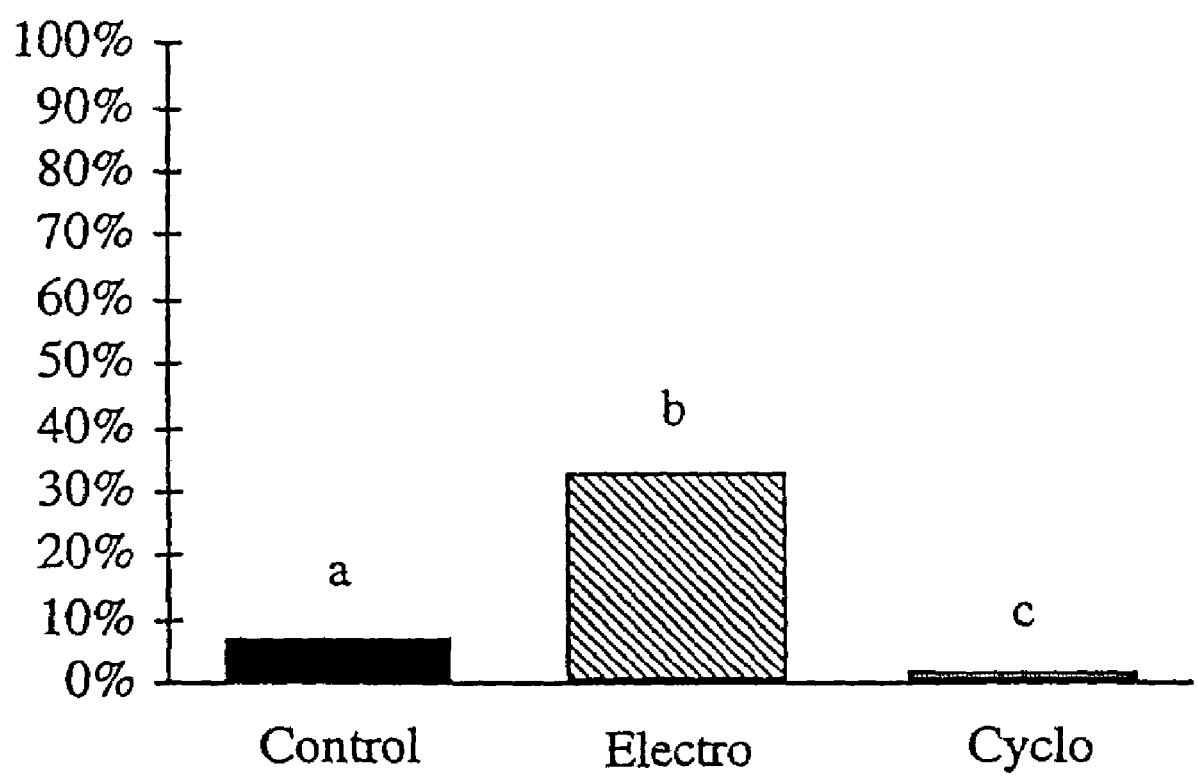
FIG. 9 shows parthenogenetic two-cell formation for control, electroactivated (Electro) and electroactivated+cycloheximide treated (Cyclo) porcine oocytes following 24 hours of in vitro culture. a,b,c Bars with different superscripts differ ($P<0.05$). Parthenogenetic two-cell formation was higher for 2.8 kV/cm than 1.3 kV/cm within the electroactivation treatment ($P<0.05$).
Figures 10A, 10B, 10C, 10D:
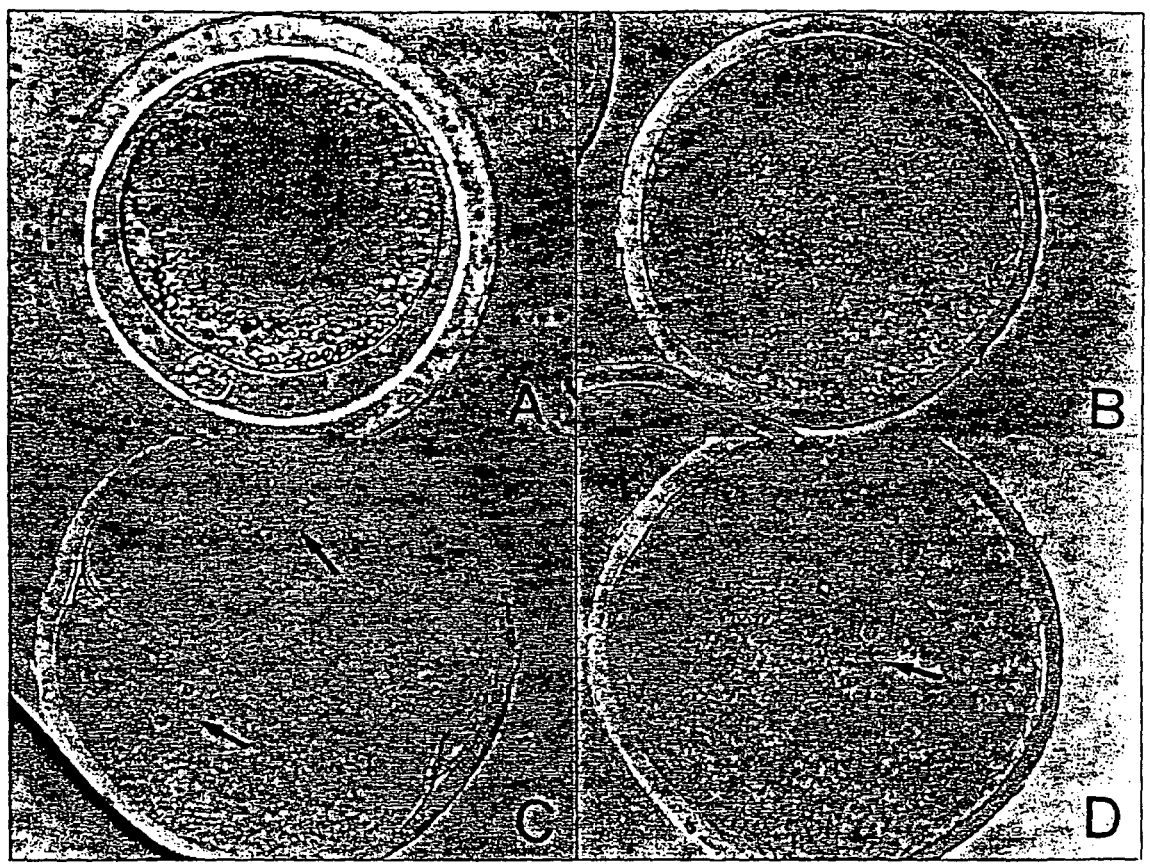
FIGS. 10A-10D are photomicrographs depicting a freshly ovulated, metaphase II porcine oocyte prior to treatment (FIG. 10A) and fixed and stained whole mounts of a control porcine oocyte following 24 hours of in vitro culture (FIG. 10B), an electroactivated porcine oocyte following 24 hours of in vitro culture (FIG. 10C) and an electroactivated porcine oocyte following 24 hours of in vitro culture in the presence of cycloheximide (FIG. 10D). Pronuclei are clearly visible in FIGS. 10C and 10D (arrows) but are not present in FIG. 10B. The oocyte in FIG. 10C has already undergone cleavage (two-cell parthenote).

In the fourth experiment, differences in pronuclear formation were detected among all treatments (P<0.05; FIG. 8). Since no differences were detected between 1.3 kV/cm and 2.8 kV/cm field strengths, these data were combined. Activation rates were highest for CYCLO oocytes (76%), intermediate for ELECTRO oocytes (49%) and lowest for CNTRL oocytes (13%). Rates of parthenogenetic two-cell formation (FIG. 9) were highest (P<0.05) for the ELECTRO treatment (33%), intermediate for the CNTRL treatment (7%) and lowest for the CYCLO treatment (0%). Within the ELECTRO treatment, a field strength of 2.8 kV/cm promoted higher rates of two-cell parthenote formation (P<0.05) than a field strength of 1.3 kV/cm, however within the CYCLO treatment no two-cell parthenotes formed for either field strength. Examples of these treatments are presented in FIGS. 10A-10D.

Experiment 1

Unlike murine and bovine oocytes, in vivo matured porcine oocytes did not respond well to treatment with ethanol for activation. Similar results were reported for IVM porcine oocytes (Didion et al., 1990). Different levels as well as exposure times have been examined for oocytes from a number of species including murine (Cuthbertson, 1983), bovine (Minamihashi et al., 1993) and porcine (Petr et al., 1996). Although maximum activation rates were 15%, activation of IVM porcine oocytes occurred more often with 7 or 10% ethanol than with 0 or 5% ethanol for 3 min (Petr et al., 1996). General anesthetics (i.e., ethanol) have been associated with membrane events such as depolarization, displacement of Ca2+ from membrane phospholipids and cell fusion (Whittingham, 1980). The mechanism of activation for ethanol treatment appears to be different in porcine oocytes than murine or bovine oocytes. This could be due to a higher tolerance of porcine plasma membranes to perturbation by ethanol. Higher concentrations or longer exposure times may be essential for ethanol activation of porcine oocytes. Further, structural differences in porcine plasma membranes may not allow depolarization or displacement of Ca2+ from membrane phospholipids to occur.

Ethanol treatment (10% for 1 min) followed by culture with cycloheximide produced higher activation rates of IVM porcine oocytes (80%) than ethanol activation alone (15%; Petretal., 1996). Ethanol treatment probably induces a single Ca2+ peak resulting in CSF destruction (Pressice and Yang, 1994b) whereas cycloheximide probably prevents synthesis of CSF which eventually results in decreased MPF activity as discussed in Experiment 4. In addition, cycloheximide treatment alone did not activate porcine oocytes (Nussbaum and Prather, 1995; Petr et al., 1996). This suggests that ethanol treatment induces intracellular Ca2+ release and CSF destruction in porcine oocytes but this does not induce meiotic resumption. Therefore, species differences probably occur at the level of intracellular Ca2+ release or protein synthesis and not at the plasma membrane level. These results may be very beneficial to NT studies because ethanol activation provides an easy methodology for treatment of oocytes. In addition, this treatment would alleviate the need for oocyte exposure to electroactivation medium as required with the procedures in Experiment 4 of this study. With difficulty in porcine NT embryo development, these subtle changes in methodology may be a key component in improvement of the system.

Experiment 2

Cold shock (25° C.) treatment of in vivo matured oocytes resulted in higher activation rates than control oocytes. However, more treated oocytes formed two-cell parthenotes than control oocytes which would be unacceptable for nuclear transfer procedures. Thermal shock can cause phase changes in the lipid component of cell membranes thereby causing membrane depolarization and the corresponding cascade of events that mimic fertilization. Successful activation of oocytes with cold shock treatment has been reported in most species with the exception of the mouse indicating differences between mouse oocytes and oocytes from other species in lipid components of the plasma membrane.

Others have reported similar activation rates for cattle oocytes exposed to short term (3 h) or long term (18 h) cold shock (70 and 79%, respectively; Stice et al., 1994). In addition, Stice et al. (1994) reported that no difference in developmental rate was detected between NT embryos derived from enucleated cold shock or control oocytes. Long and short term cold shock were not compared in our study. Short term cold shock, if successful on porcine oocytes, may be more beneficial to the viability of the cytoplasm in NT studies. This indicates that this activation method is not detrimental to the viability of the cytoplasm. Other researchers have reported that a combination of enucleation, aging (4 to 20 h in culture) and cooling (10° C. for 8 h) was a successful activation method (Gall et al., 1996). Following activation, these cytoplasts had a phosphorylation profile similar to electroactivated oocytes, low MPF activity and high mitogen-activated protein kinase.

The third experiment showed that sham enucleation of in vivo matured oocytes resulted in a 35% increase in activation rate over controls. Micromanipulation or mechanical pricking has also been shown to activate oocytes from amphibians and mice (Markert, 1982). This causes perturbation and depolarization of the plasma membrane and the same cascade of events previously stated. Hamster oocytes can be activated by pricking several times with a glass needle but only if Ca2+ is present in the medium (Uehara and Yanagimachi, 1977). This suggests that pricking triggers Ca2+ alterations within the oocyte that are responsible for membrane depolarization.

Although both control and sham enucleated oocytes were treated with cytochalasin B, a cumulative effect of cytochalasin B and sham enucleation on activation can not be ruled out. Lee et al. (1993) reported that more porcine in vivo matured oocytes activated following removal of ⅓ of the cytoplasm and replacement into the perivitelline space than unmanipulated oocytes. Our results are consistent with those of Lee et al. (1993). Although both manipulated and unmanipulated oocytes were treated similarly, an electroactivation pulse was also given. Similarly, in vivo matured bovine oocytes activated at higher rates following removal of a small piece of cytoplasm, replacement against the plasma membrane of another oocyte and electroactivation than electroactivated oocytes (Slapak and Westhusin, 1989).

The fourth experiment showed that the CYCLO treatment was an efficient method to obtain pronuclear stage cytoplasm since oocytes from this treatment activated at high rates (76%). Other researchers have reported a beneficial effect of culture in cycloheximide following electroactivation for IVM porcine oocytes (Nussbaum and Prather, 1995). Activation rates were higher for IVM oocytes from their study (92%) compared to in vivo matured oocytes from our study (76%). This suggests that components within the cytoplasm of IVM oocytes respond to these factors at higher rates. Without wishing to be bound by theory, it is believed that this difference in activation rate is largely due to the ability to time recovery of metaphase II oocytes better with an IVM system. More importantly, none of the activated oocytes formed two-cell parthenotes in the present study. This is essential to studies with NT because all of the enucleated oocytes can be utilized for these studies. However, the viability of this cytoplasm for NT embryo development remains to be determined. However, First et al. (1992) reported development to the morula and blastocyst stages of NT embryos produced from electroactivated and cycloheximide treated oocytes.

Protein synthesis inhibitors (cycloheximide and puromycin) alone have no beneficial effect on activation rates of IVM porcine oocytes (Nussbaum and Prather, 1995; Petr et al., 1996). This result is different from bovine (Yang et al., 1992b; Shi et al., 1993), murine (Siracusa et al., 1978; Clarke and Masui, 1983) and human (Balakier and Casper, 1993) oocytes. Species differences in response to protein synthesis inhibitors may suggest differences in the mechanism of activation between species. Cycloheximide in combination with Ca2+-ionophore (Shi et al., 1993) and ethanol (Yang et al., 1992b; Petr et al., 1996) have been successful activation methods. These activation methods should be tested with porcine oocytes to determine if they are equally successful.

It is generally thought that the mechanism for efficient activation of oocytes via this method (Pressice and Yang, 1994b) is as follows: electroactivation, ethanol or Ca2+-ionophore treatment induces a single Ca2+ peak resulting in CSF destruction; protein synthesis inhibitors prevent the synthesis of new CSF; absence of CSF results in cyclin B destruction; and MPF can not be formed since one of its subunits is not present. Because electroactivation alone does not result in a permanent decrease in MPF levels (Collas et al., 1993), a protein synthesis inhibitor may the key component to maintenance of basal MPF levels.

The ELECTRO treatment in this study only activated 49% of the oocytes and resulted in 33% two-cell parthenote formation. Electroactivation is the most common method of oocyte activation for mammalian oocytes. Electric shock produces a depolarization of the plasma membrane in a similar manner to sperm binding (Whittingham, 1980) and this triggers the subsequent cascade of events that have been previously discussed. Our activation rates for in vivo matured porcine oocytes (49%) were much lower than those reported for IVM oocytes (60 to 73%; Nussbaum and Prather, 1995; 96 to 100%; Kure-bayashi et al., 1996). Further, we detected no effect of electrical pulse (1.3 or 2.6 kV/cm) on activation rates. Prather et al. (1991c) reported that activation rates for IVM oocytes increased as electrical pulse increased from 70 to 120 V/mm. Our pulses were both higher, therefore the optimal activation rates may have been achieved at between 1.2 and 1.3 kV/cm. Activation rates of in vivo derived murine oocytes were unaffected by field strength from 2.4 to 3.6 kV/cm (Collas et al., 1989). Together, these results may indicate that IVM oocytes are more responsive to electroactivation. Perhaps the threshold for membrane depolarization is higher for in vivo matured oocytes than IVM oocytes.

Conclusions

Results from Experiment 1 indicated that ethanol treatment of in vivo matured porcine oocytes was unsuccessful in improving activation rates following 20 h of culture. Experiment 2 demonstrated that culture of in vivo matured oocytes at 25° C. resulted in higher activation rates than culture at 39° C. for 20 h. Following 20 h of culture in Experiment 3, sham enucleated oocytes activated at higher rates than control oocytes. Finally, these studies indicated that electroactivation followed by culture in the presence of cycloheximide for 24 h was the most efficient treatment for production of pronuclear stage cytoplasm.

Example 3

Three experiments were designed to examine the effects of different cytoplast stages on in vitro development of NT embryos produced from porcine ES cells. Procedures were followed as described previously (Prather et al., 1987) only using an ES cell as the karyoplast for NT embryo construction. These NT embryos were cultured for 96 h, in vitro, to examine development. The in vivo matured cytoplasts used in this study were: enucleated oocytes following 24 h of culture (high MPF; Experiment 1); enucleated oocytes following electroactivation and 24 h of culture in the presence of cycloheximide (low MPF; Experiment 2); and enucleated zygotes following 2 to 5 h of culture (low MPF; Experiment 3). In Experiment 1, the effects of electrical field strength (2.6 and 1.3 kV/cm) were also examined. In Experiment 1, NT embryos and NT controls (enucleated oocytes given a fusion pulse without injection of the ES cell) did not differ in their ability to develop to the two-, four- and eight-cell stages following 96 h of culture. Further, a higher field strength resulted in higher rates of lysis as well as development to all stages within NT embryo and NT control groups. However, no NT embryos developed to the compact morula stage. Similar results were determined for activated cytoplasts in Experiment 2 as indicated by no differences in developmental endpoint for NT embryos and controls. In Experiment 3, NT embryos developed to the compact morula stage following construction with an enucleated zygote as a cytoplast. Rates of embryo development to compact morulae after 96 h of in vitro culture were 55%, 15% and 5% for control embryos (unmanipulated zygotes), NT embryos and NT controls (enucleated zygotes given a fusion pulse without injection of an ES cell), respectively (P<0.10). Reasons for the success of zygotes could be that the exposure to cycloheximide was detrimental to the viability of the cytoplasm, MPF levels were not completely at basal levels or some sperm factor is essential to development of NT embryos. These results indicated which cytoplast was appropriate to promote in vitro development of NT embryos produced with porcine ES cells.

The in vivo matured cytoplasts used in this study were enucleated oocytes following 24 h of culture (high MPF); enucleated oocytes following electroactivation and 24 h of culture in the presence of cycloheximide (low MPF); and enucleated zygotes following 2 to 5 h of culture (low MPF).

In Experiment 1, oocytes were enucleated and cultured for 24 h prior to fusion with ES cells. Within this experiment, two fusion pulses (1.3 and 2.6 kV/cm) were examined. This experiment was designed to test the effect of cytoplasts with high levels of MPF on NT embryo development. Further, we tested the effect of fusion pulse on lysis and development of NT embryos. In Experiment 2, oocytes were enucleated, electroactivated and cultured for 24 h in the presence of cycloheximide prior to fusion with ES cell. The effect of cytoplasts with low levels of MPF (artificially induced) on NT embryo development was examined. In Experiment 3, zygotes were enucleated and cultured for 2 to 5 h prior to fusion with ES cells. This experiment was designed to examine the effect of cytoplasts with low levels of MPF (naturally induced) on NT embryo development.

Oocytes were collected in a variety of ways. Donor females were monitored twice daily for the onset of estrus by exposure to a mature boar. Oocytes were collected from non-mated gilts at 36 to 48 h after the onset of estrus. In some instances, gilts were given 500 IU hCG just prior to onset of estrus. Oocytes from these gilts were collected 40 to 44 h post-hCG. When possible, donor gilts were superovulated. One method was injection of non-cycling gilts with PG600 (Intervet America, Inc., Millsboro, Del.) which contains 400 IU eCG+200 IU hCG followed by 1,000 IU hCG 72 h later. Another method was injection of cycling gilts 16 d after the onset of estrus with eCG (1,000 IU) and hCG (1,000 IU) 72 h later. Mature, metaphase II oocytes were collected approximately 40 to 44 h following hCG injection. All zygotes were collected from donor females superovulated in the same manner (eCG+hCG 72 h later), however zygotes were flushed from oviducts at 54 to 56 h post-hCG. Oocytes and zygotes were flushed from oviducts with BECM (Dobrinsky et al., 1996). If necessary, cumulus cells were removed from oocytes by placing them in BECM+ hyaluronidase (3 mg/ml) and vortexing for 3 min.

In Experiment 1, oocytes were collected from one Meishan, four Duroc×Meishan, two Pietrain×Meishan, three Landrace×Duroc and four Yorkshire females. In Experiment 2, oocytes from four Duroc×Yorkshire, one Meishan and five Yorkshire females were recovered. In Experiment 3, zygotes were recovered from eight Duroc×Yorkshire, three Yorkshire×Duroc and one Duroc gilt, all of which were bred to a Yorkshire boar.

Oocytes were placed in enucleation medium which consisted of BECM+cytochalasin B (7.5 µg/ml). Oocytes were blindly enucleated by removing the first polar body and a portion of the surrounding cytoplasm on a heated stage (39° C.) with a Nikon Diaphot inverted microscope (magnification=100:1; Nikon Inc., Melville, N.Y.) fitted with micromanipulators (Narishige Co., Ltd., Tokyo, Japan) and a 20 to 30 µm (i.d.) beveled glass manipulating pipet according to procedures described by Prather et al. (1987). A 130 to 140 µm (i.d.) glass holding pipet was also used. The 500 µl holding and 100 µl enucleation syringes (Hamilton Co., Reno, Nev.) were filled with fluorinert (Sigma Chemical Co., St. Louis, Mo.). In a preliminary study, enucleation of Hoescht 33342 stained oocytes (n=9) resulted in a 89% enucleation efficiency as evidenced by examination under fluorescence.

Pronuclear zygotes were placed in 500 µl of BECM in a 1.5-ml microfuge tube and centrifuged at 16,000×g (Eppendorfcentrifuge 5415 C; Brinkman Instruments, Inc., Westbury, N.Y.) for 8 to 10 min according to procedures by Wall et al. (1985). This allowed visualization of pronuclei. Zygotes were placed in BECM+colchicine (0.1 µg/ml) for 2 min and then placed in micromanipulation medium (BECM+7.5 µg/ml cytochalasin B). A slightly larger pipet (30 to 40 µm; i.d.) as used for oocytes was inserted into the cytoplasm and both pronuclei were removed. The pronuclei could be visualized inside the pipet upon removal (magnification=200:1). In an independent study, five control zygotes were cultured alongside 25 enucleated zygotes. This resulted in one blastocyst out of 25 enucleated zygotes (96% enucleation rate) which developed similarly to control embryos.

In Example 4 we determined that culture of oocytes for 24 h resulted in the lowest activation rates whereas electroactivation and culture for 24 h in the presence of cycloheximide resulted in the highest activation rates. In Experiment 1 of this study, metaphase II oocytes were enucleated, washed three times in modified Whitten's medium+1.5% BSA (Beckmann and Day, 1993), placed in 50 µl drops of modified Whitten's medium+1.5% BSA under paraffin oil and cultured for 24 h in a 5% $CO_2$ in air environment at 39° C. In Experiment 2, metaphase II oocytes were enucleated, placed in electroactivation medium (0.3 M mannitol, 0.1 mM $MgSO_4$, 0.05 mM CaCl2; pH=7.2) to equilibrate, placed between two wire electrodes 1-mm apart (microslide 450; BTX Inc., San Diego, Calif.) in electroactivation medium, given a 30 μsec DC pulse (1.3 kV/cm) with a BTX Electro Cell Manipulator 200 (BTX Inc., San Diego, Calif.), washed three times with BECM and modified Whitten's medium+1.5% BSA+cycloheximide (5 μg/ml; Sigma Chemical Co., St. Louis, Mo.), placed into 50 μl drops of modified Whitten's medium+1.5% BSA+cycloheximide (5 μg/ml) under paraffin oil and cultured for 24 h at 39° C. in a humidified 5% $CO_2$ in air environment. In Experiment 3 of this study, zygotes were enucleated, washed three times in modified Whitten's medium+1.5% BSA, placed in 50 μl drops of modified Whitten's medium+1.5% BSA under paraffin oil and cultured for 2 to 5 h in a 5% $CO_2$ in air environment at 39° C.

Techniques for derivation of porcine ES cells have been previously reported (Wheeler, 1994; Gerfen and Wheeler, 1995; Wheeler et al., 1997). In Experiment 1, 12 different ES cell lines were used as karyoplasts in NT ranging in passage number from two to 16 passages. In Experiment 2, six different ES cell lines were used at seven to eight passages. In Experiment 3, three ES cell lines were used which ranged from seven to 20 passages. One line which was used for most of the replicates was transgenic, containing the bovine α-lactalbumin gene (Bleck and Bremel, 1993; Bleck et al., 1996), which allowed for PCR screening of resultant NT embryos to determine if they were ES cell-derived.

Colonies of ES cells were cultured in 60-mm tissue culture plates with STO feeder layers. Upon isolation, the ES cell culture medium was removed and the plate was overlaid with 3 ml of Ca2+- and Mg2+-free PBS for a few minutes. Next, the PBS was removed, 200 μl of trypsin/ethylenediaminetetraacetic acid (EDTA) solution (0.25% trypsin, 0.4% EDTA in Ca2+, Mg2+-free PBS, 1% NaCl, 0.025% KCl, 0.025% $KH_2PO_4$, and 0.114% $Na_2HPO_4$; wt/vol; pH=7.2) was put on the plate and 200 μl of trypsin was placed in a 1.5-ml microfuge tube. Embryonic stem cell colonies were plucked from the plate with a glass mouth pipet under a Nikon diaphot microscope and placed in the microfuge tube. The medium inside the microfuge tube was pipetted vigorously to break up colonies and filled to the top with BECM. The microfuge tube was centrifuged at 82×g for 5 min and media was removed from the pellet. Finally, the pellet was resuspended with 100 μl of BECM. A portion of this suspension was placed into a microdrop on a micromanipulation plate. The smallest (8 to 15 μm), roundest ES cells were used for transfer into cytoplasts.

A micromanipulation plate was used which contained two BECM microdrops under oil. One drop contained the ES cells and the other contained the cytoplasts. A single ES cell was removed with the injection pipet. Next, the micromanipulation pipets were moved to the other microdrop containing the cytoplasts. The cytoplasts were then grasped with the holding pipet. A single ES cell was placed, by micromanipulation, under the zona pellucida, adjacent to the vitelline membrane of each enucleated oocyte or zygote. Micromanipulation was performed on a heated stage (39° C.) with a Nikon diaphot microscope (Nikon Inc., Melville, N.Y.) equipped with Narishige micromanipulators (Narishige Co., Ltd., Tokyo, Japan) and a 10 to 20 μm (i.d.) micromanipulation pipet. A 30 to 40 μm (i.d.) holding pipet was also used. The 500 μl holding syringe was filled with fluorinert and the 500 μl injection syringe was filled with dimethylpolysiloxane (Sigma Chemical Co., St. Louis, Mo.) for better control.

Next, the ES cell-oocyte complexes were equilibrated in fusion medium (0.3 M mannitol, 0.1 mM $MgSO_4$, 0.05 mM $CaCl_2$; pH=7.2) and placed in fusion medium between two flat platinum electrodes spaced 1-mm apart (Microslide 450; BTX Inc., San Diego, Calif.). The ES cell-oocyte complexes were automatically oriented with a 5 V AC pulse for 10 sec so that the fusion plane was parallel to the electrodes. Following the alignment pulse, couplets were given one 1.3 kV/cm DC pulse for 80 μsec. Nuclear transfer controls (enucleated oocytes or zygotes) were exposed to the same pulse. A 2.6 kV/cm pulse was also examined in Experiment 1. Power to the fusion chamber was provided by a BTX Electro Cell Manipulator 200 (BTX Inc., San Diego, Calif.).

Following fusion, NT embryos were washed three times in BECM and modified Whitten's+1.5% BSA and placed in 50 μl drops of modified Whitten's medium+1.5% BSA under paraffin oil. Embryos were cultured in a 5% $CO_2$ in air environment at 39° C. Embryos were observed once a day for 96 h or until development ceased.

In Experiments 1, 2 and 3, the effect of treatment (NT embryos, NT controls and control embryos) on development in vitro was analyzed by chi-square (c2) analysis. In Experiment 1, the effect of field strength (1.3 and 2.6 kV/cm) was also examined by chi-square (c2) analysis.

In Experiment 1, fifteen replicates were completed, representing 97 NT embryos and 58 NT controls. An effect of field strength was detected within NT embryos and NT controls (P<0.10) for development to the two-, four- and eight-cell stages. Therefore, data for the two field strengths could not be combined. Enucleation rates of 71% (n=218) were determined by the number of unlysed (21% lysed) and unactivated (4%) oocytes prior to fusion. All cytoplasts activated prior to fusion in some replicates indicating that the oocytes had spontaneously activated before or immediately after retrieval. These data were not included in activation efficiency rates. Enucleation rates also varied between naturally-cycling and superovulated individuals.

Use of unactivated, metaphase II cytoplasm resulted in no development to compact morula and little development beyond the four-cell stage (Table 5.1). Further, no difference was detected between NT embryos and NT controls for development to the two-, four- and eight-cell stages. This would not allow developmental determination between NT embryos and controls. The furthest development of NT embryos was to the 16- to 32-cell stage in vitro.

TABLE 4

Effects of enucleated, unactivated oocytes on nuclear transfer embryo development following 96 hours of in vitro culture.

| | Fusion pulse | | | |
| | 2.6 kV/cm | | 1.3 kV/cm | |
| | Treatment | | | |
| Trait | NT embryos[a] | NT controls[a] | NT embryos[a] | NT controls[a] |
| --- | --- | --- | --- | --- |
| No. embryos | 72 | 25 | 50 | 8 |
| No. lysed | 35 (49%) | 8 (32%) | 8 (16%) | 0 (0%) |
| No. two-cell embryos | 21 (29%) | 5 (20%) | 22 (44%) | 4 (50%) |
| No. four-cell embryos | 14 (19%) | 2 (8%) | 19 (38%) | 4 (50%) |
| No. eight-cell embryos | 6 (6%) | 0 (0%) | 8 (16%) | 3 (38%) |

[a]NT = nuclear transfer.

Upon combination of NT embryos and NT controls, a field strength of 2.6 kV/cm resulted in much higher lysis rates than a field strength of 1.3 kV/cm (44 and 14%, respectively; P<0.001). Further, development to the two-, four- and eight cell stages were higher with a field strength of 2.6 kV/cm compared to 1.3 kV/cm (P<0.10).

Experiment 2

A total of 11 replicates were performed which represented 43 NT embryos and 24 NT controls. Enucleation rates of 61% (n=114) were determined by the number of unlysed (17% lysed) and unactivated (22%) oocytes prior to fusion. Use of activated, enucleated oocytes as cytoplasts resulted in no development to compact morula stage and little development beyond the four-cell stage. Similarly to Experiment 1, rates of development to the two-, four- and eight-cell stage were not different between NT embryos and NT controls (P>0.15; Table 5).

Experiment 3

Figure 11C:
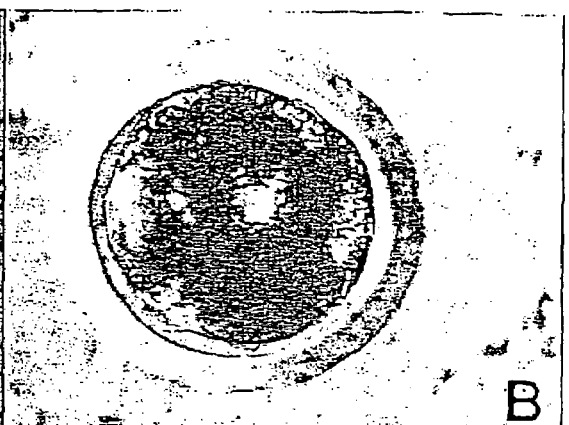
Figure 11C:
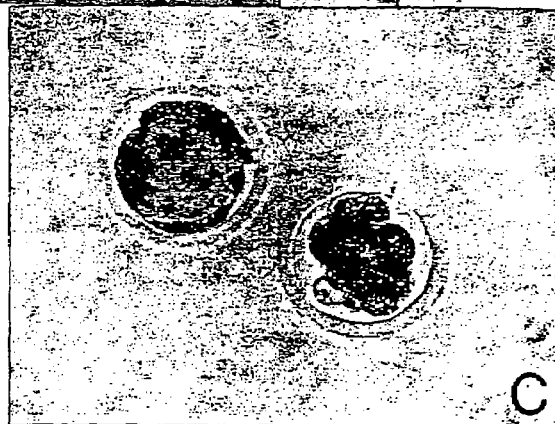

Enucleation rate (n=208) was 73% as indicated by the number of unactivated (9% activated) and unlysed (18% lysed) zygotes prior to fusion. In Experiment 3, a total of 12 replicates were performed including 89 NT embryos, 44 NT controls and 45 control embryos. Indicative of an appropriate culture system, more control embryos developed to the four-cell, eight-cell and compact morula stages following 96 h of culture than NT embryos or NT controls (P<0.05; Table 4). No difference was detected between NT embryos and NT controls for development to the four- and eight-cell stages (P>0.10). A higher percentage of NT embryos developed to the compact morula stage following 96 h of culture than NT controls (P<0.10). Use of enucleated pronuclear zygotes resulted in NT embryo development beyond the four-cell stage to the compact morula and blastocyst stages (FIG. 11). Since control embryos were cultured along with NT embryos, a proper developmental comparison could be made within each replicate. A few NT control embryos did develop to the compact morula stage within our study. However, in each of these replicates, some problems were encountered with the enucleation process. The most

TABLE 5

Effects of enucleated, activated oocytes on nuclear transfer embryo development following 96 hours of in vitro culture.

| Trait | Treatment | |
|---|---|---|
| | NT embryos[a] | NT controls[a] |
| No. embryos | 43 | 24 |
| No. lysed | 1 (2%) | 0 (0%) |
| No. two-cell embryos | 8 (19%) | 7 (29%) |
| No. four-cell embryos | 3 (7%) | 4 (17%) |
| No. eight-cell embryos | 0 (0%) | 1 (4%) |

[a]NT = nuclear transfer.

TABLE 6

Effects of Enucleated Zygotes on Nuclear Transfer Embryo Development Following 96 Hours of in vitro Culture

| Trait | Treatment | | |
|---|---|---|---|
| | NT embryos[a] | NT controls[a] | Control embryos |
| No. embryos | 89 | 44 | 45 |
| No. lysed | 10[b] (11%) | 5[b] (11%) | 0[c] (0%) |

TABLE 6-continued

Effects of Enucleated Zygotes on Nuclear Transfer Embryo Development Following 96 Hours of in vitro Culture

| Trait | Treatment | | |
|---|---|---|---|
| | NT embryos[a] | NT controls[a] | Control embryos |
| No. 4-cell embryos | 53[b] (60%) | 24[b] (55%) | 37[c] (82%) |
| No. 8-cell embryos | 32[b] (36%) | 10[b] (23%) | 34[c] (76%) |
| No. compact morulae | 13[b] (15%) | 2[c] (5%) | 25[d] (56%) |

[a]NT = nuclear transfer.
[b,c,d]Means within a row with different superscripts differ (P < .10).

appropriate zygotes for enucleation had pronuclei visible at a lower magnification (100:1) following centrifugation. However, in the replicates which produced NT control development, the pronuclei only became visible at a higher magnification (200:1). Zygotes were not centrifuged for longer times to minimize lysis.

The effectiveness of enucleated zygotes as cytoplasts over unactivated or activated oocytes was surprising. Unlike zygotes from mice, zygotes from cattle, sheep and pigs must be manipulated to visualize pronuclei. Therefore, metaphase II oocytes have primarily been used as cytoplasts in these species. Only unactivated, metaphase II oocytes have been used as cytoplasts in porcine NT whereas enucleated zygotes have been used as cytoplasts only in porcine pronuclear exchange (Prather et at., 1989). Studies in cattle (Prather et al., 1987; Robl et al., 1987), mice (Cheong et al., 1993; McGrath and Solter, 1984) and rabbits (Modlinski and Smorag, 1991) suggest that oocytes are better cytoplasts than zygotes. In murine serial NT studies, however, Kwon and Kono (1996) reported reduced developmental rates when cytoplasts were derived from activated oocytes compared to zygotes. Further, comparison of enucleated zygotes and activated, enucleated oocytes as cytoplasts did not reveal differences in bovine NT embryo development (Stice et al., 1994). Three possible explanations for our results are our oocyte activation method did not result in a complete decrease of MPF to basal levels whereas zygotes had basal MPF levels; our activation method had adverse effects on the viability of the cytoplasm for NT embryo development; and some component of the sperm is essential to promote and(or) maintain development of NT embryos.

Activated oocytes in Experiment 2 did not promote NT embryo development to compact morulae. Although electroactivation and culture in the presence of cycloheximide was an efficient method to obtain pronuclear stage cytoplasm, it may have hindered the viability of the cytoplasm for NT embryo development. Bovine NT embryos produced from electroactivated and cycloheximide treated oocytes developed to the morula and blastocyst stages (First et al., 1992). Although these investigators used slightly higher levels of cycloheximide (101 g/ml), cytoplasts were only cultured for 4 h in cycloheximide. Nussbaum and Prather (1995) determined similar activation rates for electroactivated oocytes cultured in cycloheximide (5 μg/ml) for 6 or 24 h. We cultured electroactivated oocytes in cycloheximide for 24 h which may have been too long. Culture in the presence of cycloheximide for a shorter period of time may benefit NT embryo development when these oocytes are used as cytoplasts. In addition, cytoplasm from bovine oocytes may respond better to cycloheximide treatment than cytoplasm from porcine oocytes. The 24 h culture of oocytes may have been detrimental to NT embryo development also.

Kim et al. (1996c) reported that aged porcine IVM oocytes had disrupted microfilaments which hinder development following parthenogenetic activation. Defects in cytoskeletal structure have previously been shown in murine oocytes (Webb et al., 1986). Further, enucleation rates decrease with oocyte aging (Takano et al., 1993). Therefore, ploidy problems could have resulted in NT embryos. However, bovine NT embryo development is improved when aged oocytes are used as cytoplasts (Ware et al., 1989).

After enucleation, the ES cells are placed inside the perivitelline space of cytoplasts and the complexes are fused the following day. It is possible that the micromanipulation and aging processes activate the oocytes. Reports have shown that micromanipulation and aging will stimulate activation (Markert, 1982; Ware et al., 1989). The presence of two-, four-, and eight-cell parthenotes the following morning probably indicates that some activation had occurred in oocytes that were not completely enucleated. These methods have been successful in bovine NT studies (Sims and First, 1993). However, percentages of activation need to be determined in a preliminary experiment for sham enucleated oocytes cultured overnight. The enucleation process, exposure to cytochalasin B and time outside $CO_2$ environment may have a cumulative effect on activation rates. Therefore, an effect on NT embryo development would be expected.

The lack of development of NT embryos in Experiment 1 and 2 produced from enucleated oocytes was unexpected. Others have obtained blastocyst development from NT with two-, four-, eight- and 16-cell karyoplasts (Prather et al., 1989; Nagashima et al., 1992; Terlouw et al., 1992). Differences in results between studies could be due to potency differences in karyoplasts, use of aged oocytes vs freshly ovulated oocytes or differences in NT technique. However, the success of zygotic cytoplasts in Experiment 3 suggest that the combination of ES cell karyoplasts and zygotic cytoplasts are critical to development. This is the first report, to our knowledge, of development beyond the four-cell stage for porcine NT embryos produced from ES cells. A model of the procedures used to obtain in vitro development of NT embryos produced from porcine ES cells is depicted in FIG. 5.2.

Conclusions

Results from Experiment 1 indicated that the use of enucleated, unactivated oocytes as cytoplasts did not promote development of NT embryos beyond the four-cell stage. Similarly, results from Experiment 2 indicated that the use of enucleated, activated oocytes as cytoplasts was unsuccessful in promoting development of NT embryos beyond the four-cell stage. However, the use of enucleated zygotes as cytoplasts in Experiment 3 resulted in development of NT embryos beyond the four-cell stage. The methods described herein allow production of genetically identical pigs from ES cell lines in the future.

Production of transgenic animals, especially large domestic animals, has been extremely inefficient (1 to 10%) and expensive ($25,000 per animal for swine). The possible use of ES cells to produce transgenic animals provides a unique opportunity to increase the efficiency and decrease the cost of transgenic pig production as well as provide more stable gene integration. However, live animals have never been produced by NT with ES cells and embryo development has only been reported in mice and rabbits. In addition, only one live piglet has been born via NT. Part of the difficulty with NT procedures is the synchronization of karyoplast and cytoplast cell cycles. One method to alleviate these problems is to use activated cytoplasts. This methodology will allow the use of karyoplasts from any stage of the cell cycle.

The first step in the production of live pigs from NT with porcine ES cells is to obtain embryo development of these NT embryos. Three experiments needed to be performed to achieve this goal. The experiments were development of an appropriate culture system to obtain development of one-cell porcine embryos to the blastocyst stage, determination of an efficient method for activation of in vivo matured porcine oocytes and determination of the appropriate stage of cytoplast for in vitro development of NT embryos beyond the four-cell stage. Results from these studies provide the methods for in vitro development of NT embryos from porcine ES cells.

Results from Example 1 indicated that W-BSA was the most efficient medium for culture of four- and eight-cell Meishan embryos to the blastocyst stage and some component of W-FBS was necessary for hatching of later stage Meishan embryos. Fatty acid-free BSA is not necessary for in vitro culture of early stage porcine embryos. Following 96 h of culture, more Meishan one-cell embryos developed to the eight-cell and compact morula stages than Yorkshire one-cell embryos. More Yorkshire two-cell embryos developed to the eight-cell stage than Meishan two-cell embryos following 96 h of culture whereas no breed differences were detected for four-cell embryo development to any stage following a 96 h culture period. Finally, these studies indicate the need for further investigation into dynamic culture systems instead of static systems.

Results from Example 2 indicated that ethanol treatment of in vivo matured porcine oocytes did not improve activation rates following 20 h of culture. Culture of in vivo matured oocytes at 25° C. resulted in higher activation rates than culture at 39° C. for 20 h. Following 20 h of culture, sham enucleated oocytes activated at higher rates than control oocytes. Finally, electroactivation followed by culture in the presence of cycloheximide for 24 h was the most efficient treatment for production of pronuclear stage cytoplasm.

Results from Experiment 3 indicated that the use of enucleated, unactivated oocytes as cytoplasts did not promote development of NT embryos beyond the four-cell stage. Similarly, the use of enucleated, activated oocytes as cytoplasts was unsuccessful in promoting development of NT embryos beyond the four-cell stage. However, the use of enucleated zygotes as cytoplasts resulted in development of NT embryos beyond the four-cell stage. These methods should provide useful information toward the production of genetically identical pigs from ES cell lines in the future.

In conclusion, the use of enucleated zygotes as cytoplasts promoted development of NT embryos beyond the four-cell stage to the compact morula stage. Next, a number of steps need to be determined to produce transgenic pigs from ES cells including the technology to produce liveborn piglets from NT embryos improvement of developmental efficiencies for NT embryos, improvement of DNA transfection procedures for porcine ES cells and production of live pigs from genetically modified ES cells.

Example 5

As an extension of the data described herein above, we have also completed genetic screens of those embryos. To determine the efficiency of NT embryo production, we performed PCR followed by Southern blotting to identify the genetic make up of the NT embryos. The ES cell line used in this study was derived from an individual carrying a transgene encoding α-lactalbumin. The lactalbumin construct is described in Bleck et. (1994) J. Dairy Sci. 77:1897-1904; and Bleck et al. (1993) J. Anim. Sci. 76:3072-3078. Therefore, NT embryos should be positive for the transgene. In addition, the NT controls were analyzed using a microsatellite marker specific for porcine DNA to determine if they wee actually enucleated.

TABLE 7

Summary of genetic screening of nuclear transfer (NT), NT control (NTC) and control (CNTRL) embryos for the presence of the α-lactalbumin gene and a microsatellite marker for porcine genomic DNA.

| Treatment | No. of embryos | Percentage of embryos positive for α-lactalbumin | Percentage of embryos positive for genomic DNA |
| --- | --- | --- | --- |
| NT | 31 | 19% | 52% |
| NTC | 21 | 23% | 32% |
| CNTRL | 10 | 50% | 90% |

TABLE 8

Raw data from genetic screening of nuclear transfer (NT), NT control (NTC) and control (CNTRL) embryos for the presence of the α-lactalbumin (α-Lac) gene and a microsatellite marker for porcine genomic DNA.

| Pig ID | Treatment | Stage of embryo | α-Lac | Porcine genomic DNA |
| --- | --- | --- | --- | --- |
| 2552 | NTC | 8-16 | Neg | Neg |
| 2552 | NTC | 4-8 | Neg | Neg |
| 2552 | CNTRL | CM | Neg | Neg |
| 2552 | NT | CM | Pos | Pos |
| 2552 | NT | CM | Neg | Pos |
| 2552 | NTC | 4 | Neg | Pos |
| 2552 | NT | 4 | Neg | Neg |
| 2511 | NT | CM | Pos | Pos |
| 2511 | NT | M | Pos | Pos |
| 2511 | NT | 8-16 | Neg | Pos |
| 2511 | NT | 4 | Neg | Pos |
| 2511 | NT | CM | Neg | Pos |
| 2511 | NT | CM | Neg | Pos |
| 2511 | NT | 4 | Neg | Pos |
| 2511 | NT | CM | Neg | Neg |
| 2511 | NTC | 4 | Neg | Pos |
| 2511 | NTC | 4-8 | Neg | Neg |
| 2511 | NTC | CM | Pos | Pos |
| 2511 | NTC | 1 | Pos | Neg |
| 6540 | NT | 4 | Neg | Neg |
| 6540 | NT | 8-16 | Neg | Neg |
| 6540 | NT | 4 | Neg | pos |
| 6540 | NT | 4 | Neg | Neg |
| 6540 | NT | 4-8 | Neg | Pos |
| 6540 | NT | 4 | Pos | Pos |
| 6540 | NT | 8-16 | Neg | Neg |
| 6540 | NT | 1 | Neg | Neg |
| 6540 | NT | 8-16 | Neg | Neg |
| 6540 | NT | 4 | Neg | Neg |
| 6540 | NTC | 2 | Neg | Pos |
| 6540 | NTC | 8-16 | Neg | Neg |
| 6540 | NTC | 2 | Neg | Pos |
| 6540 | NTC | 4 | Neg | Pos |
| 6540 | NTC | 2 | Pos | Neg |
| 6540 | NTC | 4 | Neg | Neg |
| 6540 | NTC | 4 | Neg | Neg |
| 6540 | CNTRL | CM | Pos | Pos |
| 6540 | CNTRL | CM | Pos | Pos |
| 6540 | CNTRL | CM | Neg | Pos |
| 4531 | NTC | 4 | Pos | Neg |
| 4531 | NTC | 1 | Neg | Pos |
| 4531 | NTC | 4 | Pos | Pos |
| 4531 | NT | 2 | Neg | Neg |
| 4531 | NT | 2 | Neg | Neg |
| 4526 | NT | 2 | Pos | Pos |
| 4526 | NT | CM | Neg | Pos |
| 4526 | NTC | 1 | Neg | Pos |
| 6503 | NT | 16 | Neg | Neg |
| 6503 | CNTRL | CM | Pos | Pos |
| 6503 | NTC | 4-8 | Pos | Pos |
| 6503 | CNTRL | CM | Pos | Pos |
| 6503 | NTC | 4-8 | Pos | Neg |
| 6503 | NT | CM | Neg | Neg |
| 6503 | NT | 8 | Neg | Neg |
| 6503 | NT | CM | Neg | Pos |
| 6503 | CNTRL | CM | Pos | Pos |
| 6503 | NTC | 1 | Neg | Neg |
| 6503 | NT | CM | Pos | Neg |
| 6503 | CNTRL | CM | Neg | Pos |
| 6540 | CNTRL | CM | Neg | Pos |
| 6540 | CNTRL | CM | Neg | Pos |

LITERATURE CITED

Allen, R. L., and R. W. Wright, Jr. 1984. In vitro development of porcine embryos in co-culture with endometrial cell monolayers or culture supernatants. J. Anim. Sci. 59:1657-1661.

Anderson, G. B. 1992. Isolation and use of embryonic stem cells from livestock species. Anim. Biotechnology 3:165-175.

Anderson, G. B., S. J. Choi, and R. H. BonDurant. 1994. Survival of porcine inner cell masses in culture and after injection into blastocysts. Theriogenology 42:204-212.

Archibong, A. E., R. M. Petters, and B. H. Johnson. 1989. Development of porcine embryos from one- and two-cell stages to blastocysts in culture medium supplemented with porcine oviductal fluid. Biol. Reprod. 41:1076-1083.

Austin, C. R. 1956. Activation of eggs by hypothermia in rats and hamsters. J. Exp. Biol. 33:338-347.

Balakier, H., and R. F. Casper. 1993. Experimentally induced parthenogenetic activation of human oocytes. Hum. Reprod. 8:740-743.

Barnes, F. L., J. M. Robl, and N. L. First. 1987. Nuclear transplantation in mouse embryos: Assessment of nuclear function. Biol. Reprod. 36:1267-1274.

Barnes, F. L., P. Collas, R. Powell, W. A. King, M. Westhusin, and D. Shepherd. 1993. Influence of recipient oocyte cell cycle stage on DNA synthesis, nuclear envelope breakdown, chromosome constitution, and development in nuclear transplant bovine embryos. Mol. Reprod. Dev. 36:33-41.

Batt, P. A., D. K. Gardner, and A. W. N. Cameron. 1991. Oxygen concentration and protein source affect the development of preimplantation goat embryos in vitro. Reprod. Fertil. Dev. 3:601-607.

Batt, P. A., and B. G. Miller. 1988. Development of sheep embryos in vitro in a medium supplemented with different batches of serum albumin. Aust. J. Biol. Sci. 41:371-376.

Beckmann, L. S., and B. N. Day. 1993. Effects of media NaCl concentration and osmolarity on the culture of early-stage porcine embryos and the viability of embryos cultured in a selected superior medium. Theriogenology 39:611-622.

Bleck, G. T., and R. D. Bremel. 1993. Sequence and single-base polymorphisms of the bovine a-lactalbumin 5' flanking region. Gene 126:213-218.

Bradley, A. 1987. Production and analysis of chimaeric mice. In: E. J. Robertson (Ed.) Teratocarcinomas and Embryonic Stem Cells: A Practical Approach. pp. 113-151. IRL Press, Oxford, UK.

Bradley, A., M. Evans, M. H. Kaufman, and E. Robertson. 1984. Formation of germ-line chimaeras from embryo-derived teratocarcinoma cell lines. Nature 309:255-256.

Bradshaw, J., T. Jung, J. Fulka Jr., and R. M. Moor. 1995. UV irradiation of chromosomal DNA and its effect upon MPF and meiosis in mammalian oocytes. Mol. Reprod. Dev. 41:503-512.

Brem, G., B. Brenig, H. M. Goodman, R. C. Selden, F. Graf, B. Kruff, K. Springmann, J. Hondele, J. Meyer, E.-L. Winnacker, and H. Kraublich. 1985. Production of transgenic mice, rabbits and pigs by microinjection into pronuclei. Zuchthygiene 20:241-252.

Campbell, K. H. S., P. Loi, P. Cappai, and I. Wilmut. 1994. Improved development to blastocyst of ovine nuclear transfer embryos reconstructed during the presumptive S-phase of enucleated activated oocytes. Biol. Reprod. 50:1385-1393.

Campbell, K., and I. Wilmut. 1994. Recent advances on in vitro culture and cloning of ungulate embryos. Proceedings of the 5th International Congr. on Genetics Applied to Livestock Production 20:180-187.

Campbell, K., and I. Wilmut. 1997. Totipotency or multipotentiality of cultured cells: Applications and progress. Theriogenology 47:63-72.

Campbell, K. H. S., J. McWhir, W. A. Ritchie, and I. Wilmut. 1996a. Sheep cloned by nuclear transfer from a cultured cell line. Nature 380:64-66.

Campbell, K. H. S., P. Loi, P. J. Otaegui, and I. Wilmut. 1996b. Cell cycle co-ordination in embryo cloning by nuclear transfer. Rev. Reprod. 1:40-46.

Capecchi, M. R. 1989. Altering the genome by homologous recombination. Science 244:1288-1292.

Chang, D. C. 1992. Design of protocols for electroporation and electrofusion: selection of electrical parameters. In: D. C. Chang, B. M. Chassy, J. A. Saunders and A. E. Sowers (Ed.) Guide to Electroporation and Electrofusion. pp. 429-455. Harcourt Brace Jovanovich, San Diego, Calif.

Chastant, S., E. Christians, E. Campion, and J.-P. Renard. 1996. Quantitative control of gene expression by nucleocytoplasmic interactions in early mouse embryos: Consequence for reprogrammation by nuclear transfer. Mol. Reprod. Dev. 44:423-432.

Chastant, S., P. Monget, and M. Terqui. 1994. Localization and quantification of insulin-like growth factor-I (IGF-I) and IGF-II/mannose-6-phosphate (IGF-II/M6P) receptors in pig embryos during early pregnancy. Biol. Reprod. 51:588-596.

Chatot, C. L., C. A. Ziomek, B. D. Bavister, J. L. Lewis, and I. Torres. 1989. An improved culture medium supports development of random-bred 1-cell mouse embryos in vitro. J. Reprod. Fertil. 86:679-688.

Cheong, H. T., and H. Kanagawa. 1993. Assessment of cytoplasmic effects on the development of mouse embryonic nuclei transferred to enucleated zygotes. Theriogenology 39:451-461.

Cheong, H. T., Y. Takahashi, and H. Kanagawa. 1992. Development of mouse embryonic nuclei transferred to enucleated oocytes and zygotes. Jpn. J. Vet. Res. 40:149-159.

Cheong, H. T., Y. Takahashi, and H. Kanagawa. 1993. Birth of mice after transplantation of early cell-cycle-stage embryonic nuclei into enucleated oocytes. Biol. Reprod. 48:958-963.

Cheong, H. T., Y. Takahashi, and H. Kanagawa. 1994. Relationship between nuclear remodeling and subsequent development of mouse embryonic nuclei transferred to enucleated oocytes. Mol. Reprod. Dev. 37:138-145.

Cibelli, J. B., S. L. Stice, J. J. Kane, P. G. Golueke, J. Jerry, E. S. Dickinson, X. Y. Gao, A. Ponce de Leon, and J. M. Robl. 1997. Production of germline chimeric bovine fetuses from transgenic embryonic stem cells. Theriogenology 47:241 (Abstr.).

Collas, P., C. Pinto-Correia, F. A. Ponce De Leon, and J. M. Robl. 1992. Effect of donor cell cycle stage on chromatin and spindle morphology in nuclear transplant rabbit embryos. Biol Reprod. 46:501-511.

Collas, P., and F. L. Barnes. 1994. Nuclear transplantation by microinjection of inner cell mass and granulosa cell nuclei. Mol. Reprod. Dev. 38:264-267.

Collas, P., J. J. Balise, G. A. Hofmann, and J. M. Robl. 1989. Electrical activation of mouse oocytes. Theriogenology 32:835-844.

Collas, P., J. J. Balise, and J. M. Robl. 1992b. Influence of cell cycle stage of the donor nucleus on development of nuclear transplant rabbit embryos. Biol Reprod. 46:492-500.

Collas, P., and J. M. Robl. 1990. Factors affecting the efficiency of nuclear transplantation in the rabbit embryo. Biol Reprod. 43:877-884.

Collas, P., and J. M. Robl. 1991a. Development of rabbit nuclear transplant embryos from morula and blastocyst stage donor nuclei. Theriogenology 35:190 (Abstr.).

Collas, P., and J. M. Robl. 1991b. Relationship between nuclear remodeling and development in nuclear transplant rabbit embryos. Biol. Reprod. 45:455-465.

Cuthbertson, K. S. R. 1983. Parthenogenetic activation of mouse oocytes in vitro with ethanol and benzyl alcohol. J. Exp. Zool. 226:311-314.

Czolowska, R., J. A. Modlinski, and A. K. Tarkowski. 1984. Behaviour of thymocyte nuclei in nonactivated and activated mouse oocytes. J. Cell Sci. 69:19-34.

Davis, D. L. 1985. Culture and storage of pig embryos. J. Reprod. Fertil. Suppl. 33:115-124.

Davis, D. L., and B. N. Day. 1978. Cleavage and blastocyst formation by pig eggs in vitro. J. Anim. Sci. 46:1043-1053.

Delhaise, F., F. J. Ectors, R. De Roover, F. Ectors, and F. Dessy. 1995. Nuclear transplantation using bovine primordial germ cells from male fetuses. Reprod. Fertil. Dev. 7:1217-1219.

Didion, B. A., M. J. Martin, and C. L. Markert. 1990. Parthenogenetic activation of mouse and pig oocytes matured in vitro. Theriogenology 33:1165-1175.

Dobrinsky, J. R., L. A. Johnson, and D. Rath. 1996. Development of a culture medium (BECM-3) for porcine embryos: Effects of bovine serum albumin and fetal bovine serum on embryo development. Biol. Reprod. 55:1069-1074.

Doetschman, T. C., H. Eistetter, M. Katz, W. Schmidt, and R. Kemler. 1985. The in vitro development of blastocyst-derived embryonic stem cell lines: formation of visceral yolk sac, blood islands and myocardium. J. Embryol. Exp. Morphol. 87:27-45.

Doetschman, T., P. Williams, and N. Maeda. 1988. Establishment of hamster blastocyst-derived embryonic stem (ES) cells. Dev. Biol. 127:224-227.

Du, F., J. R. Giles, R. H. Foote, K. H. Graves, X. Yang, and R. W. Moreadith. 1995a. Nuclear transfer of putative rabbit embryonic stem cells leads to normal blastocyst development. J. Reprod. Fertil. 104:219-223.

Du, F., S. Jiang, and X. Yang. 1995b. Beneficial effect of oocyte activation prior to and during nuclear transfer in cattle using in vitro matured oocytes 24 h of age. Reprod. Nutr. Dev. 35:703-712.

Eberhardt, D. M., D. M. Henricks, J. F. Dickey, and J. R. Diehl. 1994. Oviductal fluid and growth factors failed to enhance development of porcine embryos. Theriogenology 41:1163-1172.

Ebert, K. M., and V. E. Papaioannou. 1989. In vivo culture of embryos in the immature mouse oviduct. Theriogenology 31:299-308.

Evans, M. J., and M. H. Kaufman. 1981. Establishment in culture of pluripotential cells from mouse embryos. Nature (Lond.) 292:154-156.

Evans, M. J. 1987. Formation of germ-line chimaeras from embryo-derived cell lines. 3rd Int. Sym. on Cellular Endocrinol., Lake Placid, N.Y.

First, N. L., M. L. Leibfried-Rutledge, D. L. Northey, and P. R. Nuttleman. 1992. Use of in vitro matured oocytes 24 hr of age in bovine nuclear transfer. Theriogenology 37:211 (Abstr.).

Fischberg, M., J. B. Gurdon, and T. R. Elsdale. 1958. Nuclear transplantation in *Xaenopus laevis.* Nature (Lond.) 181:424.

Flood, M. R., and J. L. Wiebold. 1988. Glucose metabolism by preimplantation pig embryos. J. Reprod. Fertil. 84:7-12.

Fulka, J., Jr., N. First, and R. M. Moor. 1996. Nuclear transplantation in mammals: remodeling of transplanted nuclei under the influence of maturation promoting factor. BioEssays 18:835-840.

Fulka, J., Jr., N. Ouhibi, R. M. Moor, and J. Fulka. 1994. Nuclear transplantation in mammals: The role of maturation promoting factor. Reprod. in Domest. Anim. 29:352-353.

Fulka, J., Jr., and R. M. Moor. 1993. Noninvasive chemical enucleation of mouse oocytes. Mol. Reprod. Dev. 34:427-430.

Gall, L., T. Dedieu, P. Chesne, S. Ruffini, C. Sevellec, N. Peynot, J. P. Renard, and Y. Heyman. 1996. Bovine embryo cloning: Characterization of the recipient cytoplasts by phosphorylation patterns and kinase activities. Develop. Growth Differ. 38:517-525.

Gardner, R. L. 1968. Mouse chimeras obtained by the injection of cells into the blastocyst. Nature (Lond.) 220:596-597.

Gerfen, R. W., and M. B. Wheeler. 1995. Isolation of embryonic cell-lines from porcine blastocysts. Anim. Biotechnology 6:1-14.

Gordon, J. W., and F. H. Ruddle. 1981. Integration and stable germ line transmission of genes injected into mouse pronuclei. Science 214:1244-1246.

Gossler, A., T. Doetschman, R. Korn, E. Serfling, and R. Kemler. 1986. Transgenesis by means of blastocyst-derived embryonic stem cell lines. Proc. Natl. Acad. Sci. USA 83:9065-9069.

Graves, K. H., and R. W. Moreadith. 1993. Derivation and characterization of putative pluripotential embryonic stem cells from preimplantation rabbit embryos. Mol. Reprod. Dev. 36:424-433.

Grocholova, R., J. Petr, J. Rozinek, and F. Jilek. 1997. The protein phosphatase inhibitor okadaic acid inhibits exit from Metaphase II in parthenogenetically activated pig oocytes. J. Exp. Zool. 277:49-56.

Hagen, D. R., R. S. Prather, M. M. Sims, and N. L. First. 1991a. Development of one-cell porcine embryos to the blastocyst stage in simple media. J. Anim. Sci. 69:1147-1150.

Hagen, D. R., R. S. Prather, and N. L. First. 1991b. Response of porcine oocytes to electrical and chemical activation during maturation in vitro. Mol. Reprod. Dev. 28:70-73.

Hammer, R. E., V. G. Pursel, C. E. Rexroad, Jr., R. J. Wall, D. J. Bolt, K. M. Ebert, R. D. Palmiter, and R. L. Brinster. 1985. Production of transgenic rabbits, sheep and pigs by microinjection. Nature (Lond.) 315:680-683.

Handyside, A., M. L. Hooper, M. H. Kaufman, and I. Wilmut. 1987. Towards the isolation of embryonal stem cell lines from the sheep. Roux's Arch. Dev. Biol. 196:185-190.

Holden, C. 2003. Genetics. First cloned mule races to finish line. Science 300:1354.

Howlett, S. K., S. C. Barton, and M. A. Surani. 1987. Nuclear cytoplasmic interactions following nuclear transplantation in mouse embryos. Development 101:915-923.

Hyttel, P., R. Prochazka, S. Smith, J. Kanka, and T. Greve. 1993. RNA synthesis in porcine blastomere nuclei introduced into in vitro matured ooplasm. Acta Vet. Scand. 34:159-167.

Iannaccone, P. M., G. U. Tabom, R. L. Garton, M. D. Caplice, and D. R. Brenin. 1994. Pluripotent embryonic stem cells from the rat are capable of producing chimeras. Dev. Biol. 163:288-292.

Illmensee, K., and P. Hoppe. 1981. Nuclear transplantation in *Mus musculus:* developmental potential of nuclei from preimplantation embryos. Cell 23:9-18.

Jarrell., V. L., B. N. Day, and R. S. Prather. 1991. The transition from maternal to zygotic control of development occurs during the 4-cell stage in the domestic pig, Sus scrofa: quantitative and qualitative aspects of protein synthesis. Biol. Reprod. 44:62-68.

Johnson, M. H., and C. A. Ziomek. 1981. The function of two distinct cell lineages within the mouse morula. Cell 24:71-80.

Kane, M. T. 1983. Variability in different lots of commercial bovine serum albumin affects cell multiplication and hatching of rabbit blastocysts in culture. J. Reprod. Fertil. 69:555-558.

Kanka, J., J. Fulka Jr., J. Fulka, and J. Petr. 1991. Nuclear transplantation in bovine embryo: Fine structural and autoradiographic studies. Mol. Reprod. Dev. 29:110-116.

Kanka, J., P. Hozak, Y. Heyman, P. Chesne, J. Degrolard, J.-P. Renard, and J.-E. Flechon. 1996. Transcriptional activity and nucleolar ultrastructure of embryonic rabbit nuclei after transplantation to enucleated oocytes. Mol. Reprod. Dev. 43:135-144.

Kashiwazaki, N., H. Nakao, S. Ohtani, and N. Nakatsuji. 1992. Production of chimeric pigs by the blastocyst injection method. Vet. Rec. 130:186-187.

Keefer, C. L., and S. L. Stice. 1992. In vitro culture of bovine nucleus transfer embryos. Biol. Reprod. 46 (Suppl. 1): 166 (Abstr.).

Keefer, C. L., S. L. Stice, and D. L. Matthews. 1994. Bovine inner cell mass cells as donor nuclei in the production of nuclear transfer embryos and calves. Biol. Reprod. 50:935-939.

Kim, N.-H., C. Simerly, H. Funahashi, G. Schatten, and B. N. Day. 1996a. Microtubule organization in porcine oocytes during fertilization and parthenogenesis. Biol. Reprod. 54:1397-1404.

Kim, N.-H., H. Funahashi, R. S. Prather, G. Schatten, and B. N. Day. 1996b. Microtubule and microfilament dynamics in porcine oocytes during meiotic maturation. Mol. Reprod. Dev. 43:248-255.

Kim, N.-H., S. J. Moon, R. S. Prather, and B. N. Day. 1996c. Cytoskeletal alteration in aged porcine oocytes and parthenogenesis. Mol. Reprod. Dev. 43:513-518.

Kono, T., O. Y. Kwon, and T. Nakahara. 1991a. Production of identical twin and triplet mice by nuclear transplantation. J. Exp. Zool. 257:214-219.

Kono, T., O. Y. Kwon, and T. Nakahara. 1991b. Development of enucleated mouse oocytes reconstituted with embryonic nuclei. J. Reprod. Fertil. 93:165-172.

Kono, T., O. Y. Kwon, T. Watanabe, and T. Nakahara. 1992. Development of mouse enucleated oocytes receiving a nucleus from different stages of the second cell cycle. J. Reprod. Fertil. 94:481-487.

Kono, T., Y. Shioda, and Y. Tsunoda. 1988. Nuclear transplantation of rat embryos. J. Exp. Zool. 248:303-305.

Kono, T., Y. Sotomaru, F. Aono, T. Takahasi, I. Ogiwara, F. Sekizawa, T. Arai, and T. Nakahara. 1994. Effect of ooplast activation on the development of oocytes following nucleus transfer in cattle. Theriogenology 41:1463-1471.

Kono, T., and Y. Tsunoda. 1989. Development of single blastomeres from four- and eight-cell mouse embryos fused into the enucleated half of a two-cell embryo. Gamete Res. 22:427-434.

Krisher, R. L., R. M. Petters, B. H. Johnson, B. D. Bavister, and A. E. Archibong. 1989. Development of porcine embryos from the one-cell stage to blastocyst in mouse oviducts maintained in organ culture. J. Exp. Zool. 249:235-239.

Kure-bayashi, S., M. Miyake, M. Katayama, T. Miyano, and S. Kato. 1996. Development of porcine blastocysts from in vitro-matured and activated haploid and diploid oocytes. Theriogenology 46:1027-1036.

Kwon, O. Y., and T. Kono. 1996. Production of identical sextuplet mice by transferring metaphase nuclei from four-cell embryos. Proc. Natl. Acad. Sci. USA 93:13010-13013.

Lallemand, Y., and P. Brulet. 1990. An in situ assessment of the routes and extents of colonisation of the mouse embryo by embryonic stem cells and their descendants. Development 110:1241-1248.

Latham, K. E., D. Solter, and R. M. Schultz. 1991. Activation of a two-cell stage-specific gene following transfer of heterologous nuclei into enucleated mouse embryos. Mol. Reprod. Dev. 30:182-186.

Latham, K. E., J. I. Garrels, and D. Solter. 1994. Alterations in protein synthesis following transplantation of mouse 8-cell stage nuclei to enucleated 1-cell embryos. Dev. Biol. 163:341-350.

Laurincik, J., D. Rath, and H. Niemann. 1994a. Differences in pronucleus formation and first cleavage following in vitro fertilization between pig oocytes matured in vivo and in vitro. J. Reprod. Fertil. 102:277-284.

Laurincik, J., P. Hyttel, D. Rath, and J. Pivko. 1994b. Ovulation, fertilization and pronucleus development in superovulated gilts. Theriogenology 41:447-452.

Laurincik, J., P. Hyttel, and V. Kopecny. 1995. DNA synthesis and pronucleus development in pig zygotes obtained in vivo: An autoradiographic and ultrastructural study. Mol. Reprod. Dev. 40:325-332.

Lavoir, M.-C., N. Rumph, A. Moens, W. A. King, Y. Plante, W. H. Johnson, J. Ding, and K. J. Betteridge. 1997. Development of bovine nuclear transfer embryos made with oogonia. Biol. Reprod. 56:194-199.

Lee, K. Y., H. Huang, B. Ju, Z. Yang, and S. Lin. 2002. Cloned zebrafish by nuclear transfer from long-term-cultured cells. Nat. Biotechnol. 20:785-786.

Lee, S. J., V. G. Pursel, and K. S. Chung. 1993. Effects of fusion medium, voltage and micromanipulation on activation of pig oocytes and blastomere development. Theriogenology 39:257 (Abstr.).

LeSimple, M., C. Doumon, M. Labrousse, and C. Houillon. 1987. Production of fertile salamanders by transfer of germ cell nuclei into eggs. Development 100:471-477.

Machaty, Z., M. A. Mayes, and R. S. Prather. 1995. Parthenogenetic activation of porcine oocytes with guanosine-5'-O-(3'-thiotriphosphate). Biol. Reprod. 52:753-758.

Martin, G. R. 1981. Isolation of a pluripotential cell line from early mouse embryos cultured in medium conditioned with teratocarcinoma cells. Proc. Natl. Acad. Sci. USA 78:7634-7639.

McGrath, J., and D. Solter. 1983a. Nuclear transplantation in the mouse embryo by microsurgery and cell fusion. Science 220:1300-1302.

McGrath, J., and D. Solter. 1983b. Nuclear transplantation in the mouse embryo. J. Exp. Zool. 228:355-362.

McGrath, J., and D. Solter. 1984. Inability of mouse blastomere nuclei transferred to enucleated zygote to support development in vitro. Science 226:1317-1319.

Mitalipov, S. M., R. R. Yeoman, K. D. Nusser, and D. P. Wolf. 2002. Rhesus monkey embryos produced by nuclear transfer from embryonic blastomeres or somatic cells. Biol. Reprod. 66:1367-1373.

Meyen, B. A., C. F. Rosenkrans, and D. L. Davis. 1989. Development of pig blastocysts in vitro is altered by serum, bovine serum albumin and amino acids and vitamins. Theriogenology 31:463-471.

Minamihashi, A., A. J. Watson, P. H. Watson, R. B. Church, and G. A. Schultz. 1993. Bovine parthenogenetic blastocysts following in vitro maturation and oocyte activation with ethanol. Theriogenology 40:63-76.

Misener, M., J. W. Pollard, and K. Metzger. 1991. In vitro culture of porcine embryos in CZB medium. Theriogenology 35:244 (Abstr.).

Miyano, T., R. E. Hiro-oka, K. Kano, M. Miyake, H. Kusunoki, and S. Kato. 1994. Effects of hyaluronic acid on the development of 1- and 2-cell porcine embryos to the blastocyst stage in vitro. Theriogenology 41:1299-1305.

Modlinski, J. A., D. Gerhauser, B. Lioi, H. Winking, and K. Illmensee. 1990. Nuclear transfer from teratocarcinoma cells into mouse oocytes and eggs. Development 108:337-348.

Modlinski, J. A., M. A. Reed, T. E. Wagner, and J. Karasiewicz. 1996. Embryonic stem cells: developmental capabilities and their potential use in mammalian embryo cloning. Anim. Reprod. Sci. 42:437-446.

Modlinski, J. A., and Z. Smorag. 1991. Preimplantation development of rabbit embryos after transfer of embryonic nuclei into different cytoplasmic environment. Mol. Reprod. Dev. 28:361-372.

Moens, A., K. Betteridge, A. Brunet, and J. P. Renard. 1996a. Low levels of chimerism in rabbit fetuses produced from preimplantation embryos microinjected with fetal gonadal cells. Mol. Reprod. Dev. 43:38-46.

Moens, A., P. Chesne, F. Delhaise, A. Delval, F.-J. Ectors, F. Dessy, J. P. Renard, and Y. Heyman. 1996b. Assessment of nuclear totipotency of fetal bovine diploid germ cells by nuclear transfer. Theriogenology 46:871-880.

Moens, A., S. Chastant, P. Chesne, K. Betteridge, and J. P. Renard. 1995. Nuclear transfer using gonia from male rabbit fetuses. Theriogenology 43:283 (Abstr.).

Moreadith, R. W., and K. H. Graves. 1992. Derivation of pluripotential embryonic stem cells from the rabbit. Trans. Assoc. Am. Physicians 105:197-203.

Nagai, T. 1987. Parthenogenetic activation of cattle follicular oocytes in vitro with ethanol. Gamete Res. 16:243-249.

Nagashima, H., S. Saito, and H. Yamakawa. 1992. Development of porcine nuclear transplant embryos from 8-16 cell stage donor nuclei. Theriogenology 37:263 (Abstr.).

Nagy, A., E. Gocza, E. M. Diaz, V. R. Prideaux, E. Ivanyi, M. Markulla, and J. Rossant. 1990. Embryonic stem alone are able to support fetal development in the mouse. Development 110:815-821.

Nagy, A., J. Rossant, R. Nagy, W. Abramow-Newerly, and J. C. Roder. 1993. Derivation of completely cell culture-derived mice from early-passage embryonic stem cells. Proc. Natl. Acad. Sci. USA 90:8424-8428.

Naito, K., F. Daen, and Y. Toyoda. 1992. Comparison of histone H1 kinase activity during meiotic maturation between two types of porcine oocytes matured in different media in vitro. Biol. Reprod. 47:43-47.

Niwa, K. 1993. Effectiveness of in vitro maturation and in vitro fertilization techniques in pigs. J. Reprod. Fertil. Suppl. 48:49-59.

Notarianni, E., S. Laurie, R. M. Moor, and M. J. Evans. 1990. Maintenance and differentiation in culture of pluripotential embryonic cell lines from pig blastocysts. J. Reprod. Fertil. Suppl. 41:51-56.

Notarianni, E., C. Galli, S. Laurie, R. M. Moor, and M. J. Evans. 1991. Derivation of pluripotent, embryonic cell lines from the pig and sheep. J. Reprod. Fertil. Suppl. 43:255-260.

Nussbaum, D. J., and R. S. Prather. 1995. Differential effects of protein synthesis inhibitors on porcine oocyte activation. Mol. Reprod. Dev. 41:70-75.

Otaegui, P. J., D. Waddington, and I. Wilmut. 1994a. Nuclear transfer of 4-cell mouse embryos: synchronization with cytoplast partially overcomes nuclear donor cell-cycle effect. J. Reprod. Fertil. Abstr. Series No. 13:24 (Abstr.).

Otaegui, P. J., G. T. ONeill, K. H. S. Campbell, and I. Wilmut. 1994b. Transfer of nuclei from 8-cell stage mouse embryos following use of nocodazole to control the cell cycle. Mol. Reprod. Dev. 39:147-152.

Ouhibi, N., J. Fulka, Jr., J. Kanka, and R. M. Moor. 1996. Nuclear transplantation of ectodermal cells in pig oocytes: Ultrastructure and radiography. Mol. Reprod. Dev. 44:533-539.

Parry, T. W., and R. S. Prather. 1995. Carry-over of mRNA during nuclear transfer in pigs. Reprod. Nutr. Dev. 35:313-318.

Pedersen, R. A. 1994. Studies of in vitro differentiation with embryonic stem cells. Reprod. Fertil. Dev. 6:543-552.

Petr, J., R. Grocholova, J. Rozinek, and F. Jilek. 1996. Activation of in vitro matured pig oocytes by combined treatment of ethanol and cycloheximide. Theriogenology 45:1473-1478.

Petters, R. M., B. H. Johnson, M. L. Reed, and A. E. Archibong. 1990. Glucose, glutamine and inorganic phosphate in early development of the pig embryo in vitro. J. Reprod. Fertil. 89:269-275.

Petters, R. M., and K. D. Wells. 1993. Culture of pig embryos. J. Reprod. Fertil. Suppl. 48:61-73.

Piedrahita, J. A., G. B. Anderson, and R. H. Bondurant. 1990a. Influence of feeder layer type on the efficiency of isolation of porcine embryo-derived cell lines. Theriogenology 34:865-877.

Piedrahita, J. A., G. B. Anderson, and R. H. Bondurant. 1990b. On the isolation of embryonic stem cells: Comparative behavior of murine, porcine and ovine embryos. Theriogenology 34:879-901.

Pinto-Correia, C., C. R. Long, T. Chang, and J. M. Robl. 1995. Factors involved in nuclear reprogramming during early development in the rabbit. Mol. Reprod. Dev. 40:292-304.

Pollard, J. W., C. Plante, and S. P. Leibo. 1995. Comparison of development of pig zygotes and embryos in simple and complex culture media. J. Reprod. Fertil. 103:331-337.

Powell, R., and F. L. Bames. 1992. The kinetics of oocyte activation and polar body formation in bovine embryo clones. Mol. Reprod. Dev. 33:53-58.

Prather, R. S. 1993. Nuclear control of early embryonic development in domestic pigs. J. Reprod. Fertil. Suppl. 48:17-29.

Prather, R. S., F. L. Barnes, M. M. Sims, J. M. Robl, W. H. Eyestone, and N. L. First. 1987. Nuclear transplantation in the bovine embryo: Assessment of donor nuclei and recipient oocyte. Biol. Reprod. 37:859-866.

Prather, R. S., J. Kubiak, G. G. Maul, N. L. First, and G. Schatten. 1991a. The expression of nuclear lamin A and C epitopes is regulated by the developmental stage of the cytoplasm in mouse oocytes or embryos. J. Exp. Zool. 257:110-114.

Prather, R. S., K. E. Hoffman, R. A. Schoenbeck, T. T. Stumpf, and J. Li. 1996. Characterization of DNA synthesis during the 2-cell stage and the production of tetraploid chimeric pig embryos. Mol. Reprod. Dev. 45:38-42.

Prather, R. S., and L. F. Rickords. 1992. Developmental regulation of an snRNP core protein epitope during pig embryogenesis and after nuclear transfer for cloning. Mol. Reprod. Dev. 33:119-123.

Prather, R. S., M. M. Sims, and N. L. First. 1989. Nuclear transplantation in early pig embryos. Biol. Reprod. 41:414-418.

Prather, R. S., M. M. Sims, and N. L. First. 1990. Nuclear transplantation in the pig embryo: Nuclear swelling. J. Exp. Zool. 255:355-358.

Prather, R. S., M. M. Sims, and N. L. First. 1991b. Culture of porcine embryos from the one- and two-cell stage to the blastocyst stage in sheep oviducts. Theriogenology 35:1147-1151.

Prather, R. S., and N. L. First. 1986. Reprogramming of murine blastocoele formation. J. Exp. Zool. 237:347-350.

Prather, R. S., and N. L. First. 1990. Nuclear transfer in marnmalian embryos. Int. Rev. Cytol. 120:169-190.

Prather, R. S., P. A. Eichen, D. K. Nicks, and M. S. Peters. 1991c. Artificial activation of porcine oocytes matured in vitro. Mol. Reprod. Dev. 28:405-409.

Pressice, G. A., and X. Yang. 1994a. Nuclear dynamics of parthenogenesis of bovine oocytes matured in vitro for 20 and 40 hours and activated with combined ethanol and cycloheximide treatment. Mol. Reprod. Dev. 37:61-68.

Pressice, G. A., and X. Yang. 1994b. Parthenogenetic development of bovine oocytes matured in vitro for 24 hr and activated by ethanol and cycloheximide. Mol. Reprod. Dev. 38:380-385.

Prochazka, R., and P. S. Fiser. 1995. Behaviour of blastomere nuclei fused to mouse oocytes is affected by oocyte enucleation and age. Reprod. Nutr. Dev. 35:695-701.

Reed, M. L., M. J. Illera, and R. M. Petters. 1991. In vitro culture of pig embryos. Theriogenology 37:95-109.

Rickords, L. F., M. S. Peters, R. A. Schoenbeck, T. T. Stumpf, and R. S. Prather. 1993. Okadaic acid increases rate of activation of electrically activated in vitro matured porcine oocytes. Theriogenology 39:296 (Abstr.).

Robertson, E., A. Bradley, M. Kuhn, and M. Evans. 1986. Germ-line transmission of genes introduced into cultured pluripotent cells by retroviral vector. Nature (Lond.) 323:445-448.

Robertson, E. J. 1987. Pluripotential stem cells as a route into the mouse germ line. Trends in Genetics 2:9-13.

Robertson, E. J. 1991. Using embryonic stem cells to introduce mutations into the mouse germ line. Biol. Reprod. 44:238-245.

Robl, J. M., B. Gilligan, E. S. Critter, and N. L. First. 1986. Nuclear transplantation in mouse embryos: Assessment of recipient cell stage. Biol. Reprod. 34:733-739.

Robl, J. M., and D. L. Davis. 1981. Effects of serum on swine morulae and blastocysts in vitro. J. Anim. Sci. 52:1450-1456.

Robl, J. M., and N. L. First. 1985. Manipulation of gametes and embryos in the pig. J. Reprod. Fertil. Suppl. 33:101-114.

Robl, J. M., P. Collas, R. Fissore, and J. Dobrinski. 1992a. Electrically induced fusion and activation in nuclear transplant embryos. In: D. C. Chang, B. M. Chassy, J. A. Saunders and A. E. Sowers (Ed.) Guide to Electroporation and Electrofusion. pp. 535-551. Harcourt Brace Jovanovich, San Diego, Calif.

Robl, J. M., R. Fissore, P. Collas, and R. T. Ruby. 1992b. Cell fusion and oocyte activation. Proceedings of the Symp. on Cloning Mammals by Nuclear Transplantation. pp. 21-23. Jan. 15, 1992. Fort Collins, Colo.

Robl, J. M., R. Prather, F. Barnes, W. Eyestone, D. Northey, B. Gilligan, and N. L. First. 1987. Nuclear transplantation in bovine embryos. J. Anim. Sci. 64:642-647.

Rorie, R. W., G. F. Miller, K. B. Nasti, and R. W. McNew. 1994. In vitro development of bovine embryos as affected by different lots of bovine serum albumin and citrate. Theriogenology 42:397-403.

Rosenkrans, C. F., D. L. Davis, and G. Milliken. 1989. Pig blastocyst development in vitro is affected by amino acids. J. Anim. Sci. 67:1503-1508.

Saito, S., N. Strelchenko, and H. Niemann. 1992. Bovine embryonic stem cell-like cell lines cultured over several passages. Roux's Arch. Dev. Biol. 201:134-141.

Saito, S., Y. H. Choi, and N. Oguri. 1993. Parthenogenetic development of porcine oocytes matured in vitro after electrical, ionophore A and ethanol stimulation. Theriogenology 39:303 (Abstr.).

Samake, S., and L. C. Smith. 1996. Synchronization of cell division in eight-cell bovine embryos produced in vitro: Effects of nocodazole. Mol. Reprod. Dev. 44:486-492.

Schoenbeck, R. A., M. S. Peters, L. F. Rickords, T. T. Stumpf, S. L. Terlouw, and R. S. Prather. 1993. Diacylglycerol-enhanced electrical activation of porcine oocytes matured in vitro. Theriogenology 40:257-266.

Schoonjans, L., G. M. Albright, J.-L. Li, D. Collen, and R. W. Moreadith. 1996. Pluripotential rabbit embryonic stem (ES) cells are capable of forming overt coat color chimeras following injection into blastocysts. Mol. Reprod. Dev. 45:439-443.

Schultz, G. A., and S. Heyner. 1993. Growth factors in preimplantation mammalian embryos. Oxford Rev. Reprod. Biol. 15:43-81.

Schwartz, A., P. R. Cook, and H. Harris. 1971. Correction of a genetic defect in a mammalian cell. Nature (Lond.) 230:5-8.

Shi, Z., S. Jiang, and X. Yang. 1993. Synergistic effect of A23187 and cycloheximide allows effective activation of freshly matured bovine oocytes. Theriogenology 39:309 (Abstr.).

Shin, T., D. Kraemer, J. Pryor, L. Liu, J. Rugila, L. Howe, S. Buck, K. Murphy, L. Lyons, and M. Westhusin. 2002. A cat cloned by nuclear transplantation. Nature 415:859.

Sims, M. M., and N. L. First. 1993. Production of calves by transfer of nuclei from cultured inner cell mass cells. Proc. Natl. Acad. Sci. USA 90:6143-6147.

Slapak, J. R., and M. E. Westhusin. 1989. Effect of procedures utilized for nuclear transfer on bovine oocyte activation. Theriogenology 31:258 (Abstr.).

Smith, L. C. 1992. Removal or destruction of meiotic chromosomes of oocytes. Proceedings of the Symp. on Cloning Mammals by Nuclear Transplantation. pp. 21-23. Jan. 15, 1992. Fort Collins, Colo.

Smith, L. C., and I. Wilmut. 1989. Influence of nuclear and cytoplasmic activity on the development in vivo of sheep embryos after nuclear transplantation. Biol. Reprod. 40:1027-1035.

Smith, L. C., and I. Wilmut. 1990. Factors affecting the viability of nuclear transplanted embryos. Theriogenology 33:153-164.

Smith, L. C., I. Wilmut, and R. H. F. Hunter. 1988. Influence of cell cycle stage at nuclear transplantation on the development in vitro of mouse embryos. J. Reprod. Fertil. 84:619-624.

Smith, L. C., I. Wilmut, and R. H. F. Hunter. 1990. Control of first cleavage in single-cell reconstituted mouse embryos. J. Reprod. Fertil. 88:655-663.

Smith, L. D. 1965. Transplantation of the nuclei of primordial germ cells into enucleated eggs of Rana Pipiens. Proc. Natl. Acad. Sci. USA 54:101-107.

Smith, R. K. W., and M. H. Johnson. 1986. Analysis of the third and fourth cell cycles of mouse early development. J. Reprod. Fertil. 76:393-399.

Smith, S. D., E. Soloy, J. Kanka, P. Holm, and H. Callesen. 1996. Influence of recipient cytoplasm cell stage on transcription in bovine nucleus transfer embryos. Mol. Reprod. Dev. 45:444-450.

Solter, D., J. Aronson, S. F. Gilbert, and J. McGrath. 1985. Nuclear transfer in mouse embryos: Activation of the embryonic genome. Cold Spring Harbor Symp. on Quantitative Biology L:45-50. Cold Spring Harbor Laboratory, Cold Spring Harbor, N.Y.

Stewart, C. L. 1993. Production of chimeras between embryonic stem cells and embryos. Methods Enzymol. 225:823-855.

Stice, S. L., C. L. Keefer, and L. Matthews. 1994. Bovine nuclear transfer embryos: Oocyte activation prior to blastomere fusion. Mol. Reprod. Dev. 38:61-68.

Stice, S. L., and J. M. Robl. 1988. Nuclear reprogramming in nuclear transplant rabbit embryos. Biol. Reprod. 39:657-664.

Stice, S. L., N. S. Strelchenko, C. L. Keefer, and L. Matthews. 1996. Pluripotent bovine embryonic cell lines direct embryonic development following nuclear transfer. Biol. Reprod. 54:100-110.

Stone, B. A., P. Quinn, and R. F. Seamark. 1984. Energy and protein sources for development of pig embryos cultured beyond hatching in vitro. Anim. Reprod. Sci. 7:405-412.

Strelchenko, N. 1996. Bovine pluripotent stem cells. Theriogenology 45:131-140.

Strelchenko, N., and S. Stice. 1994. Bovine embryonic pluripotent cell lines derived from morula stage embryos. Theriogenology 41:304 (Abstr.).

Stumpf, T. T., S. L. Terlouw, H. Funashi, R. S. Prather, and B. N. Day. 1993a. Premature chromosome condensation of nuclei transplanted into in vitro matured porcine oocytes. Biol. Reprod. 48 (Suppl. 1): 175 (Abstr.).

Stumpf, T. T., S. L. Terlouw, H. Funashi, R. S. Prather, and B. N. Day. 1993b. Processing of nuclei transplanted into in vitro matured porcine oocytes. Theriogenology 39:322 (Abstr.).

Sukoyan, M. A., A. N. Golubitsa, A. I. Zhelezova, A. Shilov, S. Y. Vatolin, L. Maximovsky, L. Andreeva, J. McWhir, S. Pack, S. Bayborodin, A. Y. Kerkis, H. I. Kizilova, and O. L. Serov. 1992. Isolation and cultivation of blastocyst-derived stem cell lines from American mink (Mustela vison). Mol. Reprod. Dev. 33:418-433.

Sukoyan, M. A., S. Y. Vatolin, A. N. Golubitsa, A. I. Zhelezova, L. A. Semenova, and O. L. Serov. 1993. Embryonic stem cells derived from morulae, inner cell mass, and blastocysts of mink: Comparisons of their pluripotencies. Mol. Reprod. Dev. 36:148-158.

Szollosi, D., R. Czolowska, M. S. Soltynska, and A. K. Tarkowski. 1988. Remodeling of mouse thymocyte nuclei depends on the time of their transfer into activated, homologous oocytes. J. Cell Sci. 91:603-613.

Szollosi, M., and D. Szollosi. 1988. Blebbing of the nuclear envelope of mouse zygotes, early embryos and hybrid cells. J. Cell Sci. 91:257-267.

Tadir, Y., J. Neez, and M. W. Berns. 1992. Laser in assisted reproduction and genetics. J. Assisted Reprod. Genet. 9:303-305.

Tadir, Y., J. Neez, P. Ho, and M. W. Bems. 1993. Lasers for gamete micromanipulation: Basic concepts. J. Assisted Reprod. Genet. 10:121-125.

Takano, H., K. Koyama, C. Kozai, Y. Kato, and Y. Tsunoda. 1993. Effect of aging of recipient oocytes on the development of bovine nuclear transfer embryos in vitro. Theriogenology 39:909-917.

Tarkowski, A. K., and J. Wrobleska. 1967. Development of blastomeres of mouse eggs isolated at the 4- and 8-cell stage. J. Embryol. Exp. Morphol. 18:155-180.

Terlouw, S. L., R. S. Prather, and B. N. Day. 1992. In vitro development of nuclear transplant pig embryos. Theriogenology 37:309 (Abstr.).

Terlouw, S. L., T. T. Stumpf, H. Funashi, R. S. Prather, and B. N. Day. 1993. Pig oocyte activation and processing of transplanted nuclei. Theriogenology 39:329 (Abstr.).

Thibault, C., and R. Ortovant. 1949. Parthenogese experimentale chez la brebis. Comptes Rendus Hebdomadaires des Seances de L'Academie des Sciences, Serie D: Sciences Naturelles 228:510-511.

Thomas, K. R., and M. R. Capecchi. 1987. Site-directed mutagenesis by gene targeting in mouse embryo-derived stem cells. Cell 51:503-512.

Tsunoda, Y., T. Tokunaga, H. Imai, and T. Uchida. 1989. Nuclear transplantation of male primordial germ cells in the mouse. Development 107:407-411.

Tsunoda, Y., and Y. Kato. 1992. Synchronous division of mouse two-cell embryos with nocodazole in vitro. J. Reprod. Fertil. 95:39-43.

Tsunoda, Y., Y. Kato, and G. T. O'Neill. 1992. Cytogenetic analysis of reconstituted one-cell mouse embryos derived from nuclear transfer of fetal male germ cells. J. Reprod. Fertil. 96:275-281.

Tsunoda, Y., Y. Shioda, M. Onodera, D. Nakamura, and T. Uchida. 1988. Differential sensitivity of mouse pronuclei and zygote cytoplasm to Hoescht staining and ultraviolet irradiation. J. Reprod. Fertil. 82:173-178.

Tsunoda, Y., T. Yasui, Y. Shioda, K. Nakamura, T. Uchida, and T. Sugie. 1987. Full-term development of mouse blastomere nuclei transplanted into enucleated two-cell embryos. J. Exp. Zool. 242:147-151.

Uehara, T., and R. Yanagimachi. 1977. Activation of hamster eggs by pricking. J. Exp. Zool. 199:269-275.

Vaughan, T. J., P. S. James, and J. C. Pascall. 1992. Expression of the genes for TGFa, EGF and the EGF receptor during early pig development. Development 116:663-669.

Ware, C. B., F. L. Barnes, M. Maiki-Laurila, and N. L. First. 1989. Age dependence of bovine oocyte activation. Gamete Res. 22:265-275.

Watson, A. J., P. H. Watson, M. Arcellana-Panlilio, D. Warnes, S. K. Walker, G. A. Schultz, D. T. Armstrong, and R. F. Seamark. 1994. A growth factor phenotype map for ovine preimplantation development. Biol. Reprod. 50:725-733.

Webb, M., S. K. Howlett, and B. Maro. 1986. Parthenogenesis and cytoskeleton organization in aging mouse oocyte. J. Embryol. Exp. Morph. 95:131-145.

Westhusin, M. E., M. J. Levanduski, R. Scarborough, C. R. Looney, and K. R. Bondioli. 1992. Viable embryos and normal calves after nuclear transfer into Hoechst stained enucleated demi-oocytes of cows. J. Reprod. Fertil. 95:475-480.

Wheeler, M. B. 1994. Development and validation of swine embryonic stem cells: a review. Reprod. Fertil. Dev. 6:563-568.

Wheeler, M. B., and B. R. White. 1993. Strategies for improving swine growth. In: G. R. Hollis (Ed.) Growth of the Pig. pp. 167-183. CAB International, Wallingford, UK.

Wheeler, M. B., L. A. Rund, and G. T. Bleck. 1995. The use of embryonic stem cells in the production of transgenic livestock. Embryo Transfer Newsletter 13:20-25.

White, K. L., K. Hehnke, L. F. Rickords, L. L. Southern, D. L. Thompson, Jr., and T. C. Wood. 1989. Early embryonic development in vitro by coculture with oviductal epithelial cells in pigs. Biol. Reprod. 41:425-430.

Whitten, W. K., and J. D. Biggers. 1968. Complete development in vitro of the pre-implantation stages of the mouse in a simple chemically defined medium. J. Reprod. Fertil. 17:399-401.

Willadsen, S. M. 1982. Micromanipulation of embryos of the large domestic species. In: C. E. Adams (Ed.) Mammalian Egg Transfer. pp. 185-210. CRC Press, Boca Raton, Fla.

Willadsen, S. M. 1986. Nuclear transplantation in sheep embryos. Nature (Lond.) 320:63-65.

Wilmut, I., A. E. Schnieke, J. McWhir, A. J. Kind, and K. H. S. Campbell. 1997. Viable offspring derived from fetal and adult mammalian cells. Nature (Lond.) 385:810-813.

Wittingham, D. G. 1980. Parthenogenesis in mammals. Oxford Rev. Reprod. Biol. 2:205-231.

Wobus, A. M., H. Holzhausen, P. Jakel, and J. Schoneich. 1984. Characterization of a pluripotent stem cell line derived from a mouse embryo. Exp. Cell Res. 152:212-219.

Wood, S. A., N. D. Allen, J. Rossant, A. Auerbach, and A. Nagy. 1993a. Non-injection methods for the production of embryonic stem cell-embryo chimeras. Nature (Lond.) 365:87-89.

Wood, S. A., W. S. Pascoe, C. Schmidt, R. Kemler, M. J. Evans, and N. D. Allen. 1993b. Simple and efficient production of embryonic stem cell-embryo chimeras by coculture. Proc. Natl. Acad. Sci. USA 90:4582-4585.

Wright, R. W., Jr. 1977. Successful culture in vitro of swine embryos to the blastocyst stage. J. Anim. Sci. 44:854-858.

Yamauchi, N., H. Sasada, S. Sugawara, and T. Nagai. 1996. Effect of culture conditions on artificial activation of porcine oocytes matured in vitro. Reprod. Fertil. Dev. 8:1153-1156.

Yang, X., G. A. Presicce, L. Maroghan, S. Jiang, and R. H. Foote. 1994. Synergistic effect of ethanol and cycloheximide on activation of freshly matured bovine oocytes. Theriogenology 41:395-403.

Yang, X., S. E. Jiang, A. Kovacs, and R. H. Foote. 1992a. Nuclear totipotency of cultured rabbit morulae to support full-term development following nuclear transfer. Biol. Reprod. 47:636-643.

Yang, X., S. Jiang, and Z. Shi. 1992b. Improved activation by combined cycloheximide and electric pulse treatment of bovine follicular oocytes matured in vitro for 23-24 hours. Biol. Reprod. 46 (Suppl. 1):117 (Abstr.).

Youngs, C. R., and L. K. McGinnis. 1990. In vitro culture of porcine embryos in Whitten's medium containing varying levels of glucose and bovine serum albumin (BSA). Biol. Reprod. 42 (Suppl. 1):58 (Abstr.).

Youngs, C. R., S. P. Ford, L. K. McGinnis, and L. H. Anderson. 1993. Investigations into the control of litter size in swine. I. Comparative studies on in vitro development of Meishan and Yorkshire preimplantation embryos. J. Anim. Sci. 71:1561-1565.

Yong, Z., W. Jianchen, Q. Jufen, and H. Zhiming. 1991. Nuclear transplantation in goats. Theriogenology 35:299 (Abstr.).

Zilstra, M., E. Li, F. Sajjadi, S. Subramani, and R. Jaenisch. 1989. Germ-line transmission of a disrupted b2-microglobulin gene produced by homologous recombination in embryonic stem cells. Nature 342:435-438.

We claim:

1. A method for producing a porcine mammal with a nuclear genome of interest, said method comprising the steps of:
   (a) providing a porcine embryonic stem cell comprising a nucleus having a genome of interest;
   (b) providing a porcine oocyte that is a matured and activated oocyte, culturing a porcine oocyte so that it is a matured and activated oocyte, or producing a porcine zygote in vivo or in vitro;
   (c) enucleating the matured and activated oocyte or enucleating the zygote to step (b) to produce an enucleated recipient cell;
   (d) transferring the nucleus of the embryonic stem cell of step (a) to the enucleated recipient cell of step (c) to produce a nuclear transfer embryo;
   (e) culturing the nuclear transfer embryo of step (d) to produce an embryo of a 4-cell, 8-cell, 16-cell, compact morula or blastocyst stage of development; and
   (f) implanting the nuclear transfer embryo of step (d or e) into a surrogate porcine mother mammal,
   whereby a porcine mammal having a nuclear genome of interest is produced.

2. The method of claim 1, further comprising allowing the surrogate mother to carry the porcine mammal to term.

3. The method of claim 1, wherein the embryonic stem cell is a transgenic embryonic stem cell.

4. The method of claim 1, further comprising in step (a), genetically modifying the genome of the embryonic stem cell to comprise at least one heterologous DNA sequence.

5. The method of claim 1, wherein enucleating is by chemical, mechanical, UV, centrifugation or electromagnetic radiation means.

6. The method of claim 5, wherein the chemical enucleating is by contacting oocytes, wherein said oocytes are metaphase I oocytes, with etoposide supplemented medium followed by contacting with a combination of etoposide and cycloheximide.

7. The method of claim 5, wherein the mechanical enucleating is by micromanipulation to remove a germinal vesicle from an immature oocyte, a polar body and metaphase chromosomes from an in vivo or in vitro matured oocyte or a nucleus or pronucleus from a zygote (fertilized oocyte) or embryo produced in vivo or in vitro, or by oocyte bisection.

8. The method of claim 5, wherein the electromagnetic irradiation means of enucleating is by irradiation of oocytes with ultraviolet light.

9. The method of claim 8, wherein the ultraviolet light is 254 nm light and wherein the oocyte is a metaphase II oocyte.

10. The method of claim 5, wherein the mechanical enucleating is by density gradient centrifugation of oocytes.

11. The method of claim 5, wherein the electromagnetic enucleating is by laser irradiation.

12. The method of claim 1, wherein the nucleus is transferred to the enucleated recipient cell of step (c) by microinjection.

13. The method of claim 1, wherein the nucleus is transferred to the enucleated recipient cell of step (c) by electrofusion.

14. The method of claim 1, wherein the nucleus is transferred to the enucleated recipient cell of step (c) by contacting the donor cell and the enucleated recipient cell in the presence of a fusogenic agent.

15. The method of claim 14, wherein the fusogenic agent is an inactivated alpha virus.

16. The method of claim 14, wherein the fusogenic agent is inactivated Sendai virus.

17. The method of claim 14, wherein the fusogenic agent is polyethylene glycol.

18. The method of claim 1, wherein the oocyte is matured in vivo or in vitro and activated in vitro by cold shock, sham enucleation, electroactivation or electro activation in combination with culture in the presence of cycloheximide.

19. The method of claim 1, wherein the recipient cell is a Meishan, Yorkshire, Duroc, Yorkshire×Duroc, Duroc×Yorkshire, Pietrain×Meishan or a Duroc×Meishan cell.

* * * * *